US00RE49772E

(19) United States
(12) Reissued Patent
Goetgeluk et al.

(10) Patent Number: US RE49,772 E
(45) Date of Reissued Patent: Jan. 2, 2024

(54) METHOD GENERATING AN INPUT IN AN OMNIDIRECTIONAL LOCOMOTION SYSTEM

(71) Applicant: VIRTUIX HOLDINGS, INC., Austin, TX (US)

(72) Inventors: Jan Goetgeluk, Austin, TX (US); Ricardo Soza, Round Rock, TX (US); Duane Bester, Houston, TX (US); James Douglas Shuffield, Cedar Park, TX (US)

(73) Assignee: Virtuix Holdings, Inc., Austin, TX (US)

(21) Appl. No.: 17/559,005

(22) Filed: Dec. 22, 2021

Related U.S. Patent Documents

Reissue of:
(64) Patent No.: 10,933,320
Issued: Mar. 2, 2021
Appl. No.: 16/395,776
Filed: Apr. 26, 2019

U.S. Applications:
(63) Continuation of application No. 14/663,433, filed on Mar. 19, 2015, now Pat. No. 10,286,313, which is a (Continued)

(51) Int. Cl.
*A63F 13/40* (2014.01)
*A63F 13/212* (2014.01)

(Continued)

(52) U.S. Cl.
CPC ..... *A63F 13/40* (2014.09); *A63B 69/0035* (2013.01); *A63B 69/0064* (2013.01); *A63B 71/0622* (2013.01); *A63F 13/211* (2014.09); *A63F 13/212* (2014.09); *A63F 13/214* (2014.09); *A63F 13/216* (2014.09); *A63F 13/5255* (2014.09); *G06F 3/011* (2013.01); *A63B 2024/0096* (2013.01); *A63B 2069/0037* (2013.01); *A63B 2071/0638* (2013.01); *A63B 2210/50* (2013.01); *A63B 2220/10* (2013.01); *A63B 2220/12* (2013.01);

(Continued)

(58) Field of Classification Search
CPC ..... A63F 13/40; A63F 13/211; A63F 13/212; A63F 13/214; G06F 3/011; A63B 69/0035; A63B 2220/34; A63B 2220/40; A63B 2220/56; A63B 2024/0096
See application file for complete search history.

(56) References Cited

U.S. PATENT DOCUMENTS 5,782,639 A * 7/1998 Beal ..... A63B 71/0622 434/29
5,792,031 A * 8/1998 Alton ..... A63B 69/0059 482/78

(Continued)

*Primary Examiner* — Adam L Basehoar
(74) *Attorney, Agent, or Firm* — Polsinelli PC

(57) ABSTRACT

A virtual environment can use an absolute orientation framework. An absolute orientation framework in a virtual environment can be activated using an omnidirectional locomotion platform. An absolute orientation framework enables a user's avatar to move independently from the current viewpoint or camera position. The user's avatar can move in an absolute manner relative to a virtual environment map.

48 Claims, 54 Drawing Sheets

Related U.S. Application Data continuation-in-part of application No. 14/062,625, filed on Oct. 24, 2013, now Pat. No. 9,329,681.

(60) Provisional application No. 61/955,767, filed on Mar. 19, 2014, provisional application No. 61/981,149, filed on Apr. 17, 2014, provisional application No. 62/004,550, filed on May 29, 2014, provisional application No. 62/099,426, filed on Jan. 2, 2015, provisional application No. 62/127,261, filed on Mar. 2, 2015.

(51) Int. Cl.

| | |
|---|---|
| ***A63B 24/00*** | (2006.01) |
| ***A63F 13/211*** | (2014.01) |
| ***G06F 3/01*** | (2006.01) |
| ***A63B 71/06*** | (2006.01) |
| ***A63F 13/216*** | (2014.01) |
| ***A63B 69/00*** | (2006.01) |
| ***A63F 13/214*** | (2014.01) |
| ***A63F 13/5255*** | (2014.01) |

(52) U.S. Cl.

CPC ..... *A63B 2220/16* (2013.01); *A63B 2220/34* (2013.01); *A63B 2220/40* (2013.01); *A63B 2220/56* (2013.01); *A63B 2220/70* (2013.01); *A63B 2220/801* (2013.01); *A63B 2220/805* (2013.01); *A63B 2220/806* (2013.01); *A63B 2225/093* (2013.01); *A63B 2225/50* (2013.01)

(56) References Cited

U.S. PATENT DOCUMENTS 5,846,134 A * 12/1998 Latypov ..... A63F 13/00 463/31
5,902,214 A * 5/1999 Makikawa ..... G16H 40/67 482/4
5,913,727 A * 6/1999 Ahdoot ..... A63F 13/06 463/39
5,930,741 A * 7/1999 Kramer ..... A63B 69/3608 340/524
6,135,928 A * 10/2000 Butterfield ..... G06F 3/011 482/69
6,270,414 B2 * 8/2001 Roelofs ..... G06F 3/011 345/157
7,470,218 B2 * 12/2008 Williams ..... A63B 23/0464 482/148
7,780,573 B1 * 8/2010 Carmein ..... A63B 71/0622 482/4
8,456,419 B2 * 6/2013 Wilson ..... G06F 3/038 715/848
8,696,458 B2 * 4/2014 Foxlin ..... G07F 17/3209 345/156
9,816,819 B2 * 11/2017 Keal ..... G01C 21/165
10,668,352 B2 * 6/2020 Wang ..... A63B 26/00
11,000,753 B2 * 5/2021 Kim ..... A63B 23/12
2006/0139317 A1 * 6/2006 Leu ..... G06F 3/011 345/156
2008/0223131 A1 * 9/2008 Vannucci ..... A61B 5/112 73/865.4
2009/0209343 A1 * 8/2009 Foxlin ..... G07F 17/32 463/36
2013/0237378 A1 * 9/2013 Carrell ..... A63C 17/1436 482/51
2014/0044309 A1 * 2/2014 Leyvand ..... G06T 7/194 382/103
2014/0046586 A1 * 2/2014 Keal ..... G01C 21/165 702/160
2014/0092135 A1 * 4/2014 McArdle ..... G06F 3/04815 345/633
2015/0019135 A1 * 1/2015 Kacyvenski ..... A61B 5/0488 702/19
2016/0035228 A1 * 2/2016 Cakmak ..... A63F 13/42 434/247
2019/0209891 A1 * 7/2019 Fung ..... G06F 3/0338

* cited by examiner

METHOD GENERATING AN INPUT IN AN OMNIDIRECTIONAL LOCOMOTION SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a continuation of U.S. application Ser. No. 14/663,433 filed Mar. 19, 2015, which claims benefit of U.S. application Ser. No. 14/062,625 filed Oct. 24, 2013, and entitled "Locomotion System and Apparatus," which is hereby incorporated herein by reference in its entirety. This application claims benefit of U.S. provisional application Ser. No. 61/955,767 filed Mar. 19, 2014, and entitled "Method and System of Decoupling a Locomotion and Virtual Reality System," which is hereby incorporated herein by reference in its entirety. This application claims benefit of U.S. provisional application Ser. No. 61/981,149 filed Apr. 17, 2014, and entitled "Omnidirectional Locomotion System for Military Application," which is hereby incorporated herein by reference in its entirety. This application claims benefit of U.S. provisional application Ser. No. 62/004,550 filed May 29, 2014, and entitled "Support Tube System for Vertical Movement of an Omnidirectional Locomotion Device," which is hereby incorporated herein by reference in its entirety. This application claims benefit of U.S. provisional application Ser. No. 62/099,426 filed Jan. 2, 2015, and entitled "An Omnidirectional Locomotion System and Apparatus," which is hereby incorporated herein by reference in its entirety. This application claims benefit of U.S. provisional application Ser. No. 62/127,261 filed Mar. 2, 2015, and entitled "An Omnidirectional Locomotion System and Apparatus," which is hereby incorporated herein by reference in its entirety.

FIELD OF TECHNOLOGY

The present disclosure relates generally to an omnidirectional locomotion system and apparatus that can be used in conjunction with virtual reality systems, and more specifically to a hardware layout and software methods of a omnidirectional locomotion system and related components.

BACKGROUND

The present disclosure generally relates to locomotion devices that can be used in conjunction with virtual reality systems.

Within a virtual reality environment, users typically desire the ability to walk freely. In particular, the ability to physically walk or run in the real environment and have that motion translated to the virtual environment significantly increases the level of immersion of the user in the virtual environment. However, movement in the real world is often limited by physical space boundaries (e.g., the size of the room within which the user is located). Accordingly, locomotion devices are designed to provide the user the sensation of walking freely, while confining the user to a specific location. For example, many locomotion devices allow a user to walk freely, in 360 degrees, on a platform having a finite size without ever leaving the platform.

Conventional locomotion devices include motorized and non-motorized designs, which may be used in conjunction with virtual reality environments in a multitude of applications including, but not limited, to gaming. Examples of applications beyond gaming include employee training; combat training; physical therapy; exercise; virtual work environments; virtual meeting rooms (for both professional and personal purposes); sports simulation and training; and virtual tourism, concerts, and events.

Motorized locomotion devices typically use sensors to detect the movement of the user and send feedback to motors driving belts or rollers on which the user moves. The belts or rollers are operated to counter the user's movements and bring the user back to a central portion of the platform after each step. There are many drawbacks to motorized locomotion devices. For example, the motorized locomotion devices are usually complex and expensive because of the rolling and motorized components, sensors, processing units, and feedback loops. In addition, complex algorithms are required for the rolling and motorized components to properly counter the movements of the user. Inaccurate feedback to the motor can result in erroneous movement of the belts or rollers that may cause the user to lose balance or drift away from the center of the platform. There may also be issues with latency of feedback and response when the user accelerates, causing incorrect movements or responses that are too slow, potentially allowing the user walk off the platform. Further, because the response movements of the belts or rollers counteract the user's movements, the user may be prone to lose balance and trip.

In addition to issues with the operation of motorized locomotion devices, such devices are usually large and bulky, and thus, do not fit in the average-sized residential room (e.g., a game room, living room, or bedroom) and can be difficult to break up into modular pieces for shipping and storage. The devices are necessarily large, to prevent the user from walking off the platform before the correct system response has been processed; thus, rendering the devices unsuitable for in-home consumer usage.

Non-motorized locomotion devices lack motorized components and, thus, rely on the user's movement and/or gravity to bring the user back to the center of the platform after each step. Omnidirectional ball bearing platforms, for example, have hundreds of ball bearings that allow the user to walk in place while a restraint around the user's waist keeps the user in place. A major issue with omnidirectional ball bearing platforms is that the user does not experience a natural gait with a heel-toe strike movement, but rather instability similar to that of walking on ice. The instability results in the shuffling of feet where neither heel nor toe lift off the device, resulting in an unnatural walking gait that reduces the immersion of the user in the virtual environment. Moreover, these devices are typically heavy and expensive due to the plurality of rolling components.

Accordingly, there remains a need for locomotion devices that allow users to safely access virtual environments while providing the sensation of a more natural walking gait.

SUMMARY

The embodiments described herein are generally directed to a locomotion system for use with a virtual environment technology comprising a platform configured to support a user, a lower platform configured to support the platform and the user while entering the platform, an adjustable struts coupled to the platform and extending upwardly, at variable heights, from the platform, wherein the harness support assembly includes a support halo positioned above the platform and extending about a vertical central axis, and a harness configured to be worn by the user. The harness includes one or more sleds moveably coupled to the support halo.

In an embodiment, a locomotion system for use with a virtual environment technology comprises a platform configured to support a user, struts coupled to the platform and extending upwardly from the platform, wherein the struts includes a support halo positioned above the platform and extending about a vertical central axis, and a harness including a belt configured to be worn by the user, one or more sleds coupled to the belt, and a vertical member coupled to the belt. The sleds slidingly engages an upper and lower surface of the support halo, and the vertical member is disposed within the support halo and is configured to limit the radial movement of the interface structure relative to the support halo.

In an embodiment, a harness for use in an omnidirectional locomotion system comprising a sit harness coupled to a support frame, two upper sleds removably coupled to the support frame by a connection rod, wherein the upper sled is located above a halo, two lower sleds removably coupled to the support frame by a vertical member, wherein the lower sled is located below the halo.

In an embodiment, a virtual reality system comprises a locomotion system including a platform configured to support a user, struts coupled to the platform, and a harness configured to be worn by the user. The struts include a support halo positioned above the platform and extending about a vertical central axis, and wherein the harness is configured to move relative to the support halo. The virtual reality system can further comprise one or more sensors, for example, inertial measurement unit (IMU) configured to detect, track, and transmit the motion of the user to a print circuit board, light emitting diodes (LED) configured to display status information to the user, a cabling system and panel configured to prevent accidental removal, and a visual display in communication with the processing unit, and one or more accessories configured to be handled or used by the user.

The movement of a user in the omnidirectional locomotion system can be determined by data collected from the one or more sensors, for example IMUs. One or more sensors can be removably attached to the user's footwear, harness, accessory, head, arms, or any other location on the user or user accessory. When the user begins movement in any direction the sensors can stream raw gyro data to an aggregator board, for example at 100 Hz. The aggregator board can collect and analyze the data to determine the angular velocity (rate of rotation per second) coming from the gyro that is perpendicular to the direction of the motion. In other embodiments, the sensors can include, but are not limited to capacitance sensors, inertial sensors (IMU), ambient light sensors, magnetic tracking sensors, acoustic sensors, pressure sensors, optical tracking sensors, hall effect sensor, and infrared sensors.

The term "coupled" refers to limitation of movement in the virtual environment with reference to the direction in which the user is looking or where the camera is pointed within the virtual environment.

The term "decoupled" refers to the ability to move in the virtual environment independent of the direction in which the user is looking or the camera is pointed within the virtual environment. In an embodiment, it refers to the ability of the user to walk in any direction on the virtual reality platform (walk movements translated into gamepad input for a computer application that accepts gamepad input) independent of a direction in which the user is looking in the virtual environment. Movements when decoupled are therefore not bound by the direction of the camera or display, when the user is moving, thus enabling a user to look or have a display positioned in any angle, irrespective of the users intended feet and body movement, motion, or direction.

The term "POD" refers generally to a specific type of sensor system, namely a sensor coupled with a multi-controller unit with short-range wireless capabilities. In the present disclosure, the term POD can be interchangeably with the term sensor. The present disclosure in general describes a POD, however, other sensors can be implemented as well, for example, capacitance sensors, inertial sensors (IMU), ambient light sensors, magnetic tracking sensors, acoustic sensors, pressure sensors, optical tracking sensors, hall effect sensor, and infrared sensors.

Current video games use a relative orientation framework. Pushing a joystick to the right or pressing "D" on a keyboard can move a user's avatar 90 degrees to the right from a current viewpoint or camera position. The current camera position can be obtained by measuring a direction of a head mounted display, for example, a virtual reality headset. Thus in the relative orientation framework, movement can be relative to the current camera position. To further illustrate, pushing the joystick up or "W" on the keyboard can move the user's avatar in the forward in the current camera position.

In an embodiment, a game can use an absolute orientation framework (decoupled framework). When a game is played using an omnidirectional locomotion platform a user's avatar can move independently from the current viewpoint or camera position. The user's avatar can move in an absolute manner relative to an in-game map. For example, if the user walks the direction north on omnidirectional locomotion platform, the user's avatar can move north on the in-game map, regardless of the current camera position. In an embodiment, the head mounted display can include a sensor, for example, a magnetometer. The sensor can use an absolute orientation framework similar to omnidirectional locomotion platform, wherein the current in-game camera position can be the direction the user is physically looking outside the game.

In an embodiment, the direction "north" can be magnetic north or polar north. In another embodiment, the direction "north" can be a designated direction set or calibrated at a start of a game. For example, a user wearing a head mounted display (virtual reality headset), can look forward relative to the user's body during calibration, which can calibrate the current forward looking direction with a forward walking orientation prior to decoupling the current camera position and the user's body position. In another embodiment, the halo or harness of an omnidirectional locomotion system, can include sensors to calibrate the forward position of a user with the forward orientation in-game prior to decoupling the current camera position and the user's body position. In another embodiment, upon initiation of a game the current position of the user outside of the game, determined by the sensors in omnidirectional locomotion platform, the harness, or the headset can be calibrated to the starting position of the game. For example, if an in-game user is initiated facing east, then the direction the outside user is facing when the game is initiated can be calibrated east.

In an embodiment, decoupling can be implemented in existing games. Existing games are not configured for decoupling, however the decoupling effect can still be achieved by generating one or more keystrokes based on the user's current camera position. For example, if the user walks forward on the omnidirectional locomotion platform while looking 90 degrees to the left, decoupling can be accomplished by generating the "D" key or left movement key. The absolute orientation framework can be converted to the relative orientation framework by taking into account the current camera direction. In another example, if the user walks forward on the omnidirectional locomotion platform while looking 45 degrees to the right, achieving the decoupling effect can be accomplished by generating the "W" and "A" keys simultaneously or in an alternating manner. In another example, if the user walks forward on the omnidirectional locomotion platform while looking 15 degrees to the right, achieving the decoupling effect can be accomplished by generating more "W" keys than "A" keys.

In an embodiment, a method for detecting a quick stop on an omnidirectional locomotion system can comprise, receiving an angular velocity at a predefined interval, determining a user movement based on the angular velocity, applying a smoothing filter on the angular velocity, determining when the angular velocity is equal or less than a predefined threshold, calculating a slope of the angular velocity, determining when the slope approaches zero for a predefined interval, determining the quick stop when the angular velocity is within the predefined threshold and the slope approaches zero for a predefined interval.

In an embodiment, a locomotion system platform can include sensors, wherein the sensors can be used to determine characteristics of the user operating the locomotion system. The sensors can be located on or within the platform, or on a user of the platform. Another embodiment, relates to an absolute orientation framework, where a character is able to move independently from the camera position (which is the user's viewpoint). The direction a user is looking is ignored and the user can move in an absolute way. If the user walks "north" on the locomotion system, the user in the game will move North in the game, regardless of the camera position.

In an embodiment, a locomotion system platform can comprise one or more sensors distributed in a geometric pattern, one or more electronically coupled printed circuit boards, the one or more sensors electronically coupled to the one or more printed circuit boards, one or more micro-controller units, the one or more micro-controller units electronically coupled to the one or more printed circuit boards and a computer system. The micro-controller units can be electronically coupled to the printed circuit boards and computer system by short-range wireless, for example Bluetooth, WI-FI, or NFS. The computer system can be a server, gaming system, or mobile device, for example, an XBOX, PlayStation, Nintendo, a mobile phone, a tablet, a laptop, a smartphone or a PDA. The sensors can include, but are not limited to capacitance sensors, inertial sensors (IMU), ambient light sensors, magnetic tracking sensors, acoustic sensors, pressure sensors, optical tracking sensors, hall effect sensor, and infrared sensors. In another embodiment, the geometric pattern is concentric circles.

In an embodiment, a forward step can be generated when one or more sensors on a halo are activated. For example, one or more sensors in a halo or platform can be activated by a capacitance reading. Capacitance and time data from the activated sensor can be stored in a computer system. A determination can be made if one or more adjacent sensors are activated. In another embodiment, one or more sensors on a user can be actuated by an inertial measurement or optical measurement. A forward step can be generated.

In an embodiment, a velocity vector can be generated when one or more sensors on a halo are activated. For example, one or more sensors in a halo or platform can be activated by a capacitance reading. Capacitance and time data from the activated sensor can be stored in a computer system. A determination can be made if one or more adjacent sensors are activated. In another embodiment, one or more sensors on a user can be actuated by an inertial measurement or optical measurement. A velocity vector can be generated.

In an embodiment, a step direction can be calculated. One or more sensors can transmit location data and capacitance values to a computer system. In another embodiment, one or more sensors can transmit inertial measurement or optical measurement values. The computer system can normalize the location data of the one or more sensors. The computer system can further weight the normalized position vectors. The computer system can further accumulate the weighted normalized position vectors. The computer system can further normalize the accumulated vectors.

In an embodiment, a velocity of one or more steps can be calculated. A computer system can zero sensors, for example in a center zone. One or more sensors can transmit location data and capacitance values to a computer system. In another embodiment, one or more sensors can transmit inertial measurement or optical measurement values. The computer system can normalize the location data of the one or more sensors. The computer system can further weight the normalized position vectors. The computer system can further accumulate the weighted normalized position vectors. The computer system can further normalize the accumulated vectors. The computer system can determine the length of the accumulated vector. The computer system can calculate the velocity of the accumulated vector.

In an embodiment, a locomotion system platform can provide natural vertical movement. The vertical movement can enable a user to crouch or jump while operating the locomotion system. The vertical movement can comprise a ball bearing system, a spring counterweight, an overheard spring suspension, a pivot arm, a magnetic levitation, a hydraulic actuation, and/or a compressed gas system.

In an embodiment, a locomotion system can comprise a braking mechanism, specifically to prevent a user from falling. When a user is operating the locomotion system, a horizontal force is applied. The concave base of the locomotion system, while enabling a user forward movement by the applied horizontal force, can cause a user to fall or lose balance. A braking mechanism can prevent a user from falling or losing balance by counteracting the horizontal force. The braking mechanism can comprise a counterweight, a frictional force, and cable brake.

In an embodiment, the locomotion system can accommodate an industrial user. The locomotion system can accommodate a user using a weapon, for example an M4 carbine. The locomotion system can further accommodate a user dressed in standard industrial gear and attire, for example a modular tactical vest, patrol pack, improved load bearing equipment (ILBE), and modular lightweight load-carrying equipment (MOLLE).

In an embodiment, the standard industrial gear can integrate with the locomotion system, specifically, load bearing/carrying equipment can attach to the locomotion system harness. The attachment can be done using Pouch Attachment Ladder System (PALS).\

In an embodiment, a method of generating a gaming input comprising calculating a velocity, calculating a heading, translating the velocity and the heading into 2-dimensional Cartesian coordinates, normalizing the 2-dimensional Cartesian coordinates into a minimum to maximum scale range. In an embodiment, the velocity can be calculated by a distance one or more of a user's foot travels divided by the time it took to travel the distance. In another embodiment, the velocity can be calculated by a pedometry rate, wherein the pedometry rate is determined by monitoring a frequency of steps over a predefined interval. In another embodiment, the velocity can be calculated by monitoring an acceleration of one or more of a user's foot. In another embodiment, the velocity is calculated by normalizing an angular velocity, wherein the angular velocity is a change in rotation of one or more of a user's foot. In another embodiment, the heading can be translated relative to a real world axis and the real world axis can be magnetic North. In another embodiment, the heading can be calibrated to a magnetic North to an initial orientation of a user by an offset. In another embodiment, the heading can be translated relative to an orientation of a user's torso. In another embodiment, the heading can be translated relative to an orientation of a user's head. In another embodiment, the minimum to maximum scale range is defined by gaming input descriptors. In another embodiment, the Y 2-dimensional Cartesian coordinate is for forward or backwards movement. In another embodiment, the X 2-dimensional Cartesian coordinate is for sideways movement.

In another embodiment, a method of generating a stop gaming input comprising calculating a velocity, wherein the velocity is a change in rotation of one or more of a user's foot, normalizing the velocity, determining when the normalized velocity drops below a predefined threshold, determining when a slope of the normalized velocity approaches zero for a predefined interval.

In another embodiment, a method comprising receiving one or more sensor output, calculating a velocity from the one or more sensor output, calculating a heading from the one or more sensor output, translating the velocity and the heading into 2-dimensional Cartesian coordinates, normalizing the 2-dimensional Cartesian coordinates into a minimum to maximum scale range.

BRIEF DESCRIPTION OF THE DRAWINGS

In order to describe the manner in which the features of the disclosure can be obtained, a more particular description of the principles briefly described above will be rendered by reference to specific examples thereof which are illustrated in the appended drawings. Understanding that these drawings depict only example embodiments of the disclosure and are not therefore to be considered to be limiting of its scope, the principles herein are described and explained with additional specificity and detail through the use of the accompanying drawings in which.

DETAILED DESCRIPTION

Various examples of the disclosure are discussed in detail below. While specific implementations are discussed, it should be understood that this is done for illustration purposes only. A person skilled in the relevant art will recognize that other components and configurations can be used without parting from the scope of the disclosure. In other instances, well-known methods, procedures, components, circuits, and networks have not been described in detail so as not to necessarily obscure aspects of the embodiment.

It will also be understood that, although the terms first, second, etc. can be used herein to describe various elements, these elements should not be limited by these terms. These terms are only used to distinguish one element from another. For example, a first sensor could be termed a second sensor, and similarly, a second sensor could be termed a first sensor, without departing from the scope of the present invention.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting

[the stated condition or event]" or "in response to detecting [the stated condition or event]," depending on the context.

Figure 1:
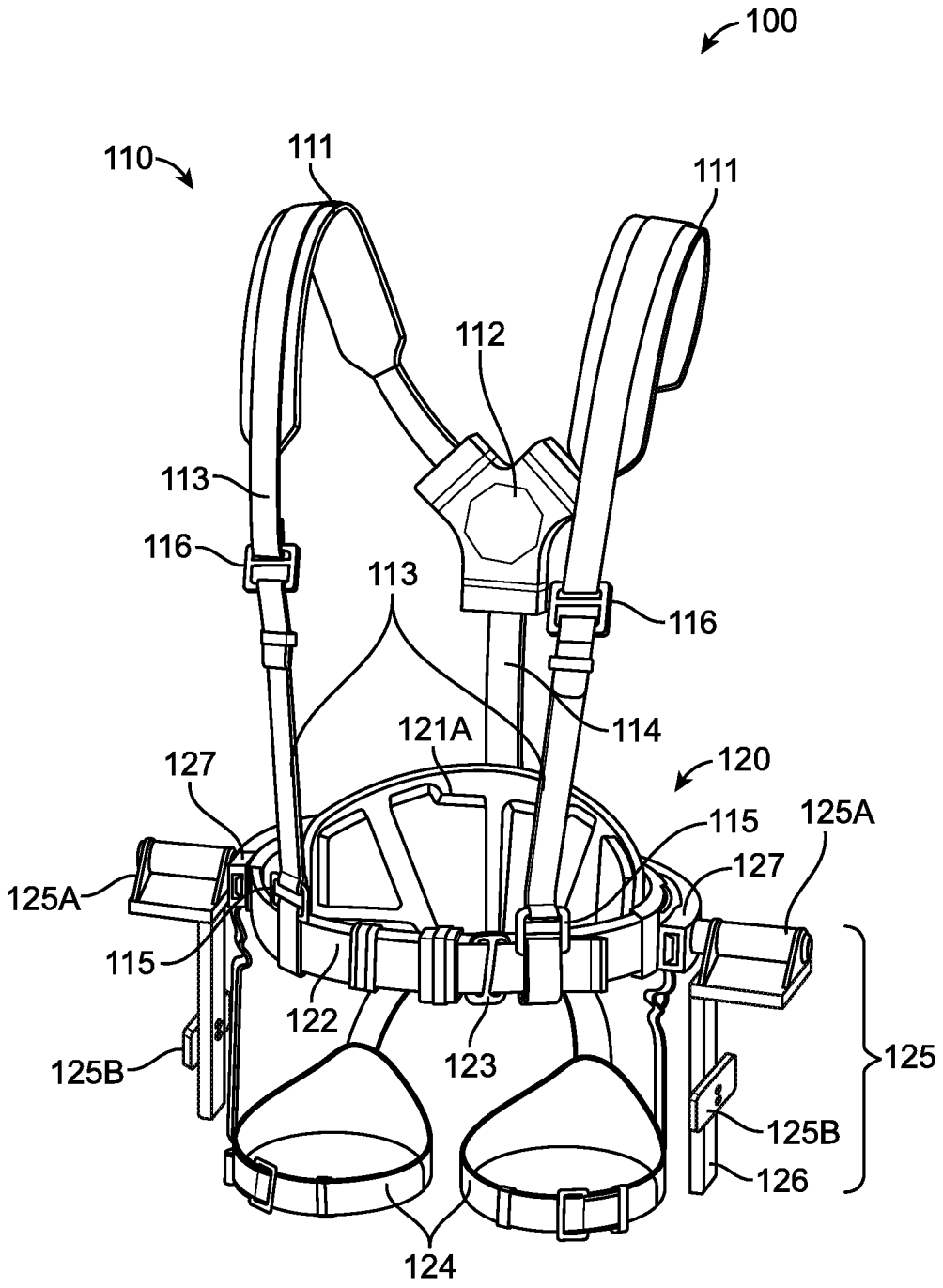
FIG. 1 illustrates an example harness system, in accordance with an example embodiment of the present technology.

FIG. 1 illustrates an example full-body harness system 100. Chest harness 110 can be configured for use with sit harness 120 by connectors 115 for added stability, balance, and ability to maintain upright position. In an embodiment, sit harness 120 can be used without chest harness 110. Chest harness 110 can include shoulder straps 113 and back strap 114 connected by Y-connector 112. Shoulder straps 113 can include shoulder pads 111 and can be extended or shortened by adjusters 116. Sit harness 120 can include a waist strap 122 with adjustable waist strap buckle 123, back pad 121A for added support and adjustable leg loops 124. Sit harness 120 can further include a support frame 127. Support frame 127 can be comprised of hard plastic, metal, polymer, carbon fiber, any combination thereof, or any other material to support of a user's weight. Sleds 125 and vertical member 126 can be removably attached to support frame 127.

Figure 2A:
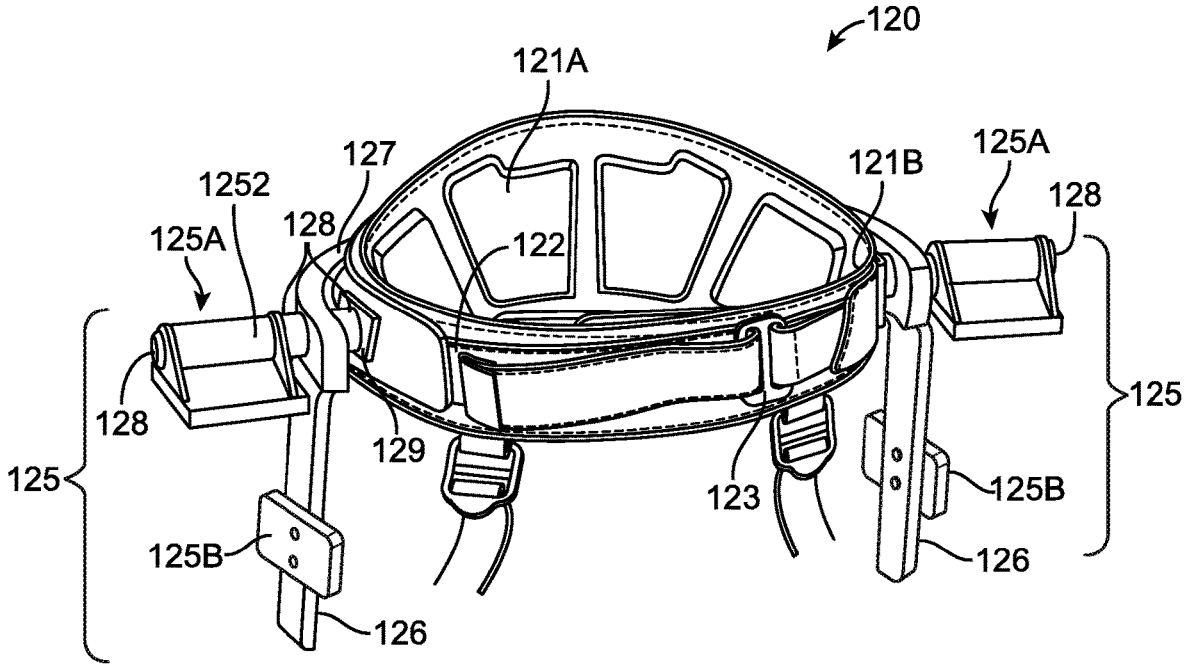
FIG. 2A and FIG. 2B illustrate an example sled connection of an example harness system, in accordance with an example embodiment of the present technology.
Figure 2B:
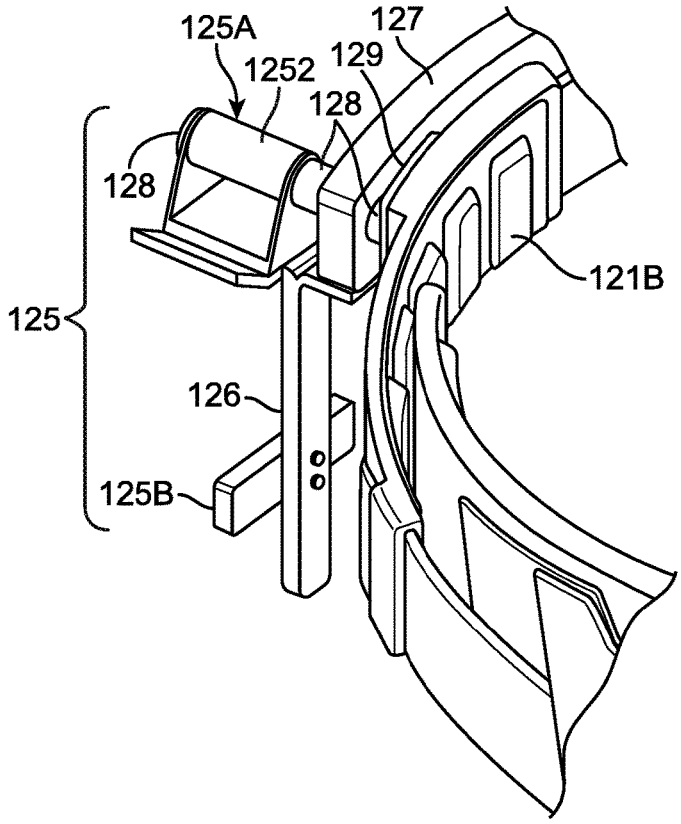

FIG. 2A and FIG. 2B illustrate an example sled connection of a sit harness system 120. Bracket 129 can attach to sit harness 120 by back pad 121A, side pad 121B, waist strap 122 or a combination thereof. Connection rod 128 attaches to bracket 129 through support frame 127. Connection rod 128 can be supported by support frame 127. Connection rod 128 can be configured as a telescoping rod enabling an extension in length when a user of slighter statute is using sit harness 120 and a shortening in length when a user of larger statute is using sit harness 120. Extension and shortening of connection rod 128 enables a connection with sleds 125 with a user of most any size. In another embodiment, connection rod 128 and bracket 129 can also be configured to slide forward and backwards along waist strap 122 of sit harness 120 to enable users of slighter or larger statute to tighten or loosen sit harness 120 and enable connection rod 128 to maintain a perpendicular position to a user's torso. In another embodiment, connection rod 128 can slide along bracket 129. In another embodiment, bracket 129 can slide along waist harness 122. Support frame 127 can support connection rod 128, which connects sit harness 120 to support frame 127, for example to keep the user from falling. The combination of connection rod 128 and bracket 129 can be supported by support frame 127. Side pads 121B can provide added comfort and support for a user at the bracket 129 attach point.

Figure 3:
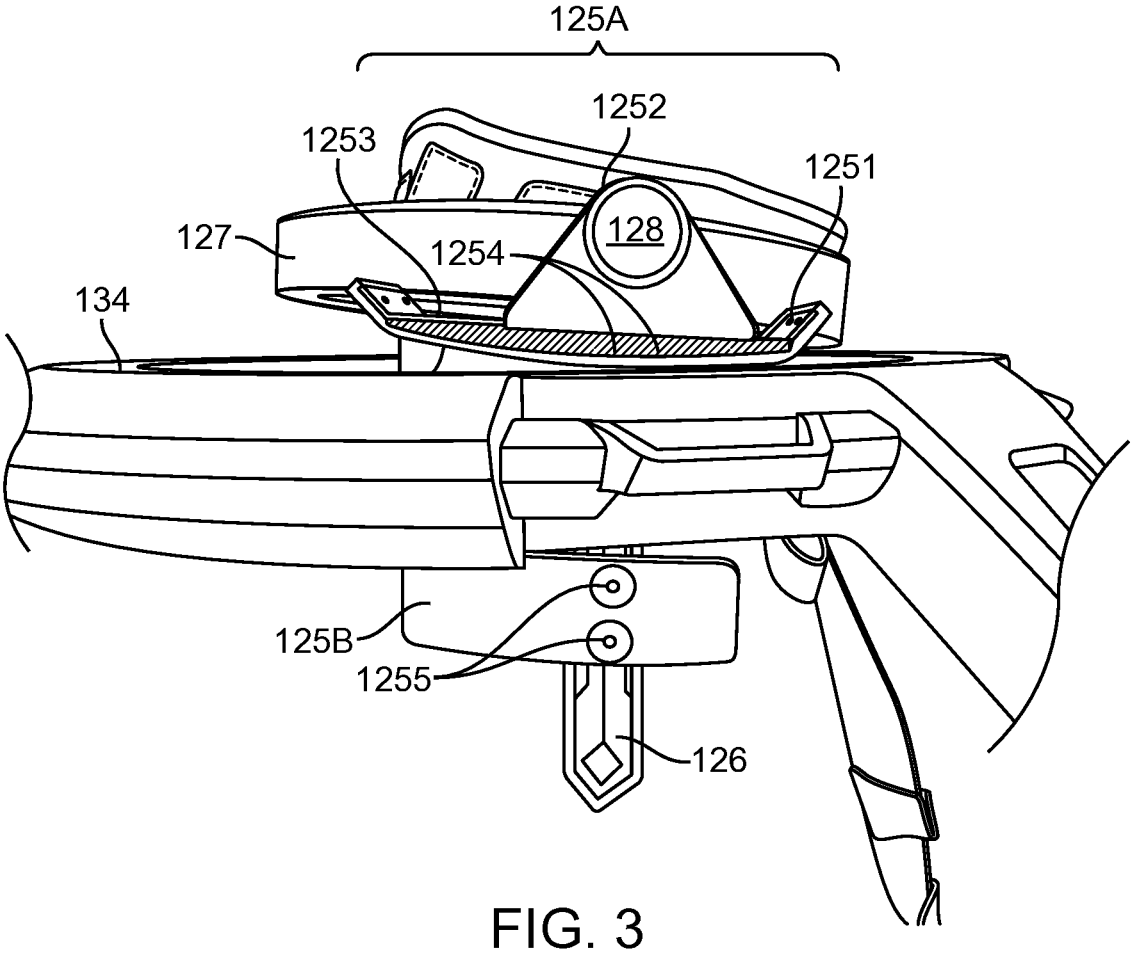
FIG. 3 illustrates an example sled system of an harness system, in accordance with an example embodiment of the present technology.

FIG. 2A, FIG. 2B, and FIG. 3 illustrate an example sled connection of a sit harness system 120 with halo 134. Sleds 125 and vertical members 126 can be removably attached to support frame 127 by connection rods 128. Sleds 125 and vertical members 126 can be made of a low-friction material that glides on, inside, and underneath halo 134. Sleds 125 can include upper sleds 125A and lower sleds 125B. In an embodiment only upper sleds 125A can be configured for use. In another embodiment both upper sleds 125A and lower sleds 125B are configured for use. Upper sleds 125A can be removably attached to connection rods 128. Lower sleds 125B can be removably attached to vertical members 126. In an embodiment, lower sleds 125B can be attached further up or further down vertical members 126 enabling decreased or increased interaction between lower sleds 125B and halo 134, respectively. Sleds 125 can be dynamically independently configured to rotate with a user movement or statically independently configured to not move with a user movement. The surface of sleds 125 can be of a rounded shape to minimize a contact area between sleds 125 and halo 134. Rounded-shape sleds 125 can enable a smooth glide during impact with halo 134. Halo 134 can be substantially torus shape to further minimize an impact area with sleds 125.

Upper sleds 125A can be configured to sit on top of halo 134 and lower sleds 125B can be configured to sit below halo 134. Upper sleds 125A and lower sleds 125B can enable a user to move in 360 degrees while providing added stability and preventing the user from falling (in any direction). In an embodiment, upper sleds 125A are configured for use, and lower sleds 125B are not configured for use, enabling the user the capability to jump. In another embodiment, when both upper sleds 125A and lower sleds 125B are configured for use, lower sleds 125B can contain a sensor (for example a Hall effect sensors, pressure sensors or IMU) for detecting a user jump movement and upper sleds 125A can contain a sensor (for example a Hall effect sensor, pressure sensor or IMU) for detecting a user crouch movement. In another embodiment, vertical members 126, upper sleds 125A, lower sleds 125B, or any other location on the sit harness 120, can include a sensor (for example, a Hall effect sensor, a pressure sensor or IMU sensor) configured to determine the orientation of sit harness 120 (and the orientation of the user's torso). In another embodiment, one or more Hall effect sensors can be arranged in or around halo 134. In another embodiment, one or more Hall effect sensors can be arranged in or around vertical members 126, upper sleds 125A, lower sleds 125B, or sit harness 120. One or more magnets can be arranged in or around vertical members 126, upper sleds 125A, lower sleds 125B, and sit harness 120 to communicate with the Hall effect sensors in halo 134 or sit harness 120.

FIG. 3 illustrates an example sled connection of a sit harness system 120 with halo 134. Upper sleds 125A can include a connection portion 1252 for removably attaching to connection rod 128. In an embodiment, upper sleds 125A can be configured at different positions along connection rod 128 for increasing or decreasing impact with halo 134, for example, closer to or further from the base of connection rod 128. In another embodiment, upper sleds 125A can be locked in place to prevent rotation around connection rod 128. Upper sleds 125A can further include a front portion 1251 and a rear portion 1253, where a front portion 1251 is shorter in length than a rear portion 1253 to provide a user with added stability. For example, an extended length of a rear portion 1253 can provide a user with added balance and prevent a backwards fall. In an embodiment, sleds 125A, can be rounded convex, concave, a flat surface, or any other shape as to minimize the contact surface with the top of halo. In an embodiment, to prevent excessive noise, upper sleds 125A can include a rubberized layer 1254 enabled to dampen noise and impact of upper sleds 125A. In another embodiment, rubberized layer 1254 can be metal springs or any other material to reduce impact noise. In another embodiment to prevent excessive noise, impact portions of upper sleds 125A with halo 134 can be configured with a rubberized surface, metal springs or any other material to reduce impact noise. In another embodiment, a sled can include full rollers to provide easy forward and reverse movements of a user.

Lower sleds 125B can include connection portions 1255 for removably attaching to vertical member 126. In an embodiment, lower sleds 125B can be can be substantially the same length as upper sleds 125A. In another embodiment, lower sleds 125B can be of a smaller size or larger size than upper sleds 125A. The width of lower sleds 125B can be narrow to not interfere with support struts. The impact portions of lower sleds 125B, which can come into contact with halo 134, can be rounded to aid user movement and minimize contact with halo 134. In another embodiment, the impact portion of lower sleds 125B can be rounded convex, concave, a flat surface, or any other shape as to minimize the contact surface with the underside of halo 134 while maximizing the desired functionality of preventing tilt. During operation, lower sled 126B can prevent a user from excessive tilting and provide more stability and security to the user, for example, when the user tilts forward or backwards, respectively the back or front of the lower sleds 125B impacts the underside of halo 134 preventing further tilting providing more stability and security to the user. The space between halo 134 and lower sleds 125B can determine the amount of tilt for the user. The space between halo 134 and lower sleds 125B can be altered by adjusting lower sleds 125B along vertical member 126. In an embodiment lower sleds 125B can be configured 0.25 inches below halo 134 providing the user with added stability while still enabling the user a full range of motion. The length of the lower sleds 125B can determine the amount of forward and backward tilt of a user, for example, a shorter length of lower sleds 125B enables the user more forward and backward tilt where a longer length of lower sleds 125B enables the user less forward and backwards tilt. To prevent excessive noise, lower sleds 125B can include a rubberized layer (not shown) enabled to dampen noise and impact of lower sleds 125B. In another embodiment, the rubberized layer can be metal springs or any other material to reduce impact noise. In another embodiment to prevent excessive noise, impact portions of lower sleds 125B with halo 134 can be rubberized, metal springs or any other material to reduce impact noise. In another embodiment, a sled can include full rollers to provide easy forward and reverse movements of a user.

Figure 4:
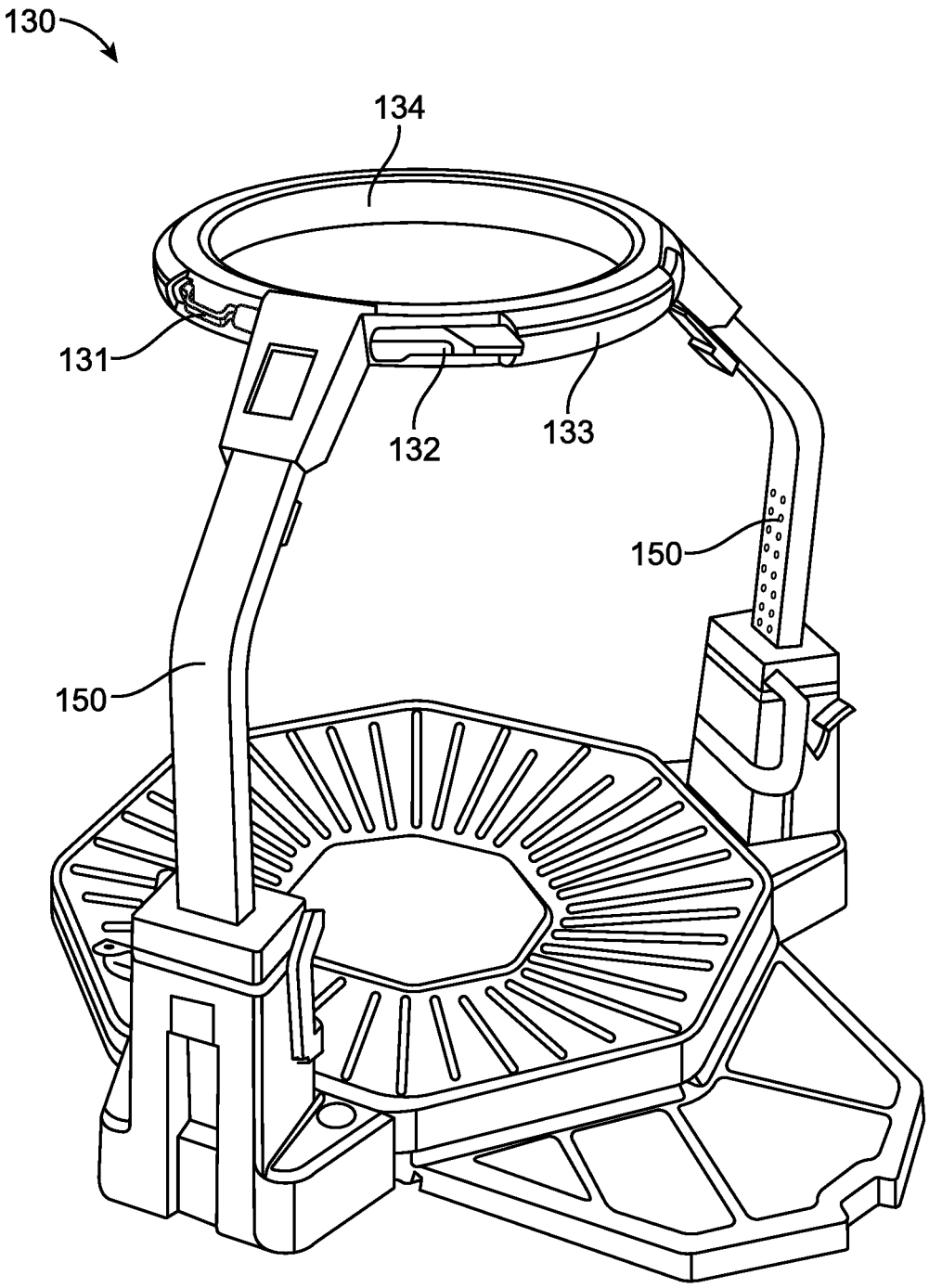
FIG. 4 illustrates an example handle and latching system of an example support halo, in accordance with an example embodiment of the present technology.
Figure 5B:
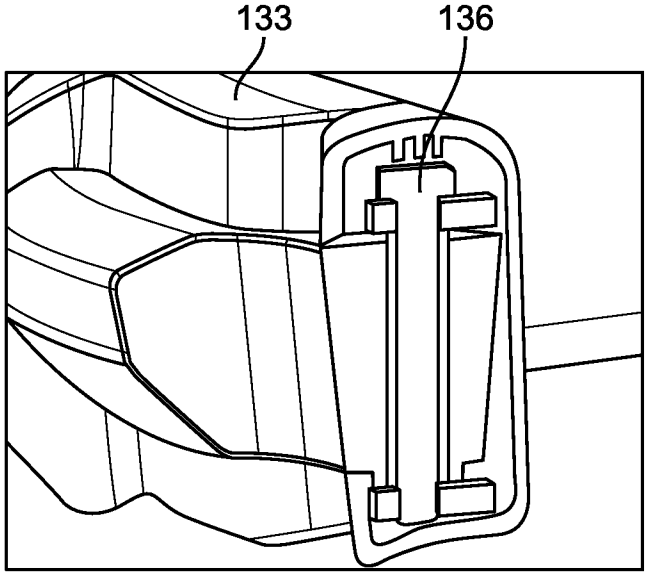
FIG. 5A and FIG. 5B illustrate an example latching system of an example support halo, in accordance with an example embodiment of the present technology.
Figure 5A:
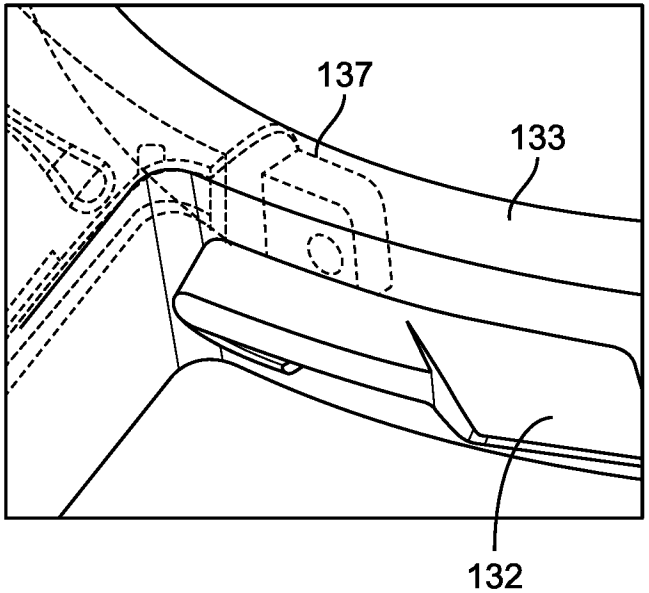
Figures 6A, 6B:
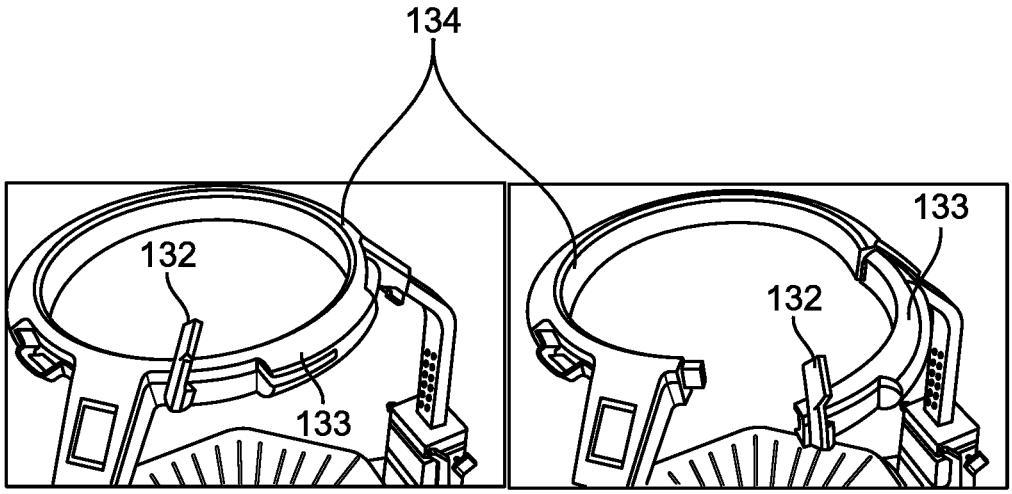
FIG. 6A, FIG. 6B and FIG. 6C illustrate an example closed and example open support halo, in accordance with an example embodiment of the present technology.
Figure 6C:
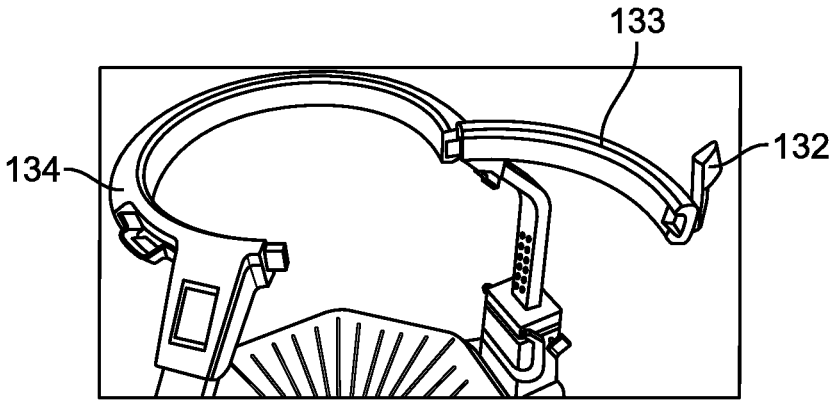

FIG. 4 illustrates an omnidirectional locomotion system 130. Halo 134 of an omnidirectional locomotion system 130 can include one or more handles 131. Handles 131 can aid in adjusting a height of halo 134 by extending or shortening struts 150. Halo 134 can also include a lever 132 for opening and closing door 133 for entering an omnidirectional locomotion system 130. In an embodiment, lever 132 can be a lift-up tail design. In another embodiment, lever 132 can be spring loaded. Lever 132 can further stay in an upright position when not closed for added safety. Door 133 and lever 132 can further include a safety pin (not shown) for additional safety against accidental opening. FIG. 5A and FIG. 5B illustrate lever 133 with latching mechanism 137 and door 133 with hinge 136. FIGS. 6A, 6B and 6C illustrate door 133 in different states: closed and unlocked, partial open, and fully open, respectively.

Figure 7:
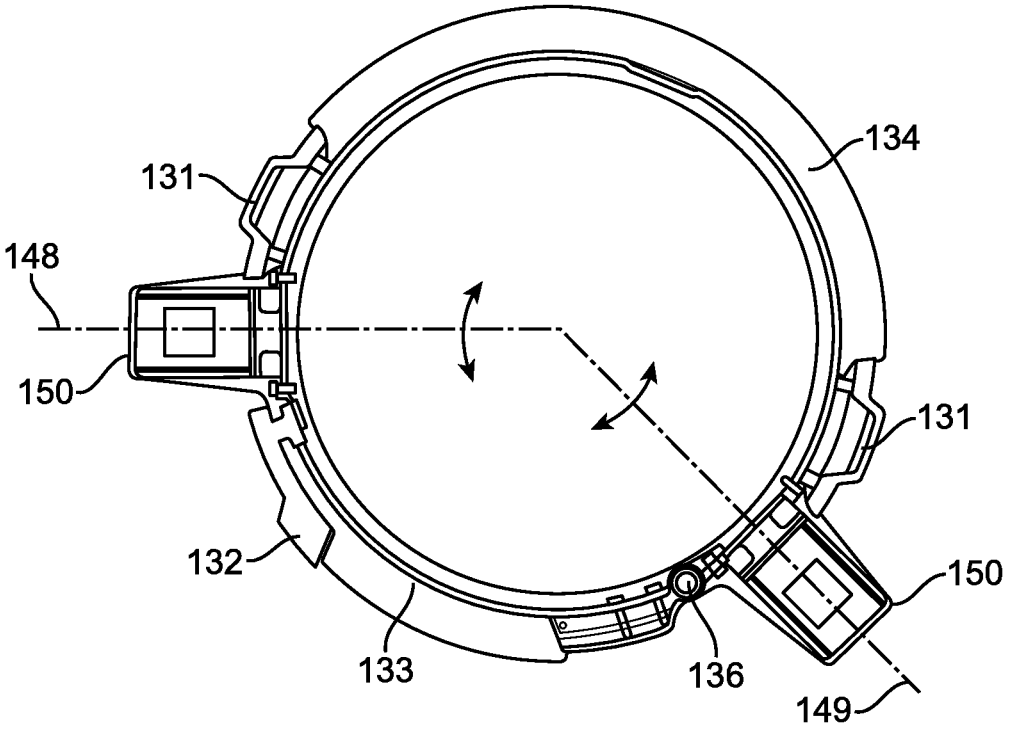
FIG. 7 is a top view illustrating an example support halo, in accordance with an example embodiment of the present technology.

FIG. 7 is a top view illustrating an example halo 134 and relative positioning of handles 131, lever 132, door 133, hinge 136, and struts 150. In an embodiment, Struts 150 can be offset. In an embodiment, struts 150 can be positioned on different axes, for example, one strut 150 can be positioned on axis 148 and the other strut 150 can be positioned on axis 149.

Figure 8:
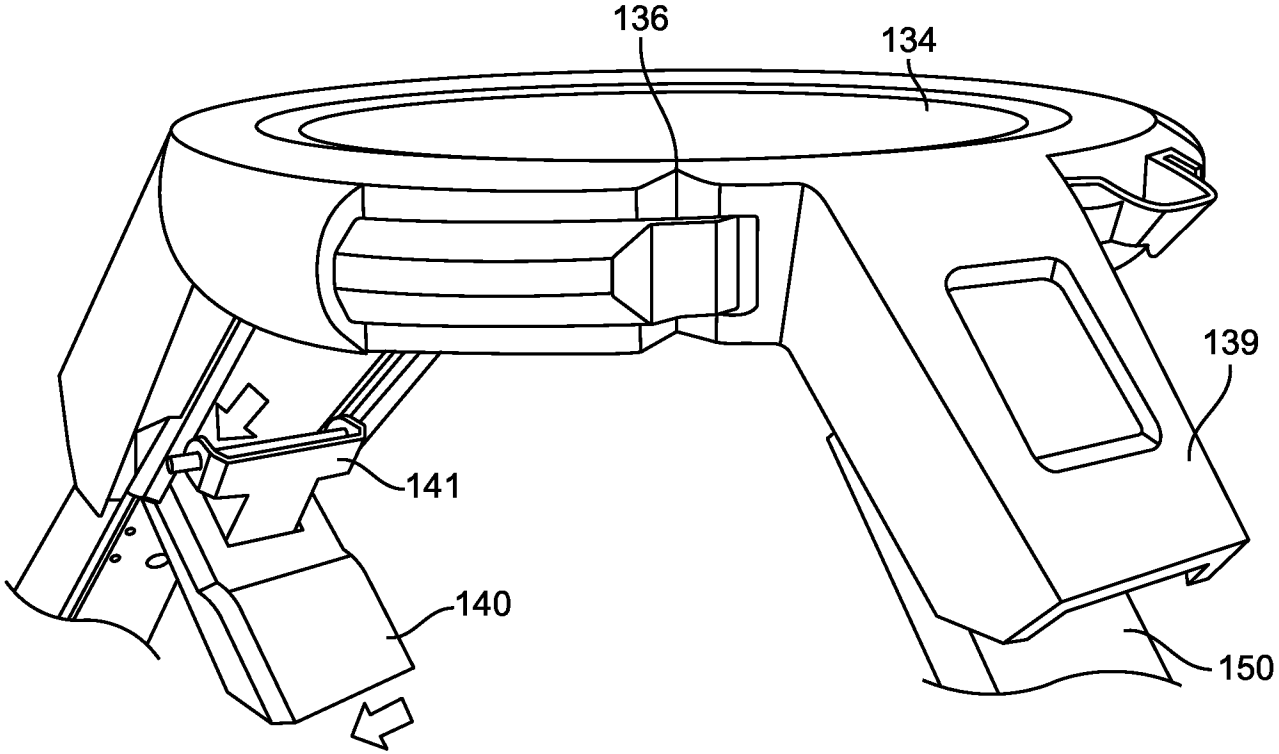
FIG. 8 illustrates an example attachment mechanism of an example support halo, in accordance with an example embodiment of the present technology.
Figure 9B:
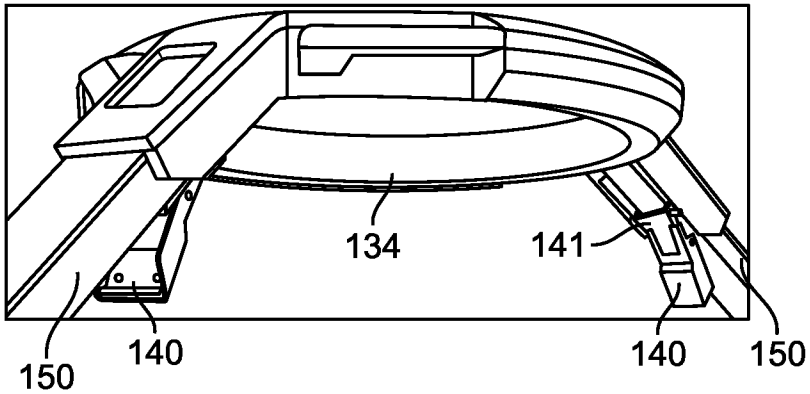
FIG. 9A, FIG. 9B, FIG. 9C, and FIG. 9D illustrate an example attachment mechanism of a support halo, in accordance with an example embodiment of the present technology.
Figure 9A:
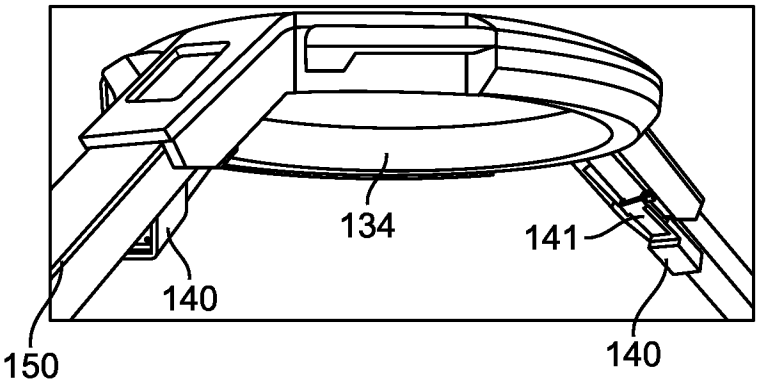
Figure 9D:
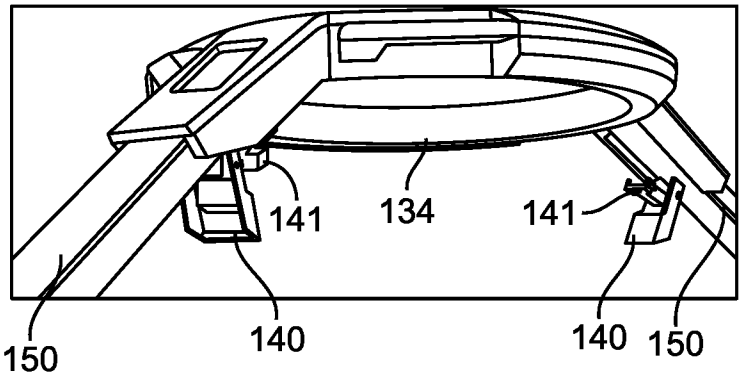
Figure 9C:
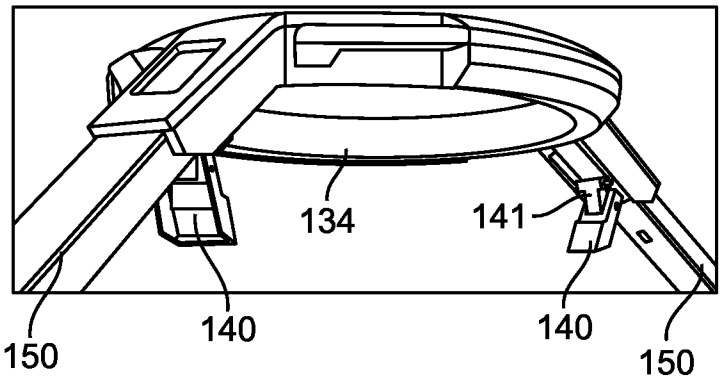

FIG. 8 illustrates an example halo 134 attachment mechanism. Halo 134 can include U-shaped flanges 139. U-shaped flanges 139 can attach to struts 150 by quick release fixtures including handle 140 and quick release latch 141. In an embodiment, any other type of connection and release mechanism can be used. In another embodiment, halo 134 is permanently attached to struts 150. FIGS. 9A, 9B, 9C and 9D illustrate the quick release fixture in different states of connectivity. FIG. 9A illustrates handle 140 and quick release latch 141 engaged with struts 150. FIG. 9B illustrates handle 140 released from struts 150. FIG. 9C illustrates handle 140 released from struts 150 and latch 141 partially released from struts. FIG. 9D illustrates handle 140 and latch 141 completely released from struts 150, enabling halo 134 to be removed from struts 150.

In an embodiment, halo 134 can be removed and replaced with a halo of a different shape or size to accommodate a user of a different shape or size. In an embodiment, halo 134 can be of substantially torus shape, to enable minimum contact with sleds 125. In another embodiment, halo 134 can further be shaped similar to a torus, where a minor circle of a torus can be an ellipse or any other shape to enable minimum contact with sleds 125. In another embodiment, halo 134 can be interchanged with a myriad of halos with different circumferences in order to accommodate users of all sizes. In another embodiment, struts 150 can further be enabled for removal in order to accompany different halo designs to accommodate users of all sizes. In another embodiment, removable halo 134 and removable struts 150 can aid in transporting an omnidirectional locomotion system.

Figure 10:
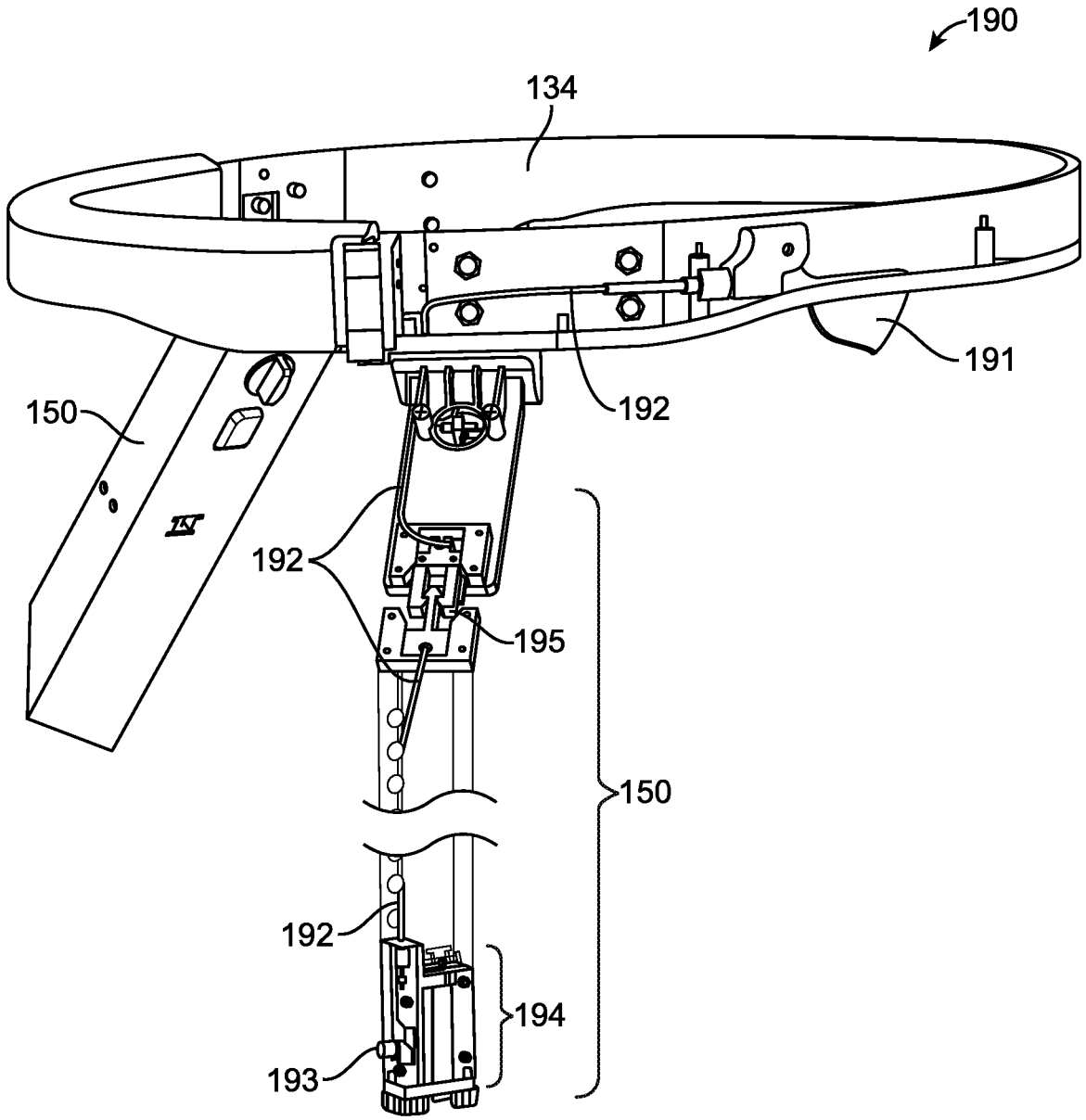
FIG. 10 illustrates an example strut system of an example omnidirectional locomotion platform system, in accordance with an example embodiment of the present disclosure.

FIG. 10 illustrates an example strut system 190 for vertical movement of halo 134. Halo 134 can comprise one or more release members 191 and be coupled to one or more struts 150. One or more struts 150 can comprise one or more locking mechanism 195 and one or more positioning member 194 coupled to the one or more release members 191 by one or more cables 192. The positioning member 194 can comprise retractable locking pin 193, the retractable locking pin 193 being engaged when the release member 191 is disengaged, disabling halo 134 from vertical movement; and the retractable locking pin 193 being disengaged when the release member 191 is engaged, enabling the halo 134 to move vertically. In an embodiment, struts 150 can be kept in place by a positioning pin or retractable locking pin 193 included in positioning member 194, which can lock the vertical location of the struts 150. Struts 150 can be moved vertically up and down when the positioning pin is retracted. A user can enable vertical movement by actuating release member 191. By actuating release member 191, cable 192 is pulled upwards actuating locking mechanism 195, which in return retracts the pin in the positioning mechanism 194 and unlocks struts 150 enabling vertical movement.

Figure 11:
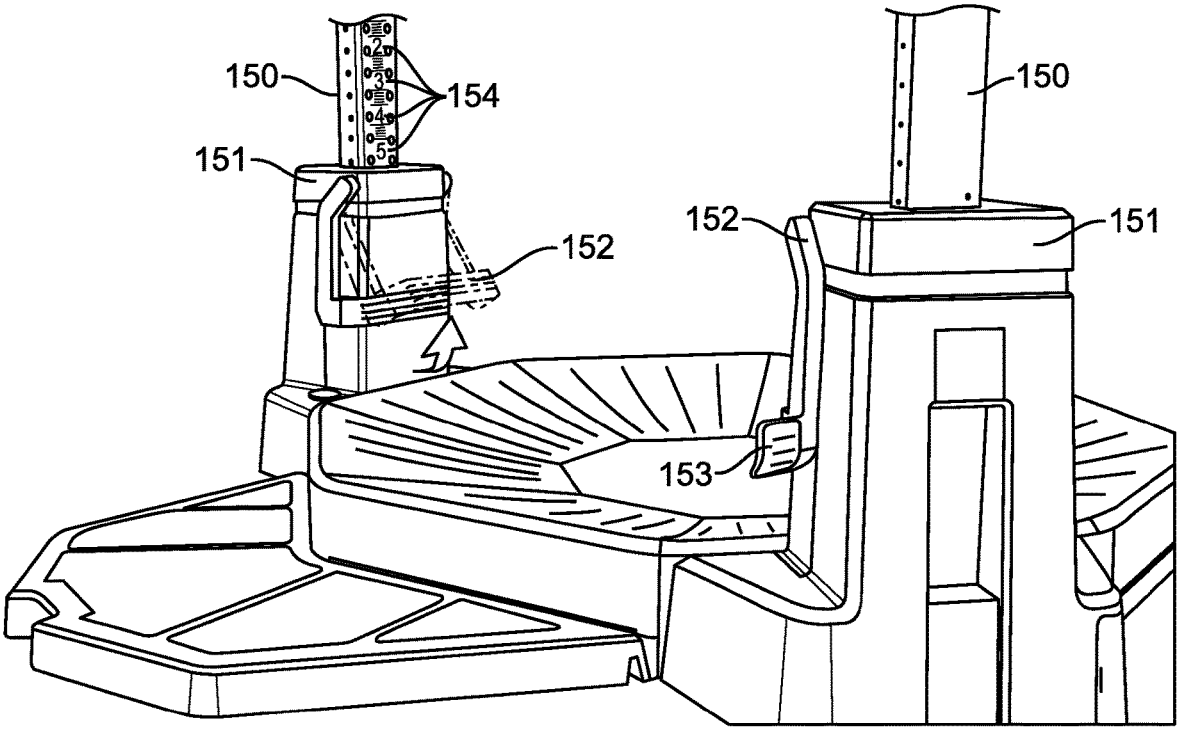
FIG. 11 illustrates an example strut support and release system, in accordance with an example embodiment of the present technology.
Figure 12A:
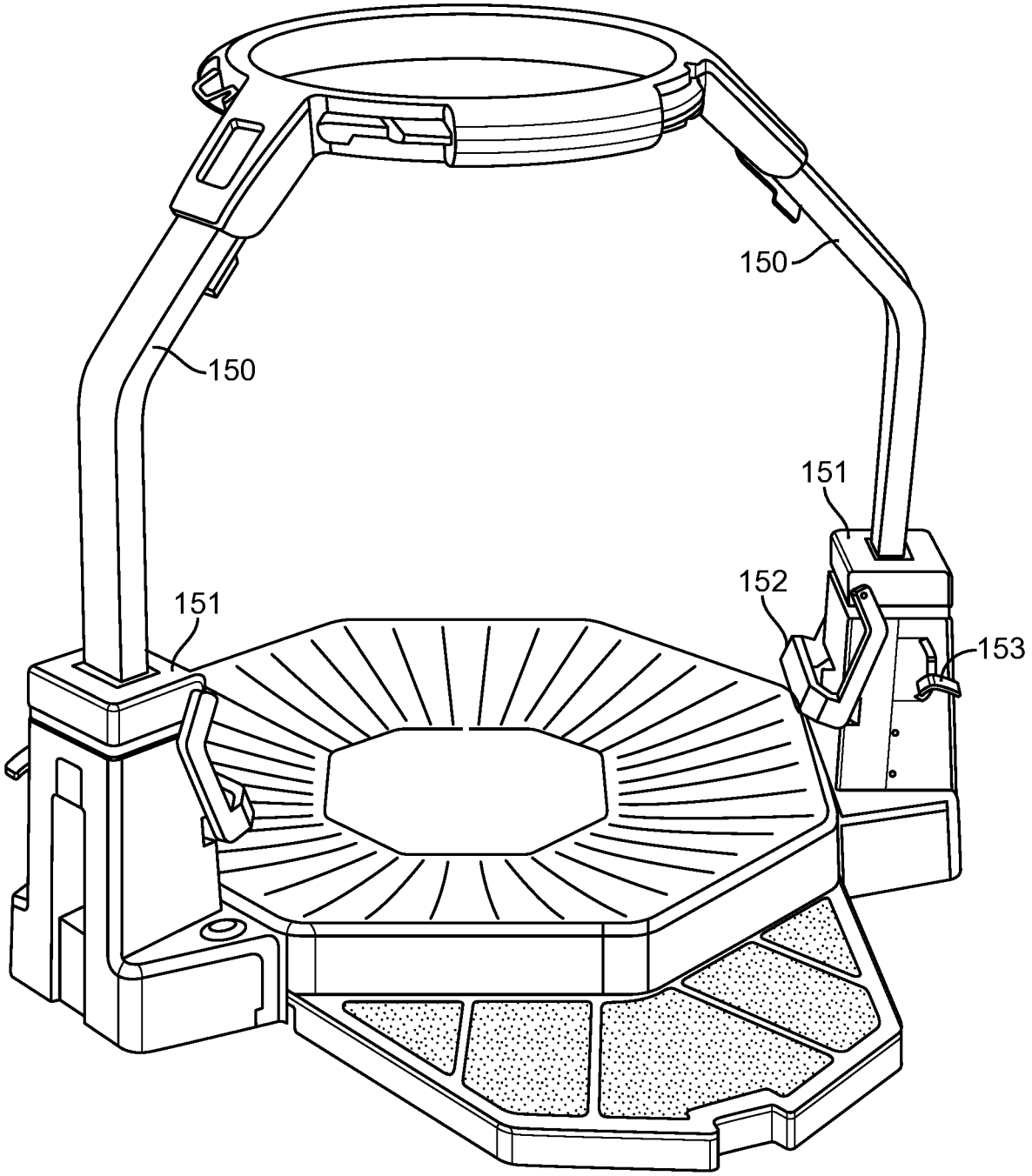
FIG. 12A and FIG. 12B illustrate an example strut support at a high vertical level and low vertical level, respectively, in accordance with an example embodiment of the present technology.
Figure 12B:
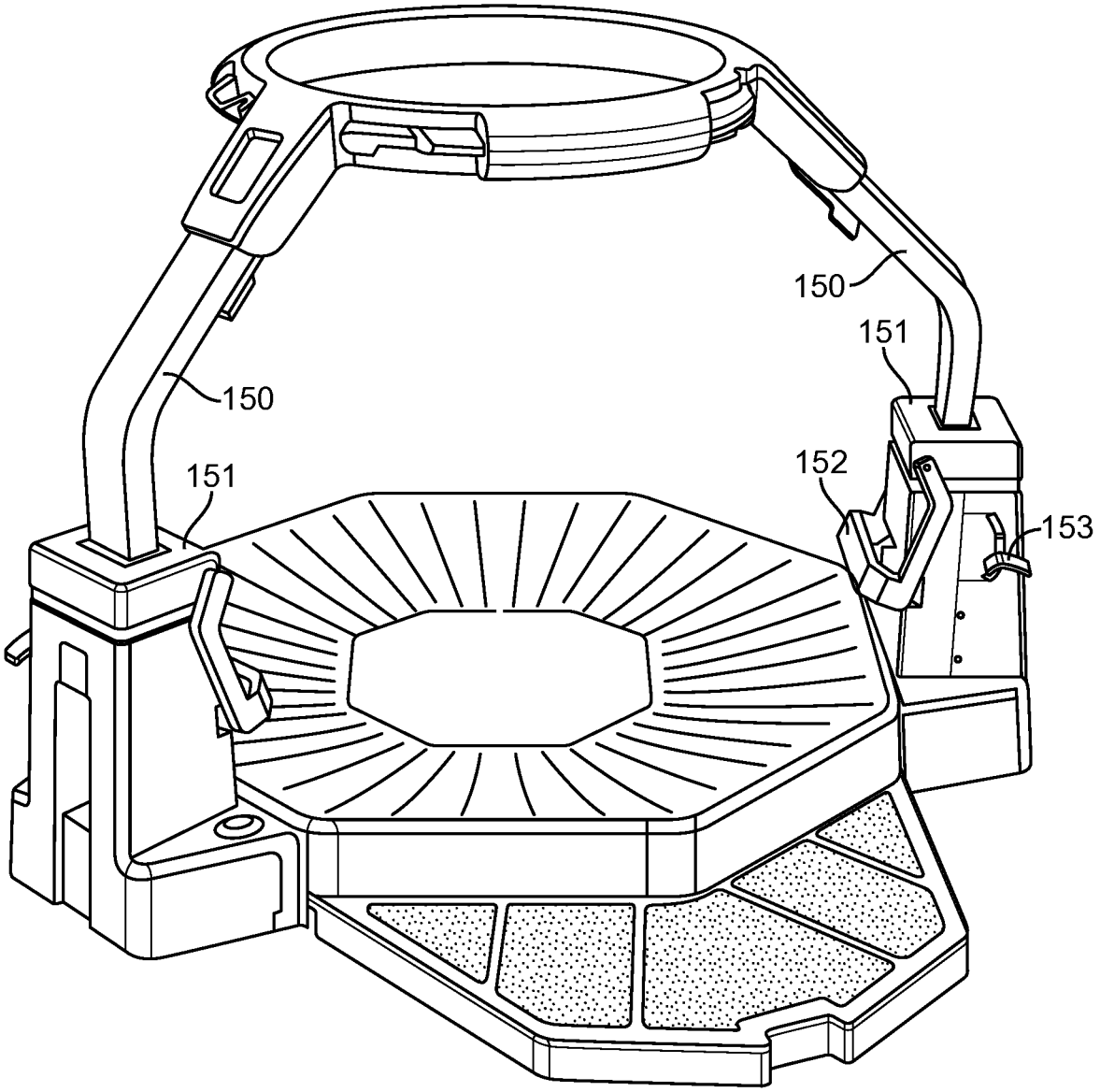
Figure 14:
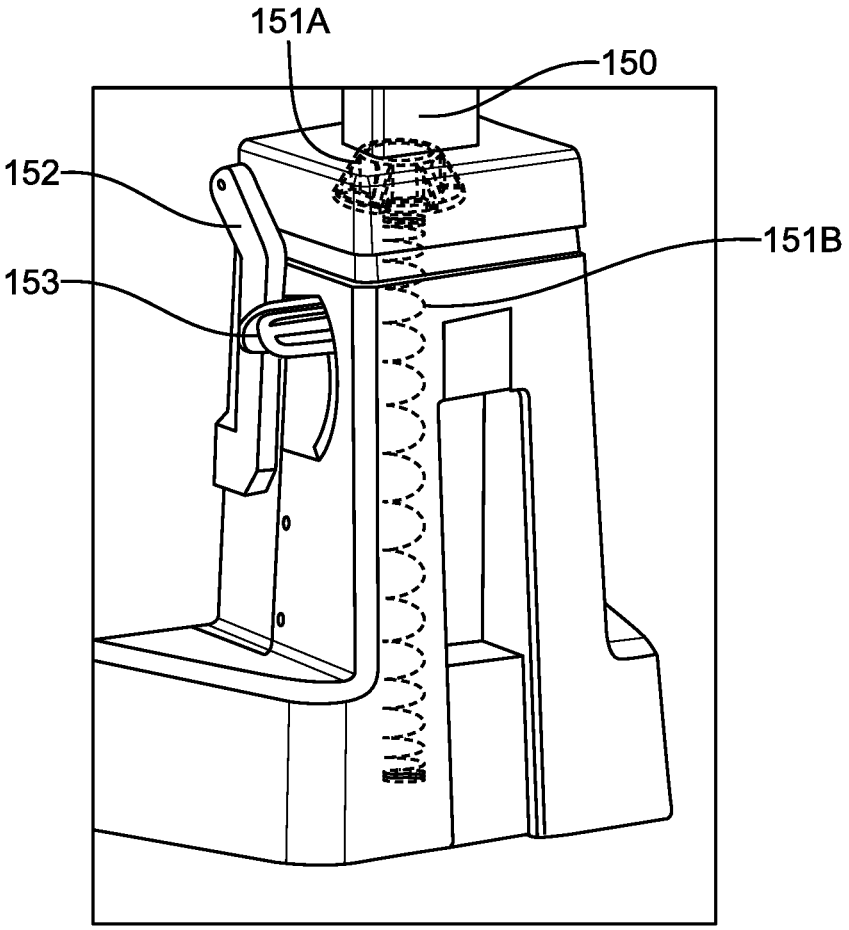
FIG. 14 is a cross-sectional view illustrating an example strut support and release system, in accordance with an example embodiment of the present technology.

FIG. 11 illustrates an example omnidirectional locomotion system 130 with vertically adjustable struts 150. Foot levers 153 can be configured to release strut latches 152 to enable adjustment or removal of strut 150 from strut base 151. Foot levers 153 can be attached to strut latches 152. In another embodiment, foot levers 153 can be separate from strut latches 152 as shown in FIG. 14. Separate foot levers can utilize an internal spring released mechanism for releasing strut latches 152. Struts 150 can include printed height markings 154 for aiding in height adjustments. Struts 150 can be completely removed from strut base 151 with the use of an auto-lock mechanism shown in FIG. 18-20. FIG. 12A and FIG. 12B illustrate struts 150 at a high height and a low height respectively.

Figure 13:
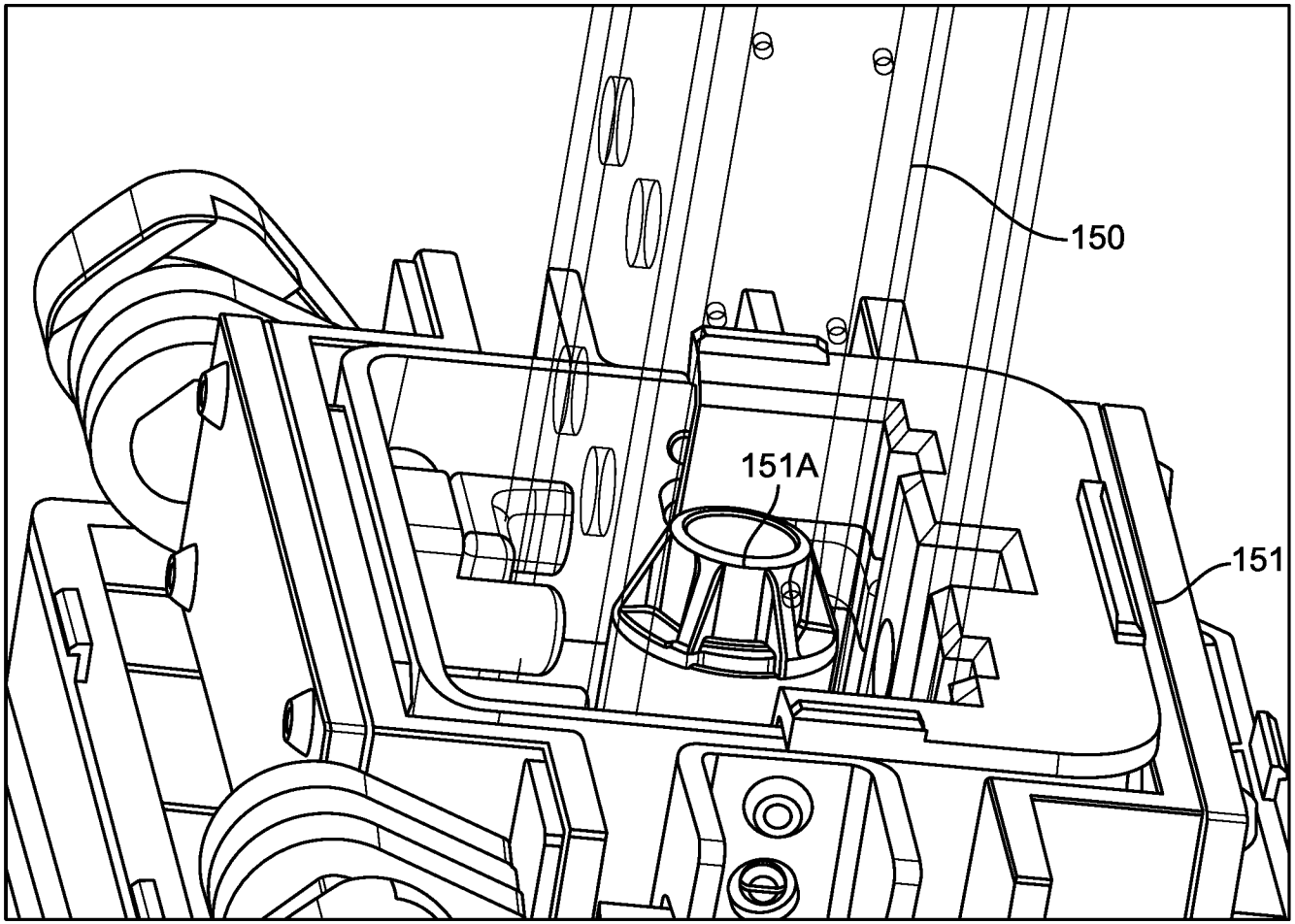
FIG. 13 is a cross-sectional view illustrating an example strut and strut base, in accordance with an example embodiment of the present technology.

FIG. 13 is an internal view of an example strut base 151 and strut 150 illustrating a strut connection mechanism. Circular portion 151a supports a spring (not shown) that can provide a counterforce to the inner portion of strut 150. The counterforce of the spring prevents struts 150 from falling when unlatched by strut latch 152 from strut base 151. FIG. 14 is an internal view of an example strut base 151 illustrating an internal spring mechanism 151B. When foot lever 153 is depressed and struts 150 are released, internal spring mechanism 151B is actuated providing an upward force to counteract the weight of struts 150 and halo 134. Internal spring mechanism 151B can enable a user to easily adjust the height of halo 134 without having to bear the entire weight of the struts 150 and halo 134.

Figure 15:
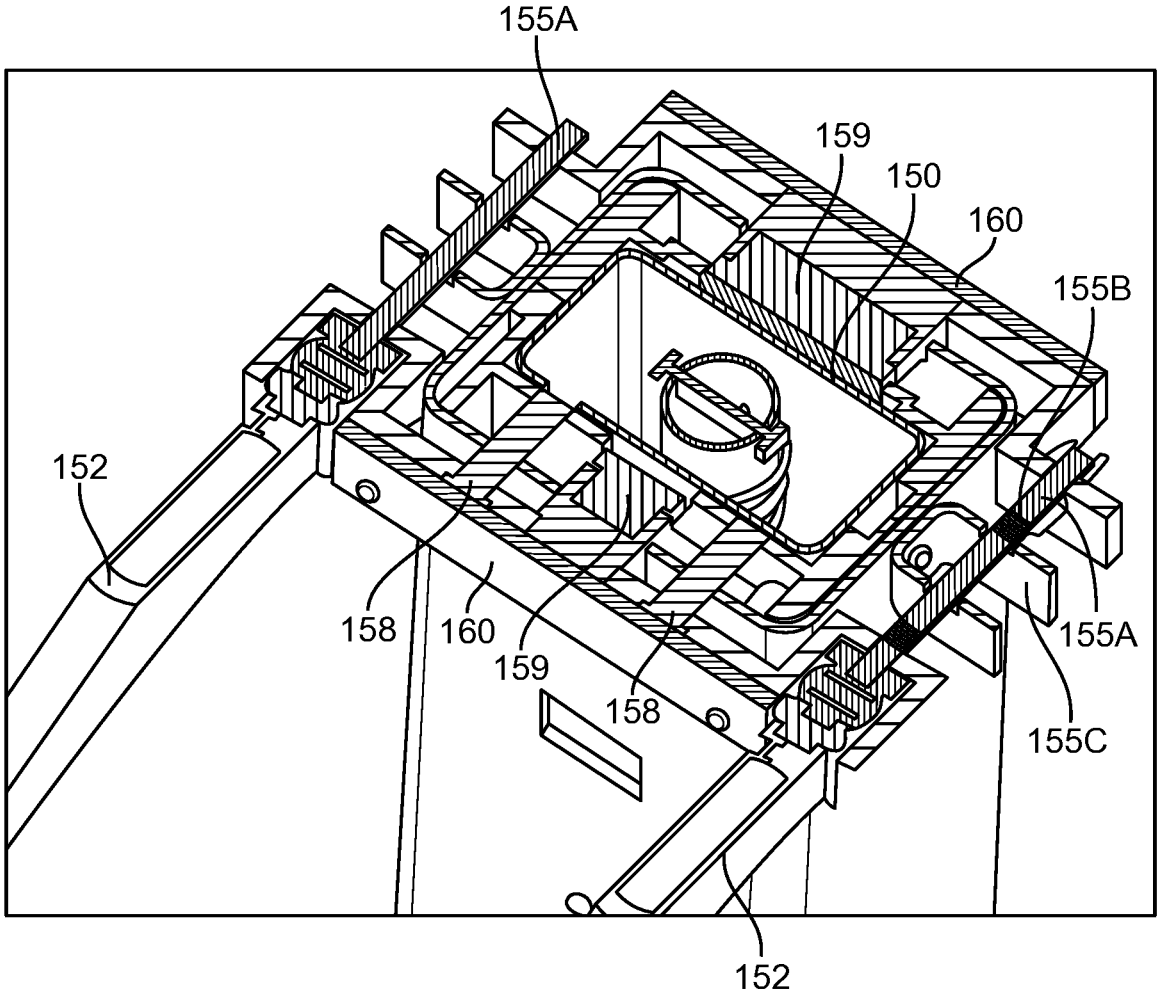
FIG. 15 is a cross-sectional view illustrating an example strut release system, in accordance with an example embodiment of the present technology.

FIG. 15 is a cross-sectional view of an example strut latch 152. Strut latch 152 can be coupled to pins 155A, springs 155B and brackets 155C. Pins 155A can be threaded through brackets 155C and springs 155B can be circumferential to pins 155A and adjacent to each side of brackets 155C. When strut latch 152 is released there is minimal tension in springs 155B enabling strut 150 to be vertically adjusted. When strut latch 152 is engaged, tension is present in springs 155B disabling or locking strut 150 from being vertically adjusted. Secure pins 158 can be connected to strut latch 152 by a mounting plate 160. Secure pins 158 can be engaged when strut latch 152 is engaged (flush with strut base 151) and disengaged when strut latch 152 is disengaged (away from strut base 151). Secure pins 158 can align with strut holes (shown in FIG. 11) enabling securement of struts 150 in strut base 151. Secure pins 158 can aid in engagement of struts 150 at level heights. Rubber pads 159 can be connected to strut latch 152 by a mounting plate. Rubber pads 159 can be engaged when strut latch 152 is engaged (flush with strut base 151) and disengaged when strut latch 152 is disengaged (away from strut base 151). Rubber pads 159 can create friction between the strut base 151 and strut 150 enabling preventing movement of struts 150.

Figure 16:
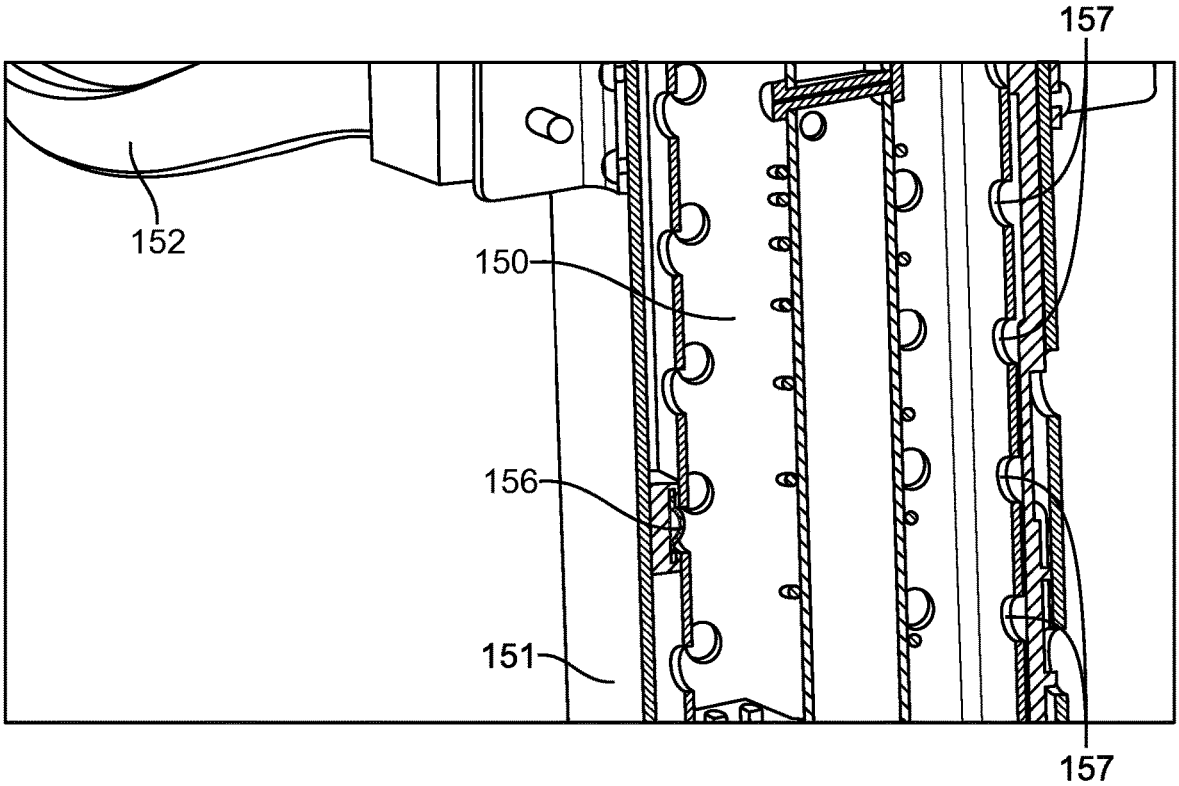
FIG. 16 is a cross-sectional view illustrating an example strut and strut base, in accordance with an example embodiment of the present technology.

FIG. 16 is a cross-sectional view of an example strut 150 illustrating a peg adjustment mechanism. Strut base 151 can include one or more pegs 156 enabled to interact with struts 150. Strut 150 can include one or more peg holes 157 for coupling with one or more pegs 156. Pegs 156 and peg holes 157 can provide a tactile feedback to a user while adjusting the height of halo 134. For example, when a user is adjusting the height of halo 134, by pulling or pushing on the handle 131, peg 156 and peg holes 157 can provide an audible clicking sound and a physical clicking vibration to notify the user that strut 150 is aligned correctly.

Figure 17:
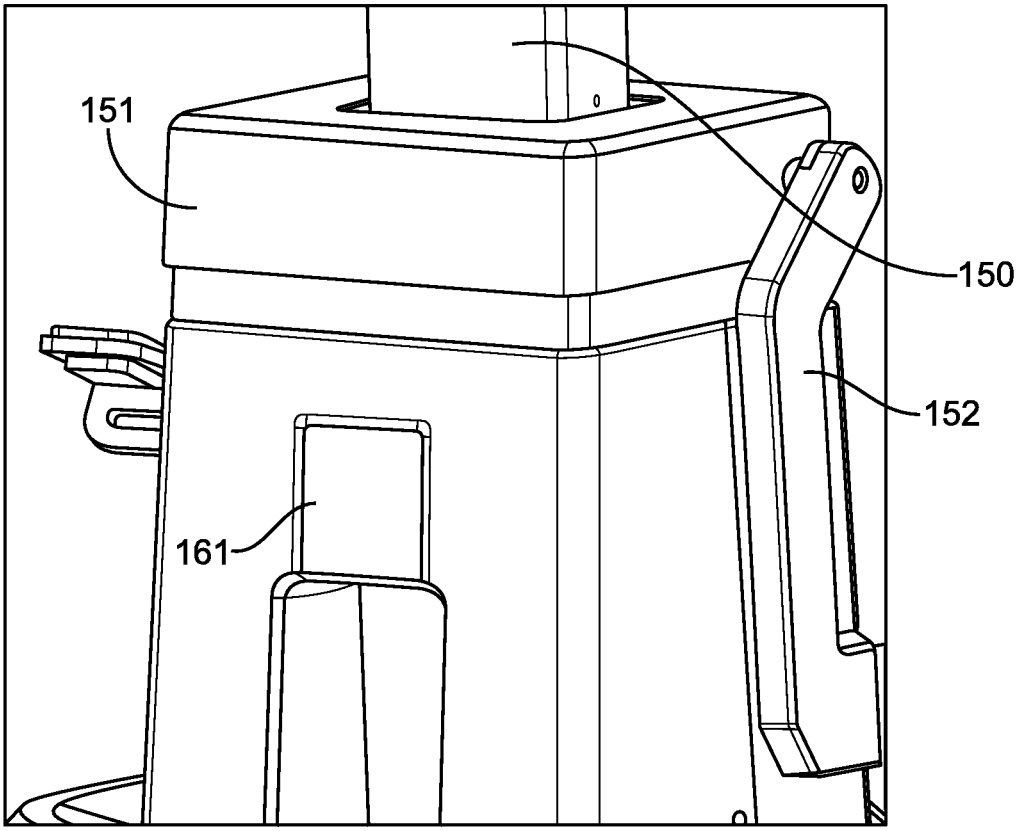
FIG. 17 illustrates an example auto-lock panel of an example auto-lock system of a strut support and release system, in accordance with an example embodiment of the present technology.
Figure 18:
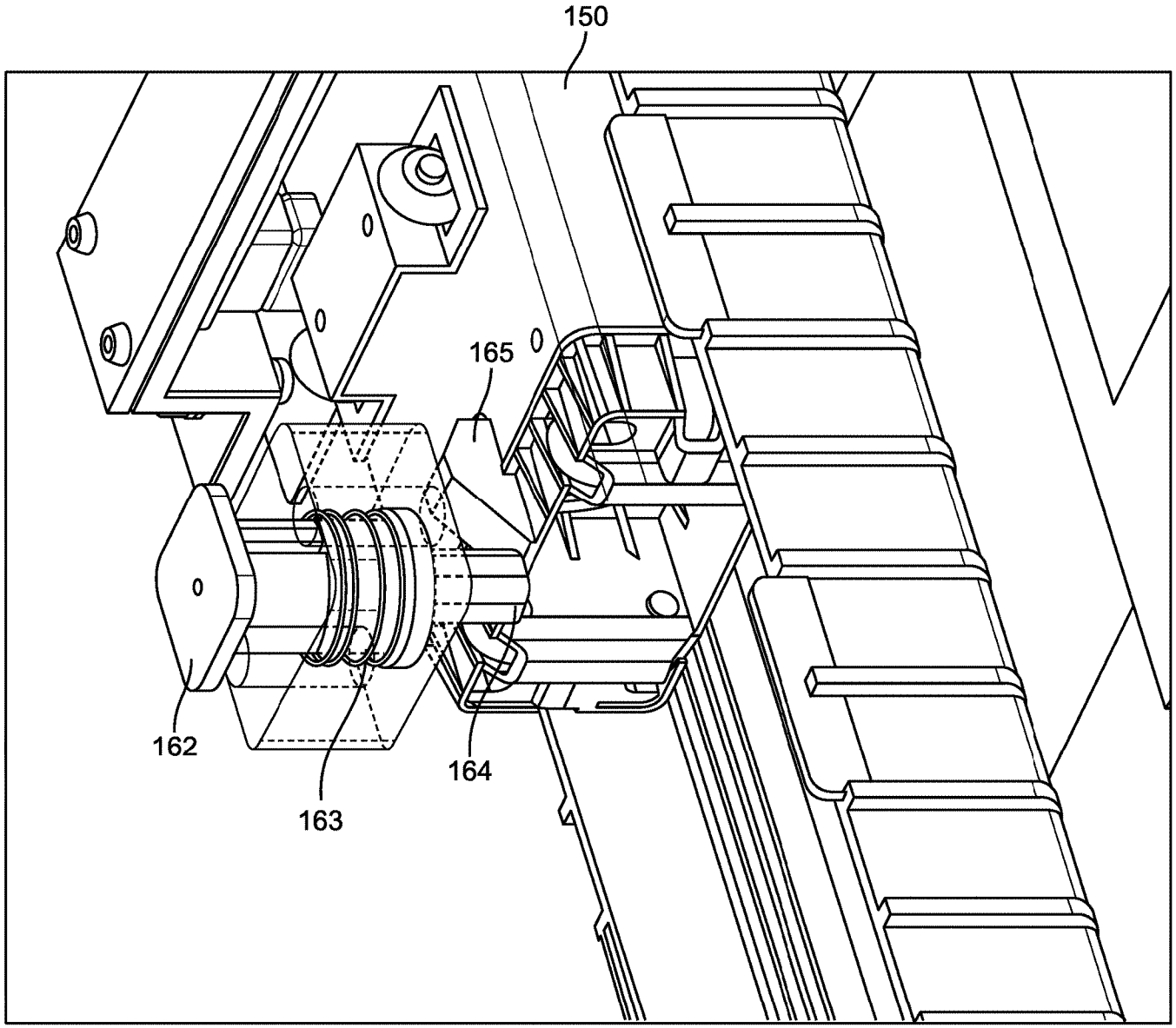
FIG. 18 is an internal view illustrating an example auto-lock system, in accordance with an example embodiment of the present technology.
Figure 19:
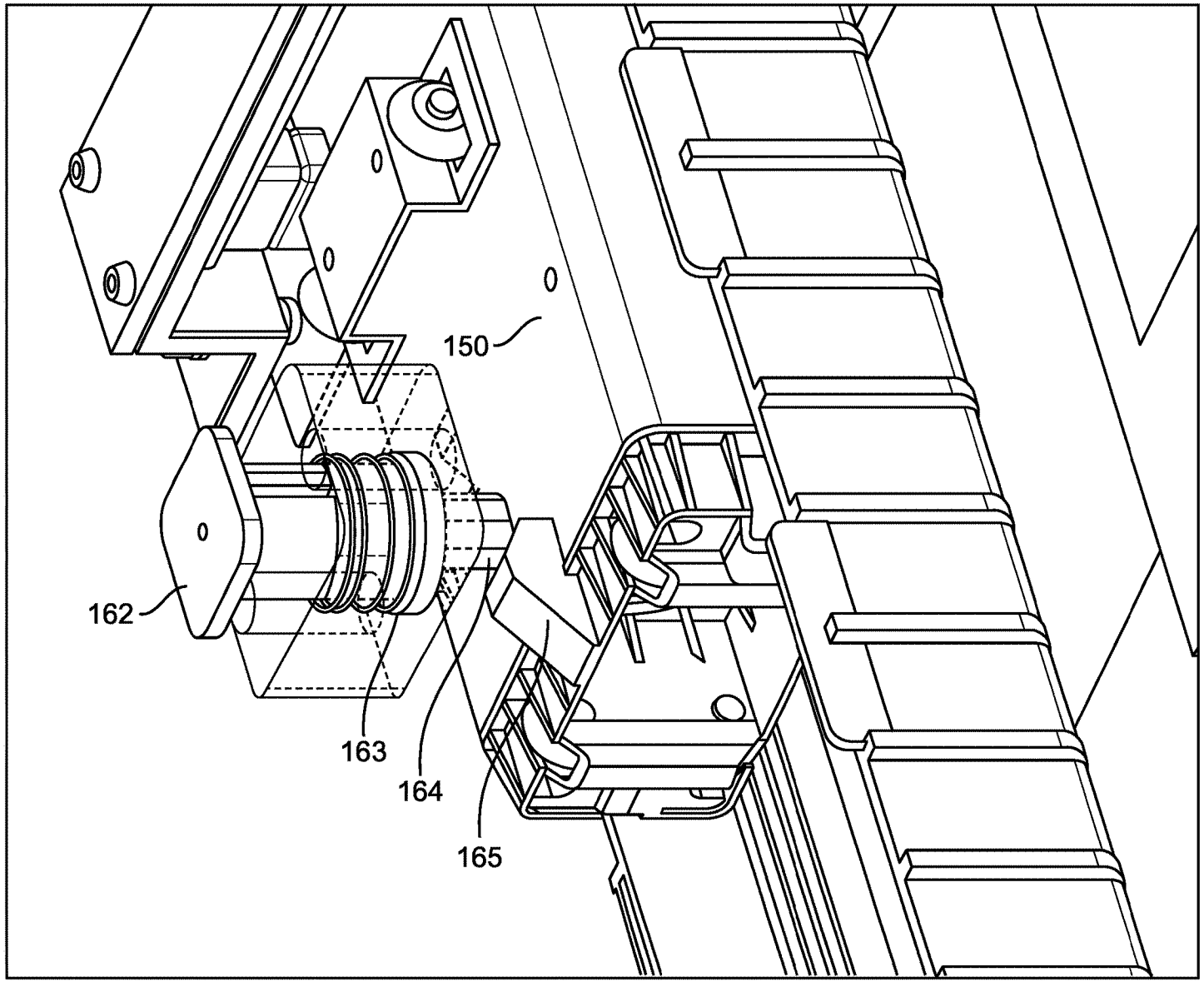
FIG. 19 is an internal view illustrating an example auto-lock system, in accordance with an example embodiment of the present technology.
Figure 20:
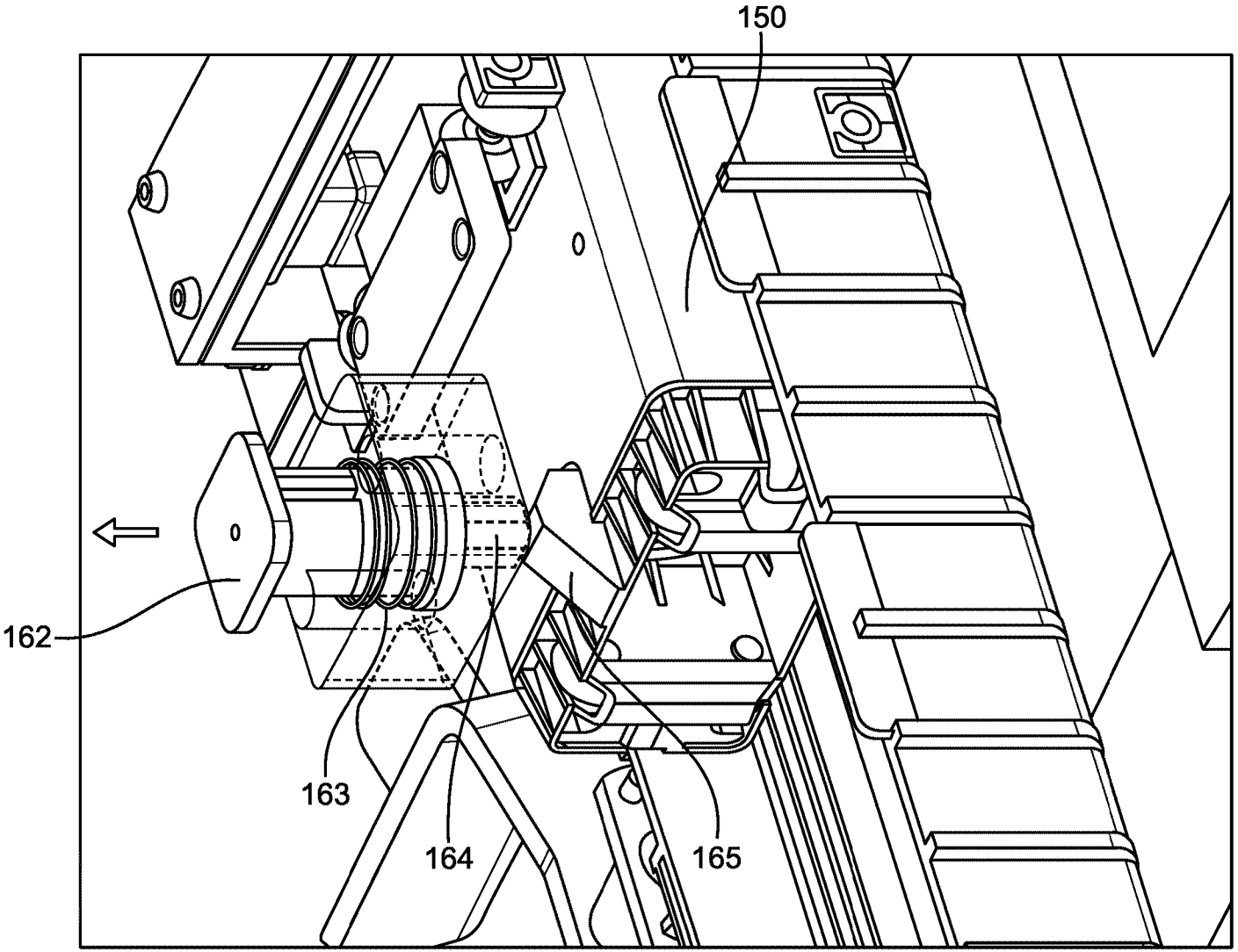
FIG. 20 is an internal view illustrating an example auto-lock system, in accordance with an example embodiment of the present technology.

FIG. 17 illustrates an example removable panel 161 of an auto-lock mechanism of strut base 151. FIG. 18, FIG. 19 and FIG. 20 illustrate internal structures of an example strut base 151 illustrating an auto-lock mechanism in various stages of engagement. FIG. 18 illustrates strut 150 before complete insertion into a strut base 151. Auto-lock pin 164 can be coupled to spring mechanism 163 and handle 162. Engaging (pulling) handle 162 can compress spring mechanism 163 partial removing pin 164. Strut 150 can include slanted depressible button 165. Slanted depressible button 165 can enable strut 150 to be inserted into strut base 151 and prevent the removal of strut 150 without engagement of auto-lock mechanism. FIG. 19 illustrates strut 150 inserted into strut base and an enabled an auto-lock mechanism. During this stage of engagement, strut 150 cannot be removed from strut base 151. FIG. 20 illustrates engaging handle 162, compressing spring mechanism 163, partial removing pin 164 and enabling the removal of strut 150.

Figure 21:
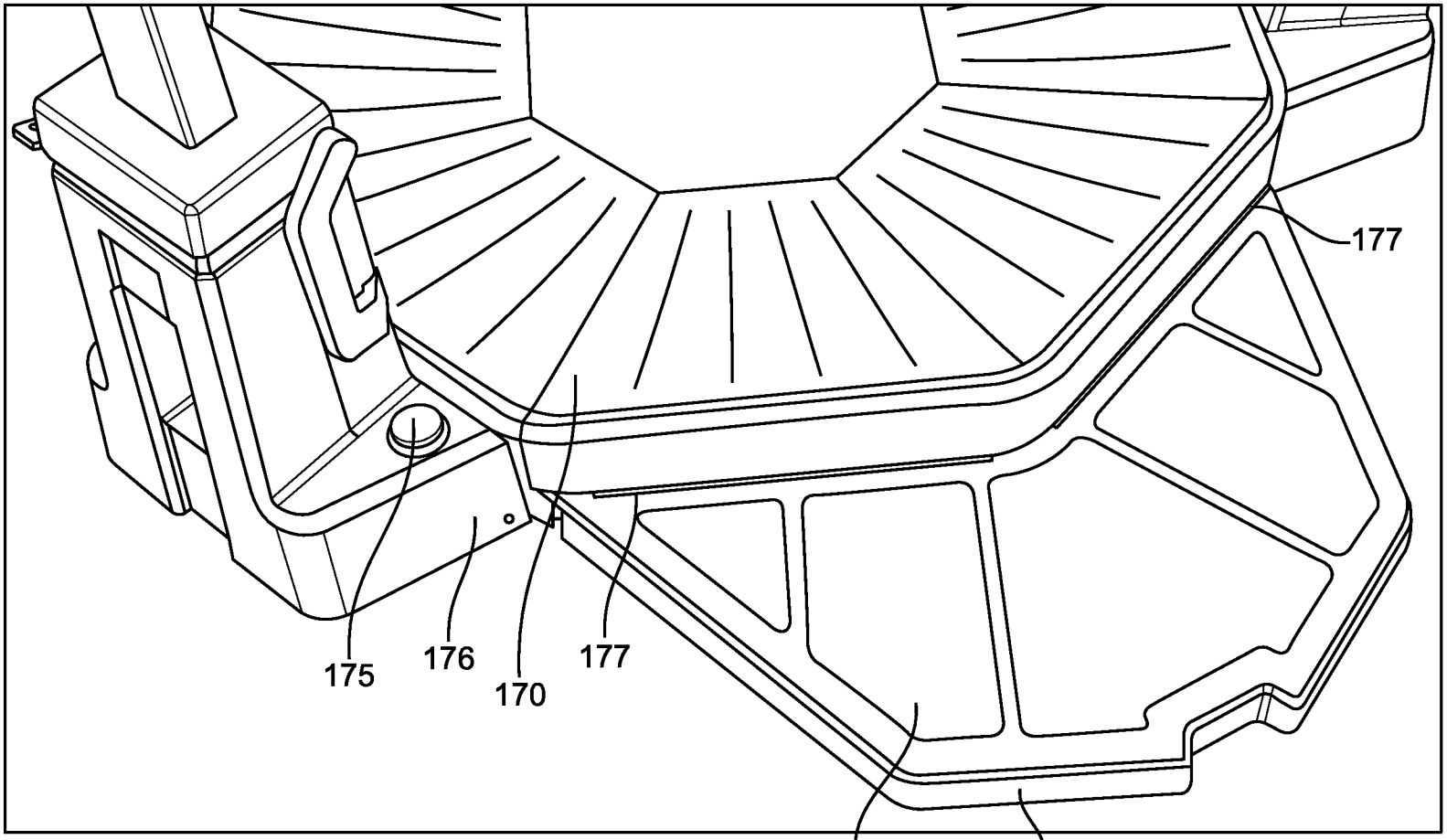
FIG. 21 illustrates an example platform, lower platform and cable management system of an example omnidirectional locomotion system, in accordance with an example embodiment of the present technology.

FIG. 21 illustrates an example omnidirectional locomotion system, specifically, a platform 170 and a lower platform 171. Lower platform 171 can provide added stability to an omnidirectional locomotion system. As shown in FIG. 7, an omnidirectional locomotion system can include two offset (not centered) struts 150. Lower platform 171 can provide added stability by counter-weighting the offset of the struts. Lower platform 171 can include textured anti-slip rubber pad 174 to prevent a user from slipping/falling while wearing low friction footwear. Lower platform 171 can also include a disclaimer informing a user to remove footwear to prevent accidents while operating in or around an omnidirectional locomotion system. Platform 170 and lower platform 171 can also include light-emitting diodes (LED) 177 to inform a user of the different statuses of an omnidirectional locomotion system. For example, green can indicate fully operational, in operation or sensors connected, amber can indicate please wait or sensors not connected, red can indicate stop, system is not ready or sensors not connected. Various blinking LED and combinations thereof can be configured for other status notifications. The omnidirectional locomotion system can also include an on/off button 175. Pressing the on/off button can power on or off a PCB, LED, and enable connections or can disconnect with one or more sensors and computing system.

Figure 22:
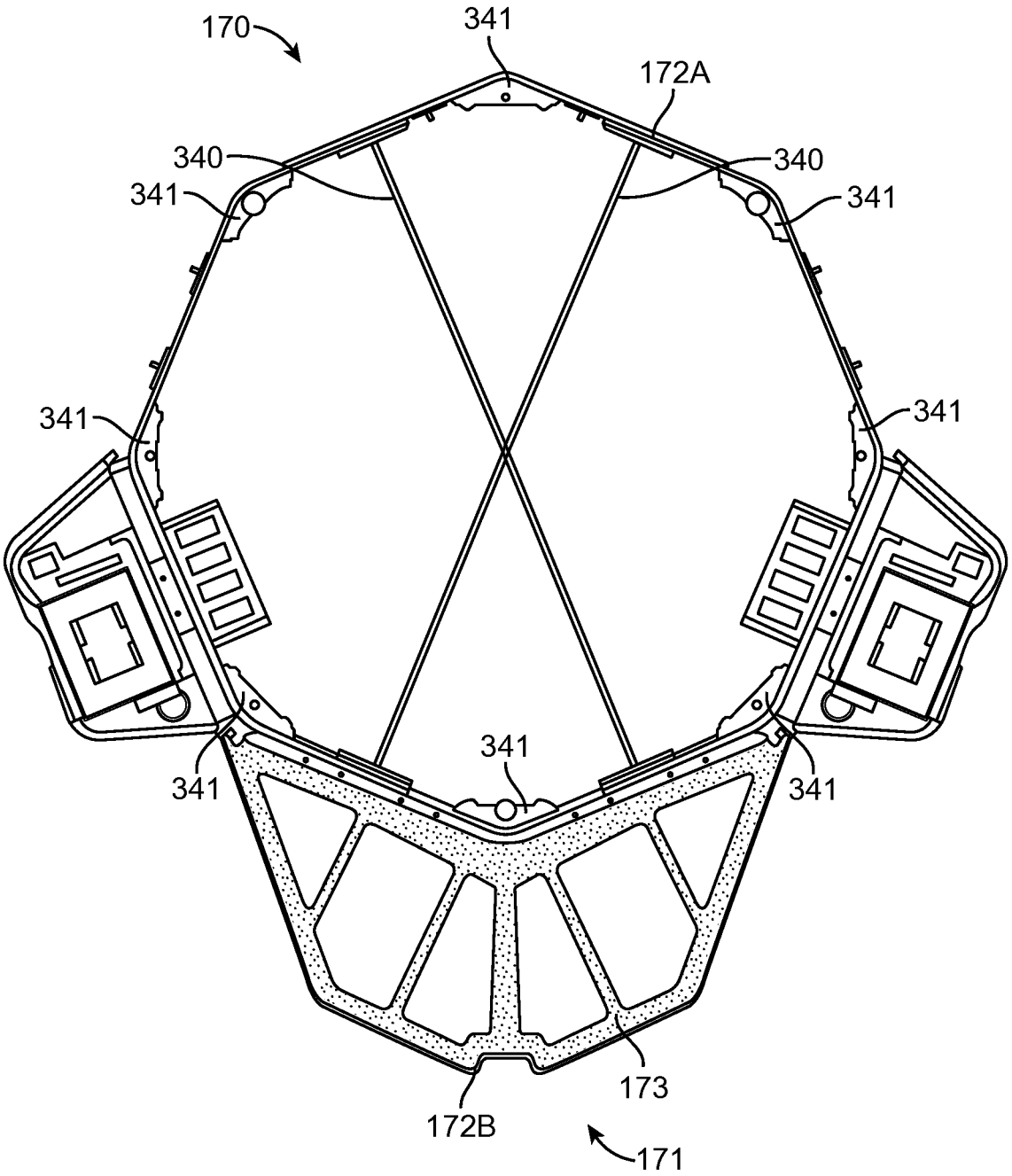
FIG. 22 illustrates a top cross-sectional view of an example support structure of an example platform and lower platform of an omnidirectional locomotion system, in accordance with an example embodiment of the present technology.

FIG. 22 illustrates an example internal structure of a platform 170 and lower platform 171 of an omnidirectional locomotion system. Platform 170 enables stable use of an omnidirectional locomotion system comprising two offset struts. Platform 170 can include an outer frame 172A and two crossbars 340 for enabling stability. Platform 170 can further include support plates 341 in each corner of platform 170. In an embodiment, crossbars 340 and support plates 341 can be welded to platform 170. Crossbars 340 and support plates 341 can be comprised of metals, metal-alloys, for example, steel or any other material capable of stabilizing the use of an omnidirectional locomotion system. Platform 170 can be of a plurality of shapes, for example a hexagon, an octagon, a square or a circle. Lower platform 171 can include an outer frame 172B and an internal frame 173. The internal frame 173 can be made of a heavy material, for example steel, in order to counter-weight the user's weight and the offset of the struts.

Figure 23:
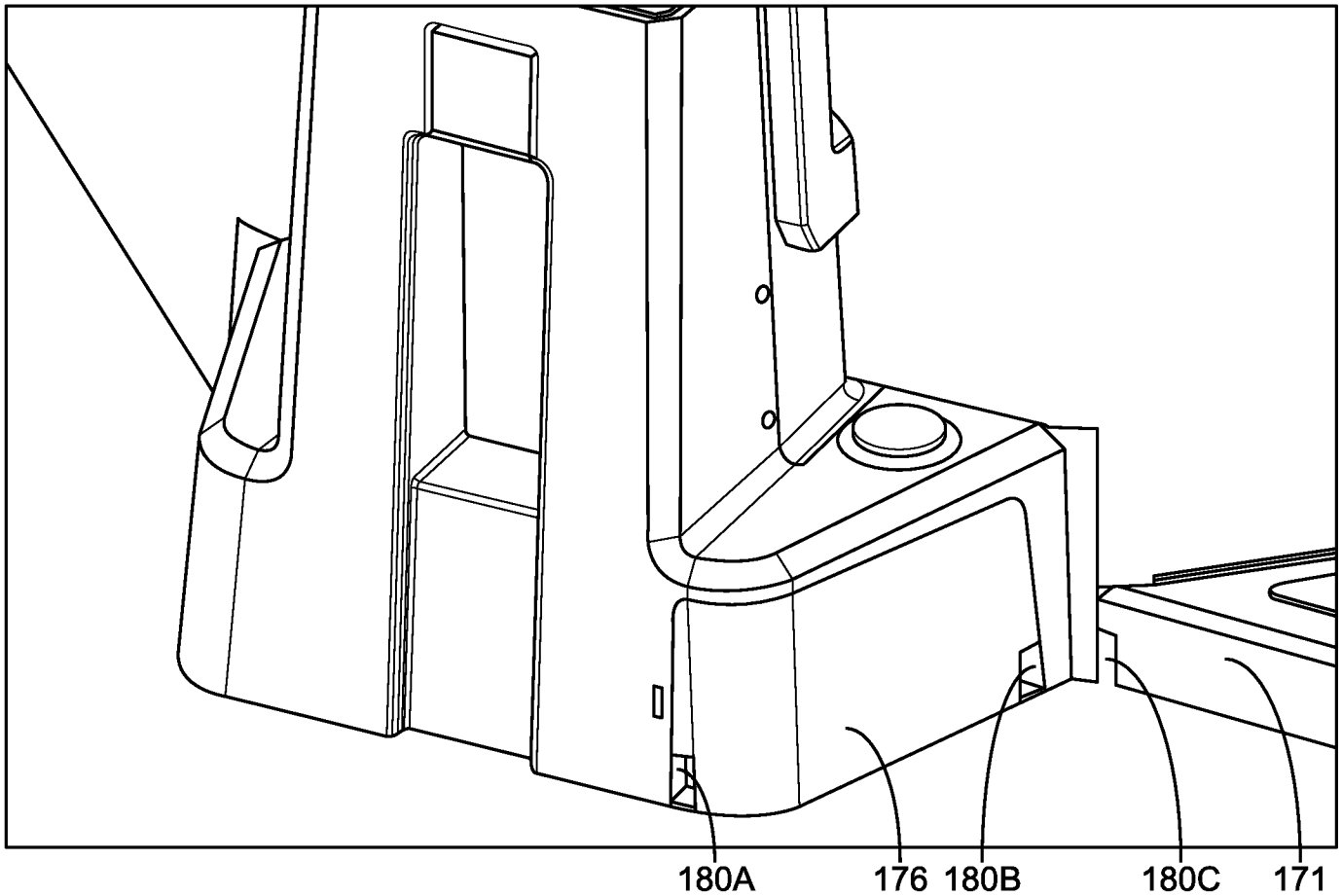
FIG. 23 illustrates an example cabling system, in accordance with an example embodiment of the present technology.
Figure 24:
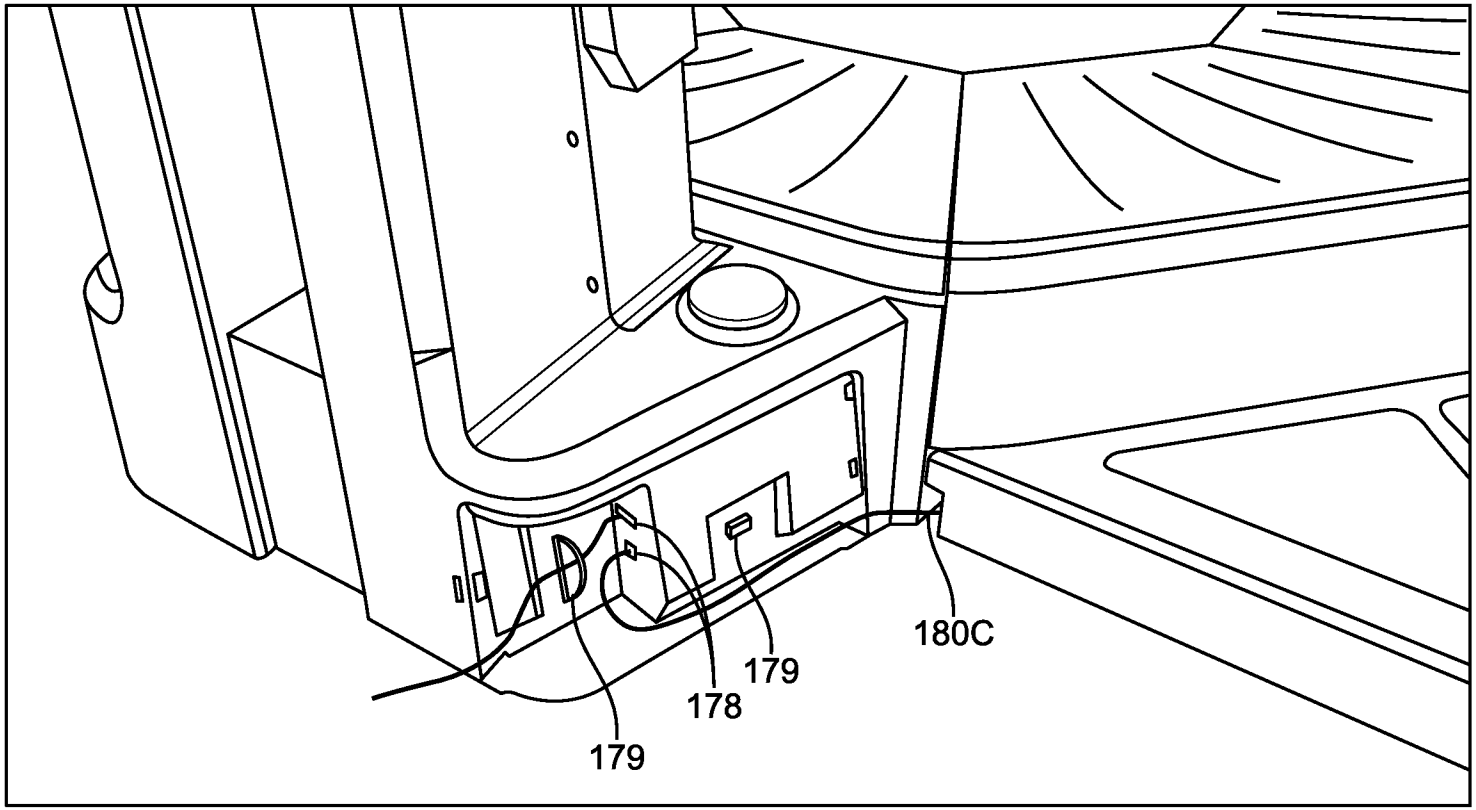
FIG. 24 illustrates an example cabling system, in accordance with an example embodiment of the present technology.

FIG. 23 illustrates an example cable/PCB panel of an omnidirectional locomotion system. Panel 176 protects the cables and PCB from external elements. Cut-outs 180a, 180b, and 180c can enable cables from the PCB to be run from either side of the panel and under the lower platform. Cut-outs 180a, 180b, and 180c can enable cable connections from either side of the omnidirectional locomotion system preventing possible cabling issues. For example, preventing loose cables being run in walking areas, trip hazards, accidental unplugs, or unsafe cabling layouts. FIG. 24 illustrates an example internal cabling/PCB panel of an omnidirectional locomotion system. One or more cable plugs 178 can be included for inserting cables of computer system for connection with PCB, power cables, network cables, or any other type of connection cables. Clips 179 can aid in cable management by preventing cables from moving around behind panel 176. Alternatively, clips 179 could be cable plugs. In another embodiment, cable plugs 178 can each have an integrated clip 179. Cable plugs 178 and clips 179 can include cables that run under lower platform 171 by cut-out 180c. In another embodiment, platform 170 and lower platform 171 can be integrated with cable runs to facilitate cables being hidden on opposite sides. The PCB can be located behind cable plugs 178 and clips 179. The PCB can be removable to upgrade or install new hardware.

Figure 25:
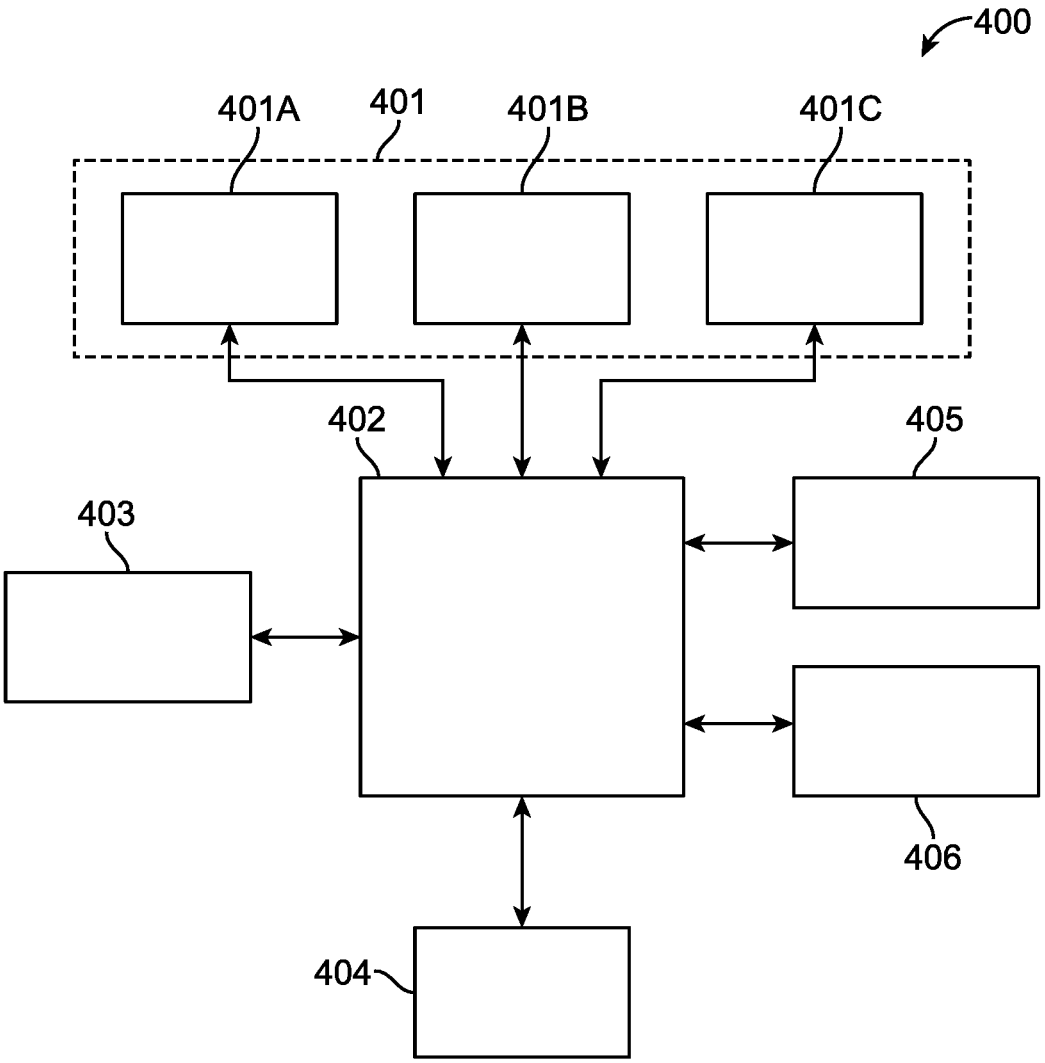
FIG. 25 is a block diagram illustrating an example POD system, in accordance with an example embodiment of the present technology.

FIG. 25 is a block diagram illustrating an example POD system 400. In an embodiment, POD system 400 can be connected to a user's body, an accessory or an omnidirectional locomotion system (for example, legs, feet, arms, head, torso, gun, sword, paddle, racquet, halo, or harness) to enable data related to a user's movements to be transmitted to a computing system (for example, an aggregator board). In an embodiment, a sensor 401 can include an accelerometer 401A, a gyroscope 401B, and a magnetometer 401C. In one embodiment, sensor 401 can include one or more inertial measurement units (IMU). One or more sensors 401 can digitize analog signals for a multi-axis compass, accelerometer and gyroscope. One or more sensors 401 can connect to a multi-controller unit (MCU) 402. In an embodiment, the connection between sensor 401 and MCU 402 is by an I2C bus. In an embodiment, the connection between sensor 401 and MCU 402 is by an USB. MCU 402 can manipulate received data from one or more IMU 401 into a multi-axis solution indicating direction, position, orientation and movement and then transmits the data to another computing system by radio transmitter 404. In an embodiment, radio 404 is a short-range wireless radio (for example Bluetooth). In an embodiment, radio 404 is a 2.4 GHz wireless radio. MCU 402 can also have connections to a power management 405 (by πL), EERPOM 406 (by I2C), a UART 403 for debugging (by TTL).

Figure 26:
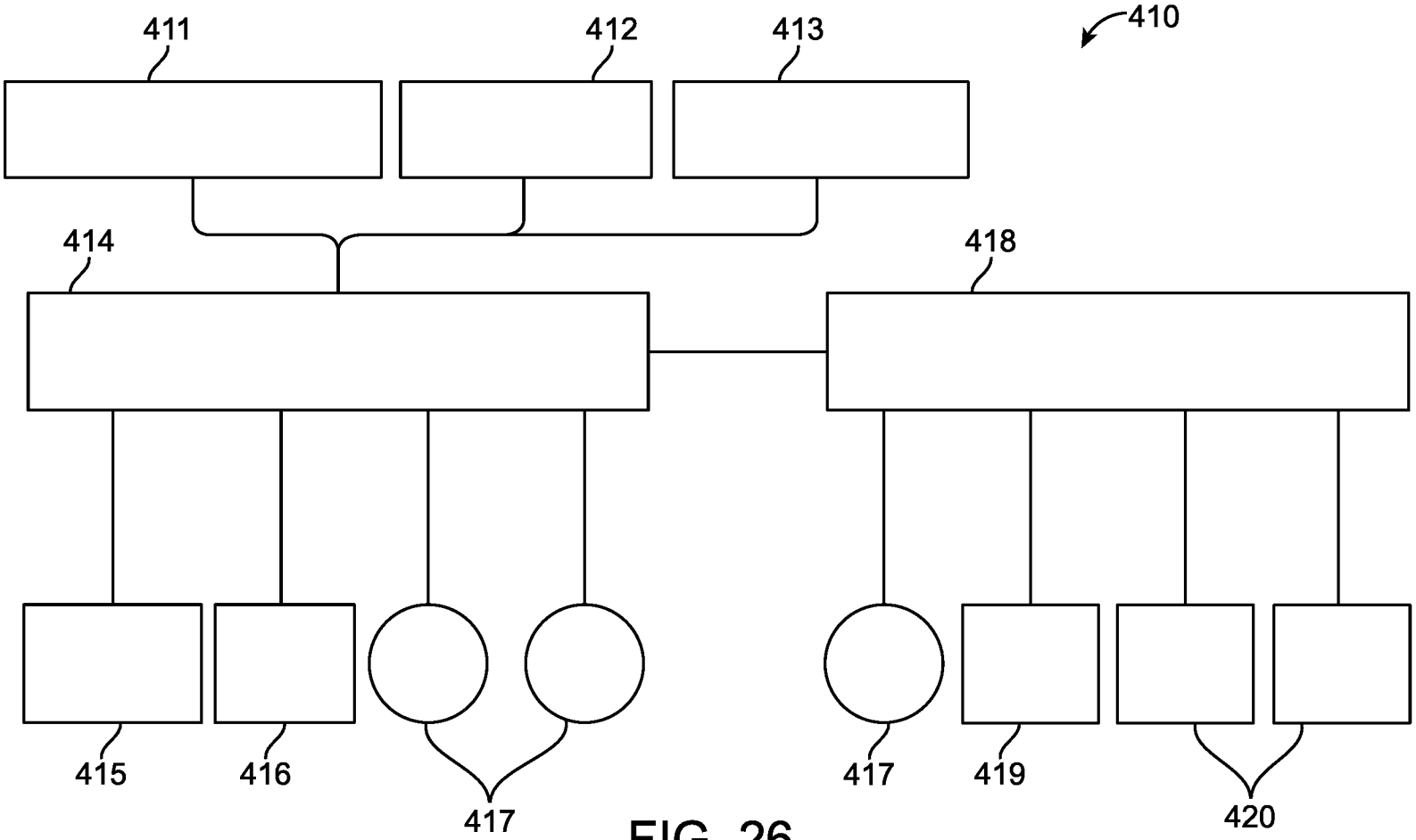
FIG. 26 is a block diagram illustrating an example POD system, in accordance with an example embodiment of the present technology.
Figure 27:
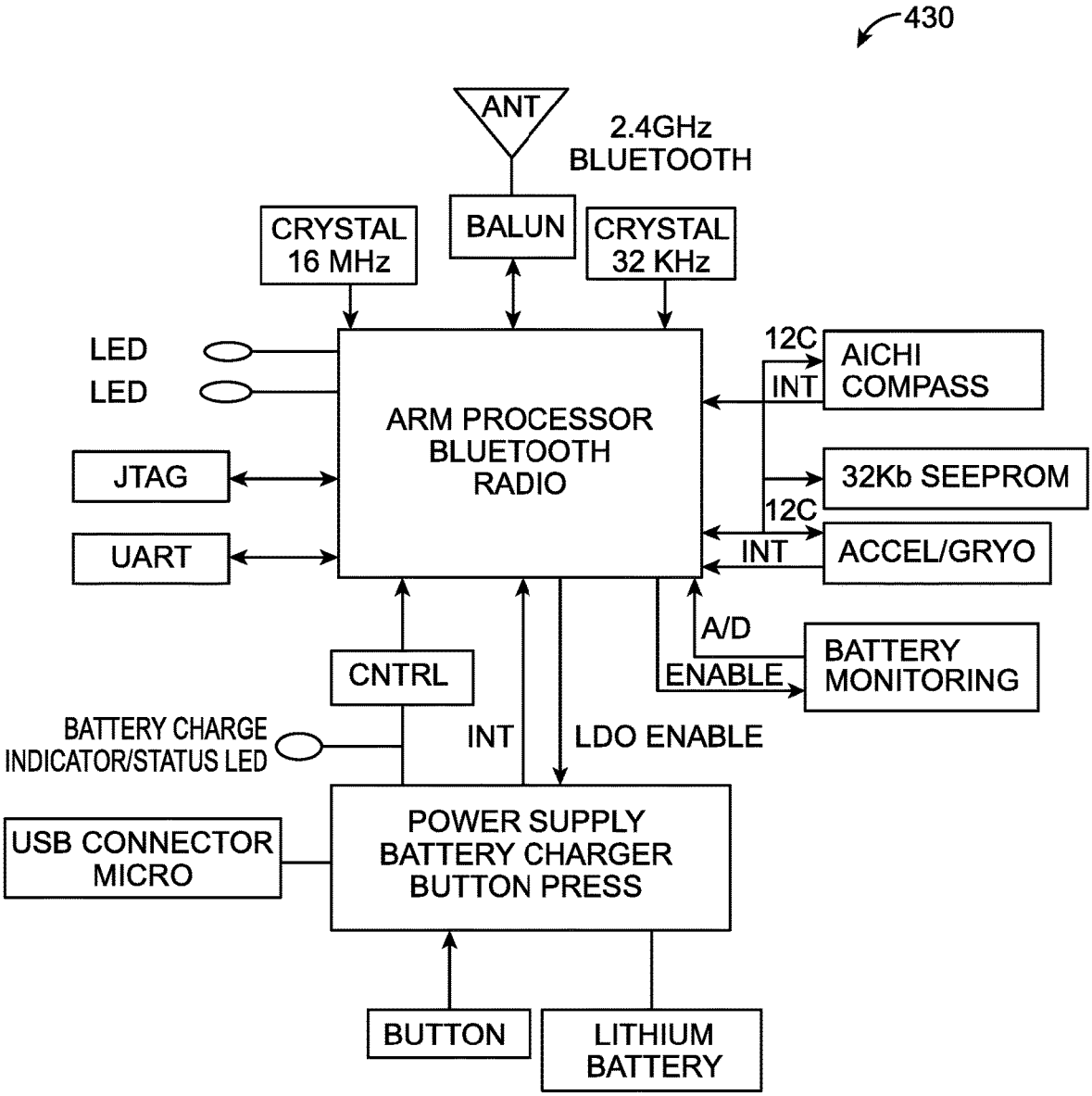
FIG. 27 is a block diagram illustrating an example POD system, in accordance with an example embodiment of the present technology.

FIG. 26 and FIG. 27 are block diagrams of example POD systems 410 and 430. POD 410 can include a multi-axis accelerometer/gyroscope 411, an magneto-impedance (MI) sensor 412 for detecting multi-axis magnetic fields, and an EEPROM memory 413 connected to a processor/wireless transceiver 414. In an embodiment the processor and wireless transceiver can be integrated. In another embodiment, the processor and wireless transceiver can be separated. Processor 414 can be connected to a radio interface 415, a TTL interface 416 and one or more LEDs 417 for indications of transmissions, statuses, and errors. Processor 414 can be connected to a power management chip 418. Power management chip 418 can be connected to a USB interface 419, one or more battery interfaces 420 and one or more LEDs 417 for indications of power management, transmissions, statuses, and errors. The various components of POD system 410 can be connected by I2C bus, RF, UART, GPO, USB power, battery power, PMIC, or GPI. For example, accelerometer/gyroscope 411 can be connected to processor 414 by I2C, processor 414 can be connected to radio interface 415 by RF, and power management chip 418 can be connected to battery interface by GPI. POD system 430, shown in FIG. 27, can represent an alternative embodiment of POD system 410.

A POD can be pre-configured for use, for example, a first POD can be designated for use as a left foot, a second POD can be designated for use with a right foot, a third POD can be designated for use with a torso, a fourth POD can be designated for use with a head, a fifth and sixth POD can be designated with a left and right arm/hand respectively, a seventh POD can be designated to be used with a head, and an eighth POD can be designated with an accessory, such as a gun or sword. Furthermore, more IMUs can be designated or less IMUs can be designated based on specific needs of a user computing system. Alternatively, an POD can be configured before use. For example, a computing system can ask a user to move their left foot to configure an POD on their left foot. The computing system can ask a user to move their right foot to configure an POD on their right foot. The computing system can ask a user for each present POD.

Figure 28:
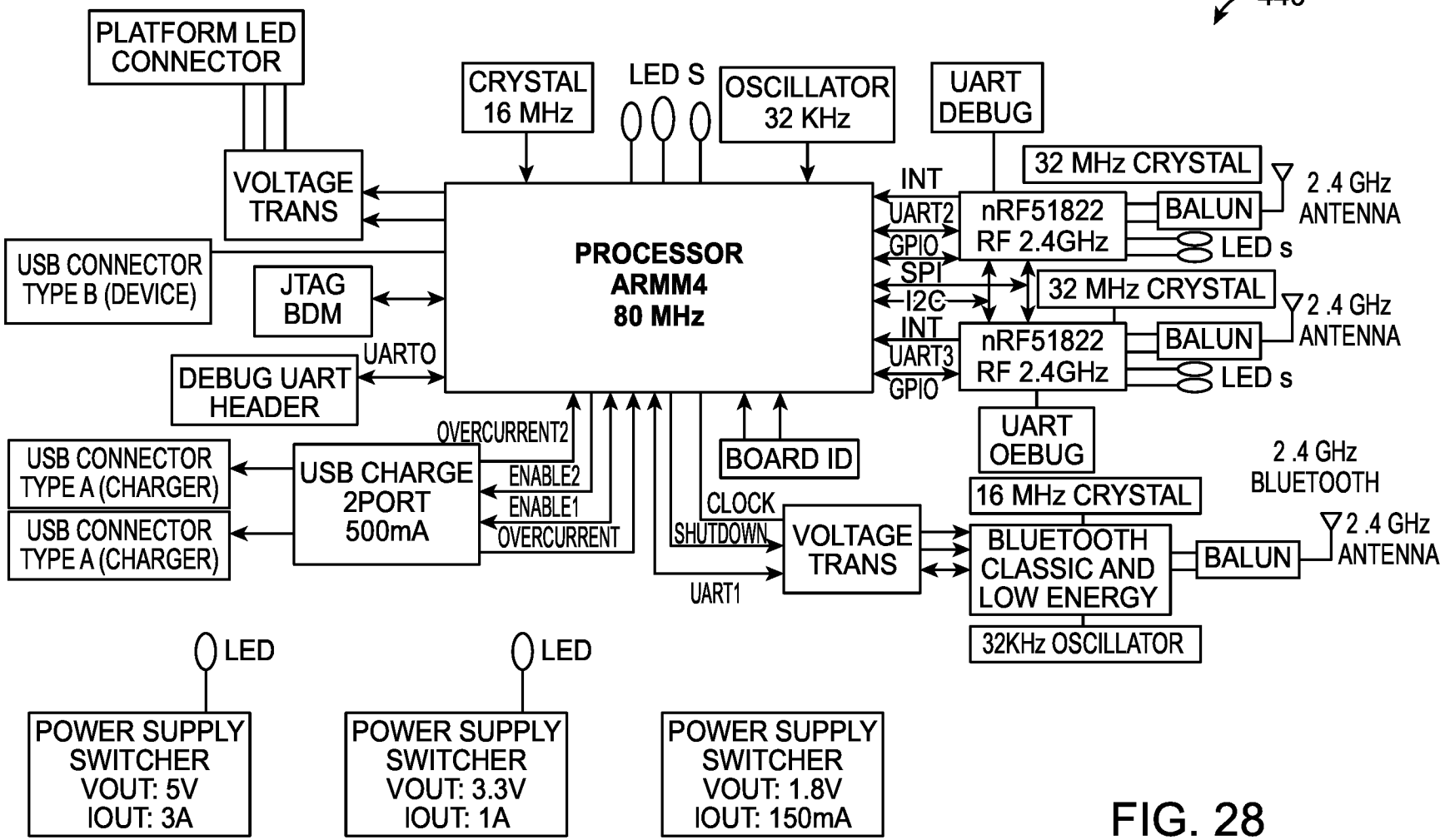
FIG. 28 is a block diagram illustrating an example aggregator board of a sensor system, in accordance with an example embodiment of the present technology.

FIG. 28 illustrates a block diagram of an example aggregator board 440. An aggregator board can be installed in a strut base behind the cabling/PCB board. An aggregator board can be integrated with or separate from a PCB board. An aggregator board can be configured to receive data from one or more sensors (for example, one or more POD) and compile, processes and transmit the processed data. In an embodiment, the processed data can be transmitted to a computing device (for example, a server, mobile device, gaming system) configured to run an API for translation of the processed data. The transmission can be by a USB connection, short-range wireless, Bluetooth, or any other transmission medium.

Figure 29:
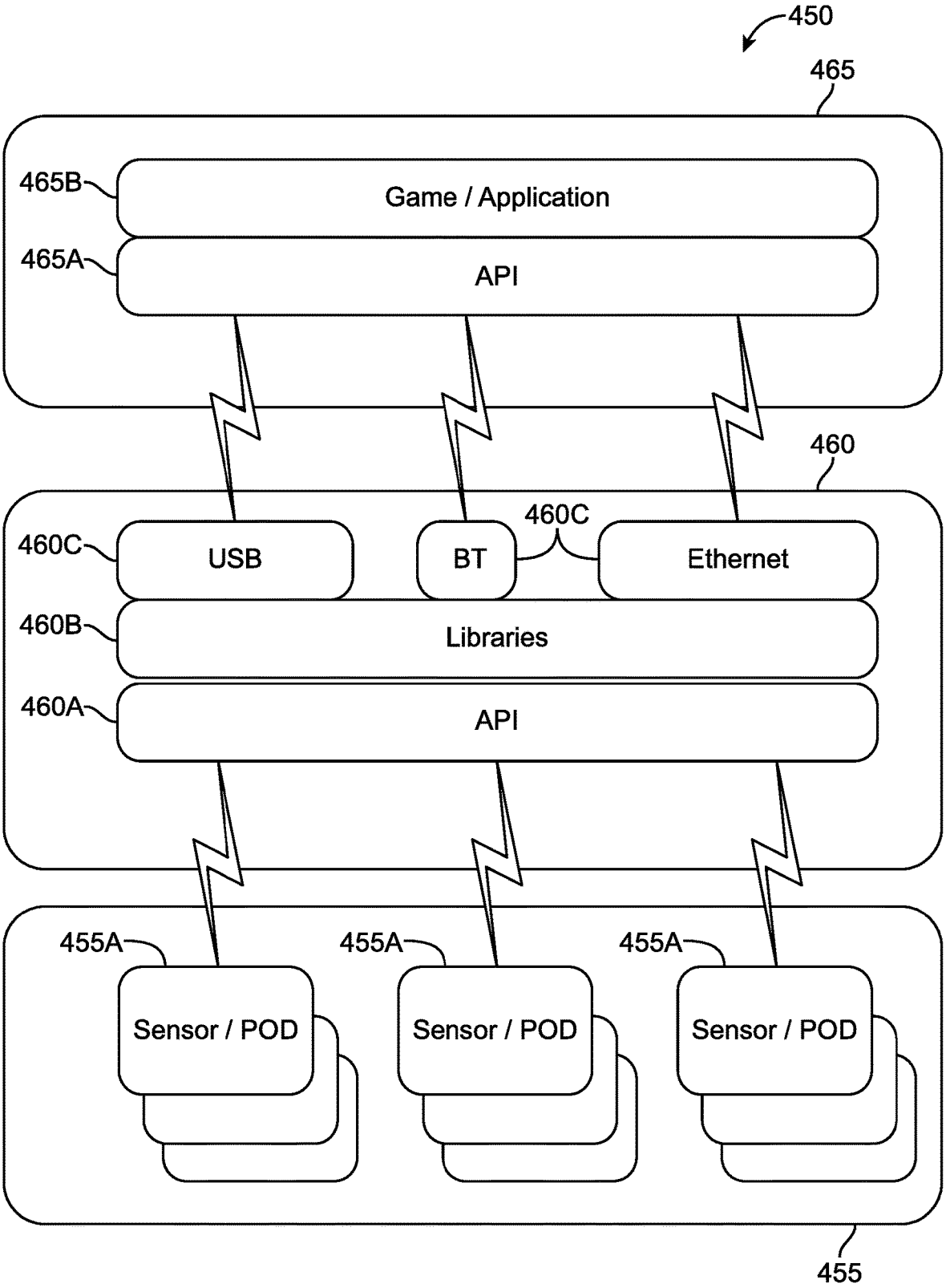
FIG. 29 is a block diagram illustrating an example layering model of a sensor system communication, in accordance with an example embodiment of the present technology.

FIG. 29 illustrates an example layer model for a POD communication system 450. Layer 1 455 can include one or more PODs 455A. In an embodiment, PODs 455A can be sensors. The PODs 445A can transmit output values to Layer 2 460. In an embodiment, Layer 1 455 can wirelessly transmit data to Layer 2 460, for example, by Bluetooth or a 2.4 GHz radio transmission.

Layer 2 460 can include a control box for receiving PODs 455A value output. In an embodiment, the control box is an aggregator board. Layer 2 460 can include an API 460A for translating received data from PODs 455A. Layer 2 460 can include different libraries 460B, for example, a filtering library, a processing library and motion library enabling translating received data from API 460A. In an embodiment, API 460A can call library functions to enable translation of the received POD data. Layer 2 460 can further include transmitting and receiving components 460C, for example, USB, Bluetooth, short-range wireless, 2.4 GHz radio, Wi-Fi and/or Ethernet.

Layer 3 465 can include a computing system 465B, for example, a PC, a tablet, a phone, a gaming system, or any other computing device. The computing device can run a game or application 465B along with an API 465A. The game or application 465B can be a computer game, a PlayStation game, an XBOX game, or any other game or application. The API 465A can receive data from Layer 2 460 and translate the received data to a format the game or application 465B can understand. Once translated by the API 465A, the movement of a user, tracked by PODs 455A in an omnidirectional locomotion system, can be translated into movements of a game or application. In another embodiment, the movement of a user, tracked by PODs 455A can be outside of an omnidirectional locomotion system.

Figure 30:
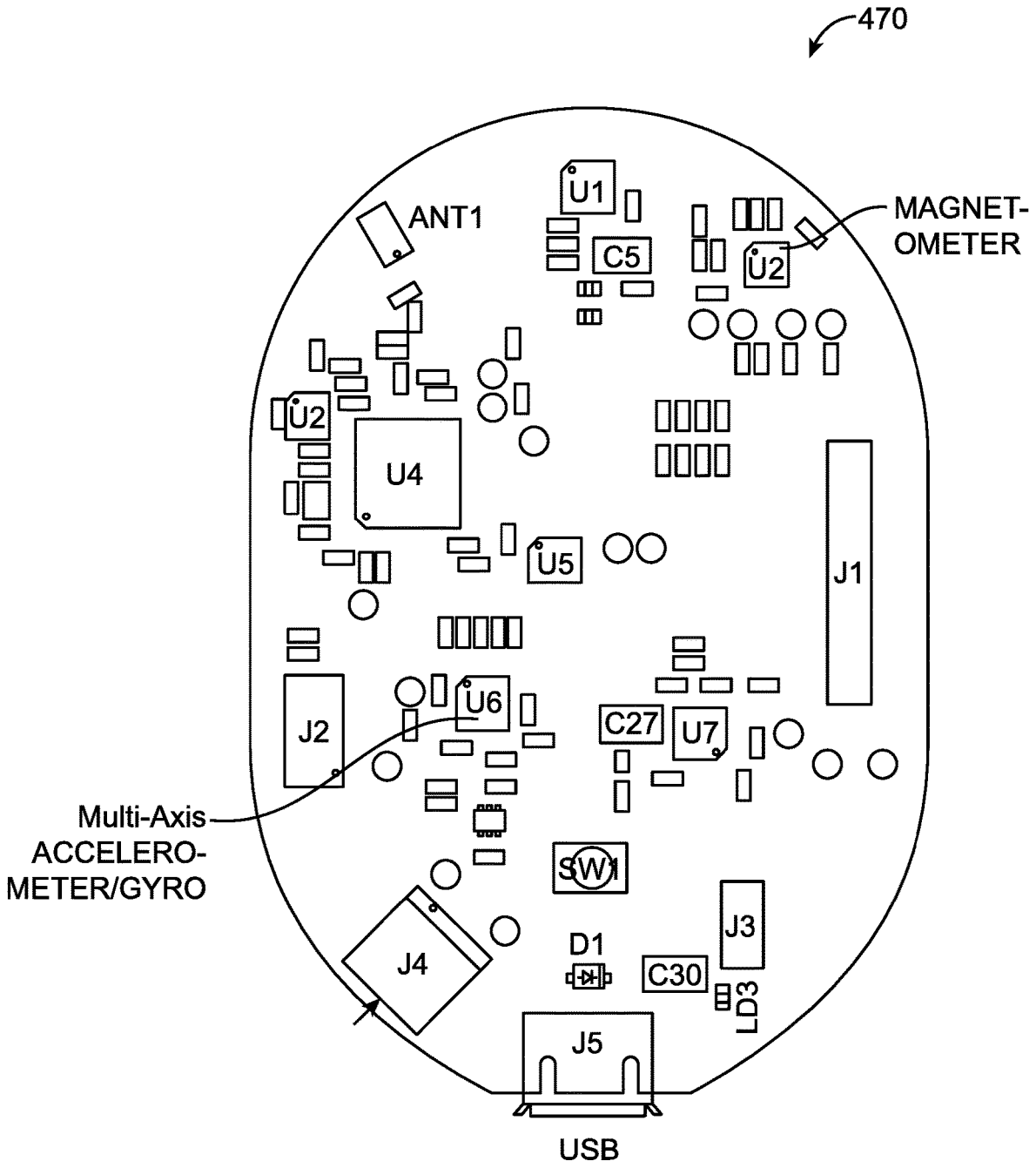
FIG. 30 is a schematic diagram illustrating an example sensor layout, in accordance with an example embodiment of the present technology.

FIG. 30 illustrates a circuit diagram of an example IMU layout 470 including a processor, multi-axis accelerometer/gyroscope, a magnetometer, and a USB connector. A magnetometer can measure a heading with respect to magnetic North. An accelerometer can measure acceleration and velocity in the X, Y, and Z planes. A gyroscope can measure an orientation of pitch, roll and yaw.

Figure 31:
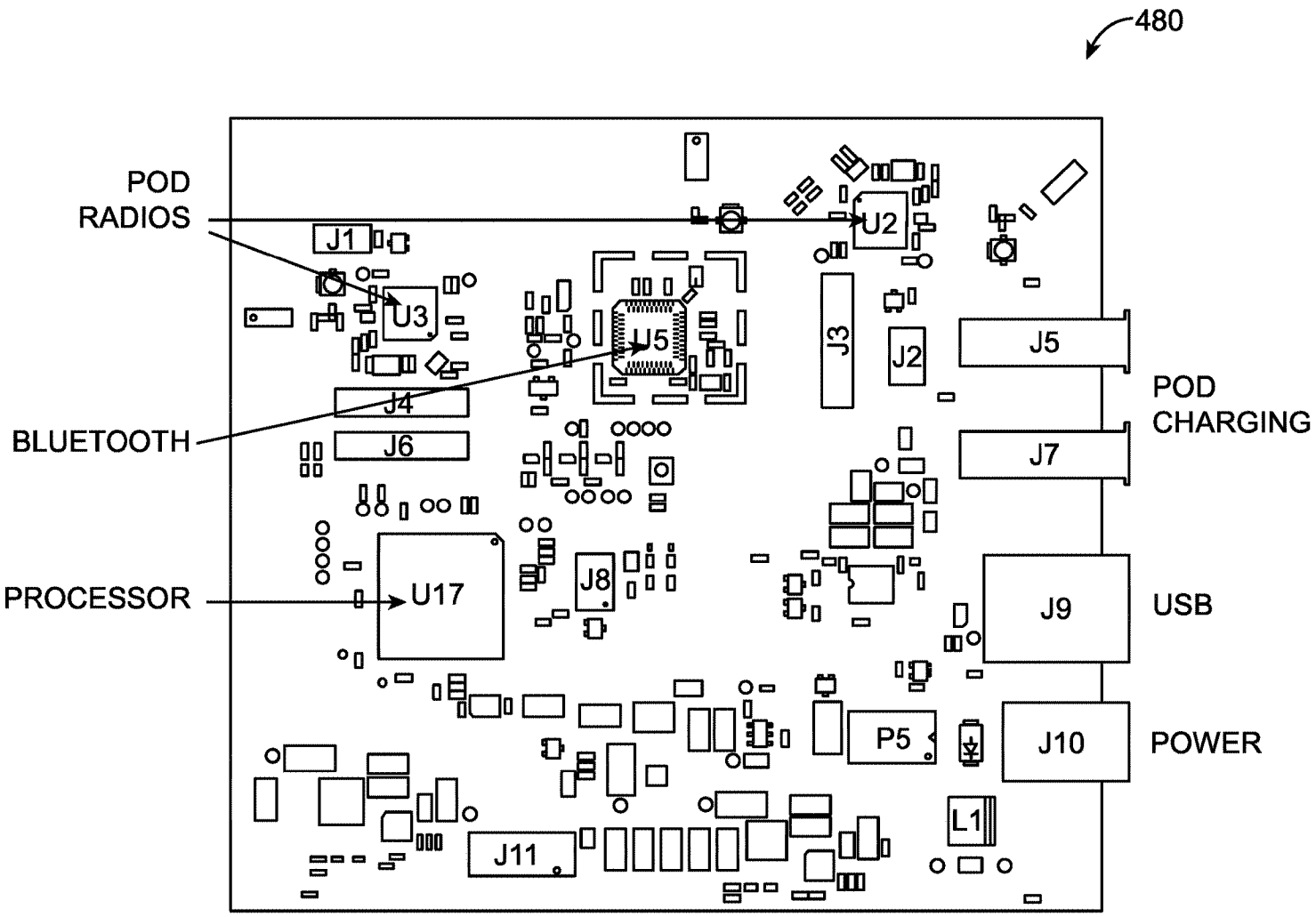
FIG. 31 a schematic diagram illustrating an example aggregator board layout, in accordance with an example embodiment of the present technology.

FIG. 31 illustrates a circuit diagram of an example of an aggregator board layout 480 including a processor, a Bluetooth receiver and transmitting, POD radios, POD charging, a USB, and a power management unit.

Figure 32:
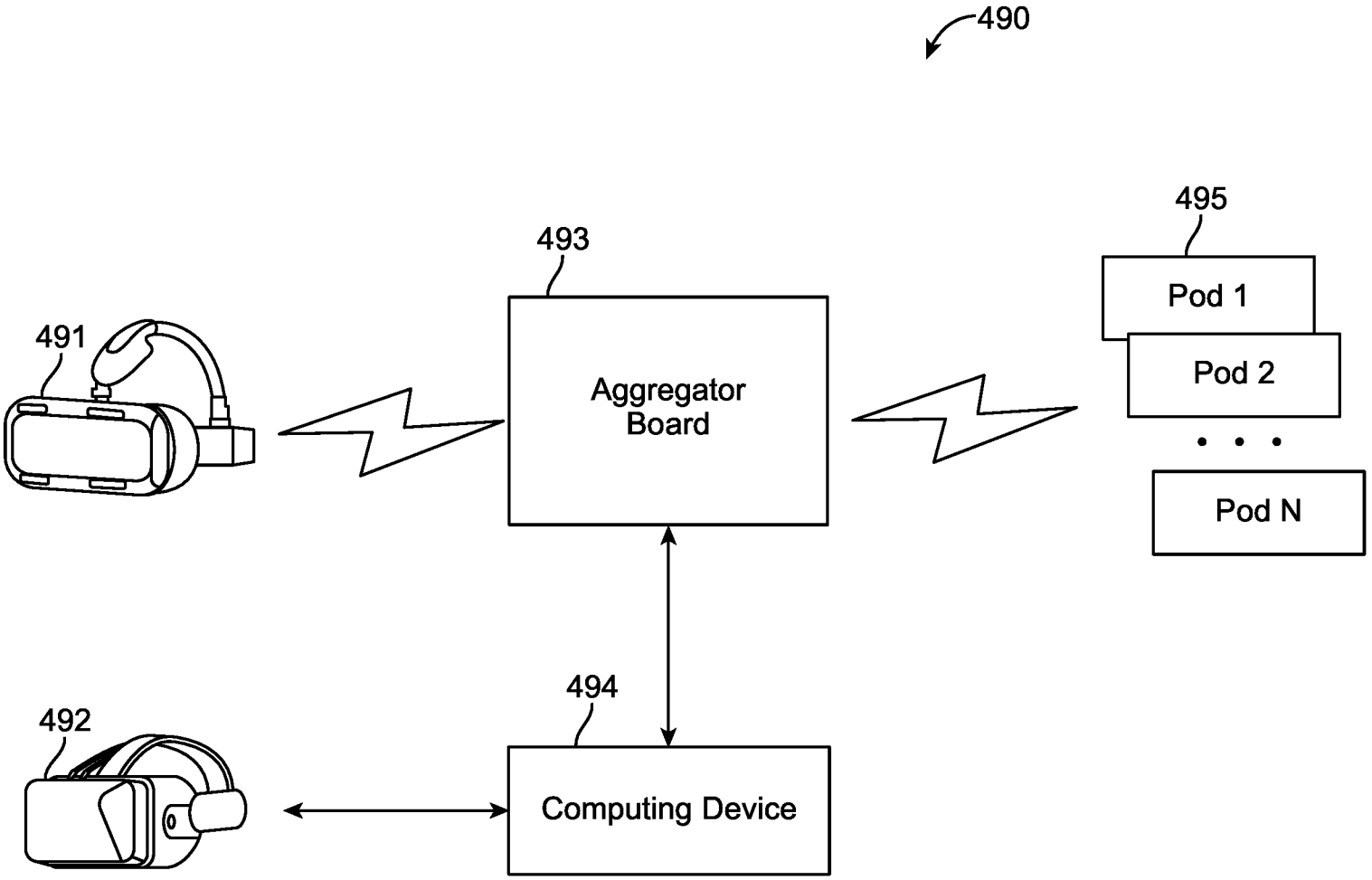
FIG. 32 is a block diagram illustrating an example sensor communication system, in accordance with an example embodiment of the present technology.

FIG. 32 is a block diagram of an example POD communication system 490. A POD communication system 490 can include a virtual reality headset 491 connected to an aggregator board 493 by short-range wireless, for example Bluetooth. A POD communication system can include a virtual reality headset 492 connected to an aggregator board 493 by USB or HDMI by a computer system 494. In another embodiment the virtual reality headset 492 connects to the aggregator board without first connecting to computer system 494. A POD communication system 490 can further include one or more PODs 495 connected to an aggregator board 493. In an embodiment, a connection between PODs 495 and aggregator board 493 is wireless, for example Bluetooth or 2.4 GHz radio. An aggregator board 493 can receive data, compile data, and process data and transmit the processed data to a computing system. In other embodiments, aggregator board can be one or more MCU. In other embodiments, the POD communication system 490 can transmit and receive data using HDMI, USB, Bluetooth, short-ranged wireless, Wi-Fi, Gazell protocol, or any other communication medium.

Figure 33:
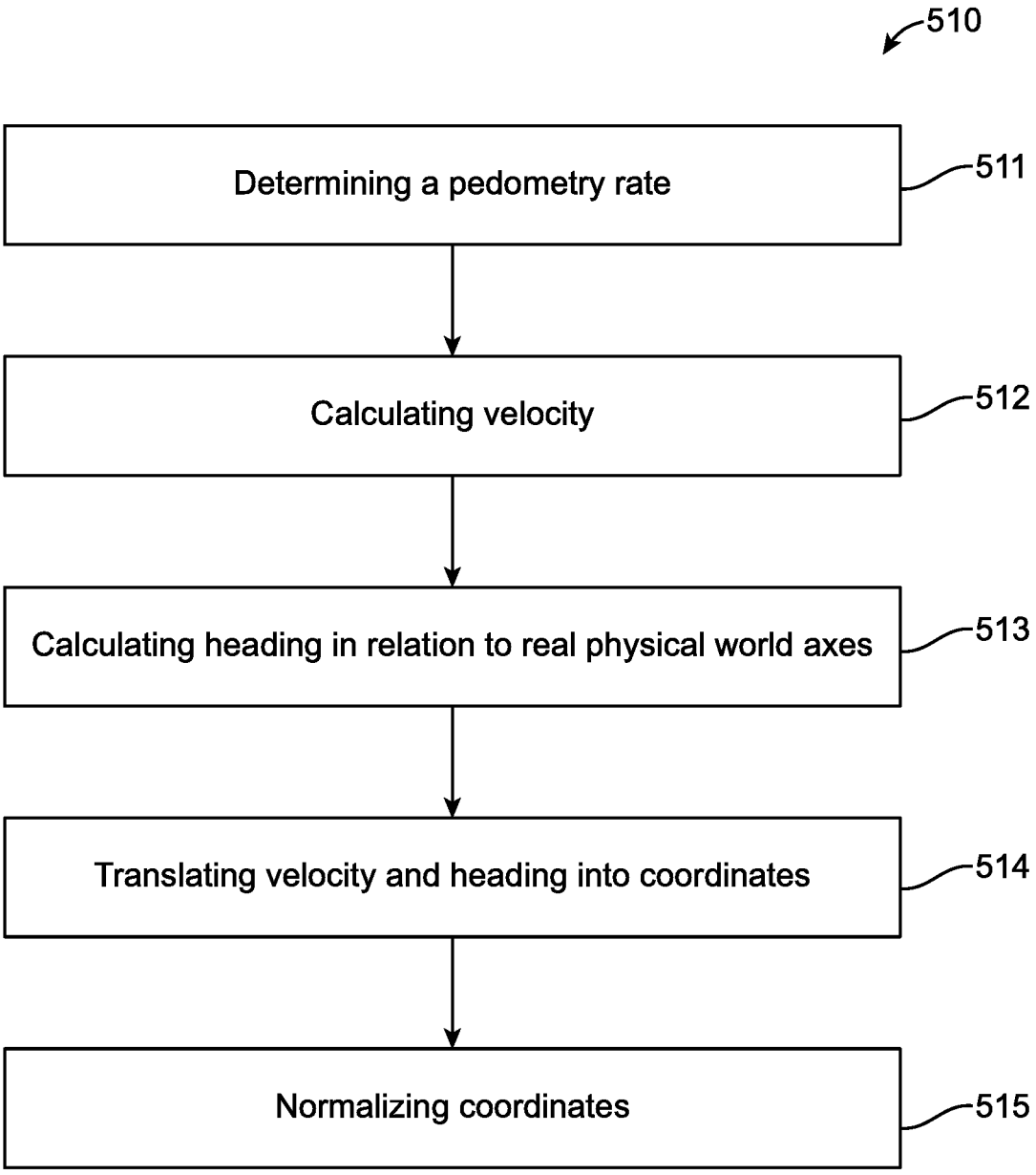
FIG. 33 is a flow diagram illustrating example method of decoupled movements in an omnidirectional locomotion system, in accordance with an example embodiment of the present disclosure.

FIG. 33 is a flow chart of an example method of a fully decoupled velocity and heading. Method 510 illustrated in FIG. 33 is provided by way of example, as there are a variety of ways to carry out the method. Additionally, while the example method is illustrated with a particular order of steps, those of ordinary skill in the art will appreciate that FIG. 33 and the steps illustrated therein can be executed in any order that accomplishes the technical advantages of the present disclosure and can include fewer or more steps than illustrated.

Each block shown in FIG. 33 represents one or more processes, methods, or subroutines, carried out in example method. The steps illustrated in FIG. 33 can at least be implemented in a system including an omnidirectional locomotion system 130, POD system 400, and/or POD communication system 490. Additional steps or fewer steps are possible to complete the example method. Each block shown in FIG. 33 can be carried out by at least a system including an omnidirectional locomotion system 130, POD system 400, and/or POD communication system 490. Alternatively, in another embodiment, each block shown in FIG. 33 can be carried out without the use of an omnidirectional locomotion system 130.

Method 510 can begin at block 511. At block 511, a pedometry rate of a user is determined by acceleration data received at an aggregator board from one or more PODs. In another embodiment, gyro data is received at an aggregator board. The pedometry rate can be the frequency of user steps during a predefined interval. In an embodiment, the pedometry rate can be determined by monitoring an acceleration of a user's feet during a predefined interval. In another embodiment acceleration data is received at a PCB that is separate from an aggregator. In another embodiment, accelerated data is received at a computing device bypassing an aggregator or PCB to determine a pedometry rate. In another embodiment, a change in rotation can be determined in place of a pedometry rate. When a pedometry rate is determined at block 511, the method can move to block 512.

At block 512, the determined pedometry rate of a user is used to calculate a velocity. A velocity is calculated by looking for peaks in acceleration followed by high frequency noise to indicate foot impact. Rate and magnitude of the relative energy in each foot step, as measured by the duration and peak of the acceleration, is used to calculate the rate of steps. In an embodiment, the velocity can be an average velocity. In another embodiment, the velocity can be a median velocity. In another embodiment, the velocity can be an angular velocity. When a velocity is calculated at block 512, the method can move to block 513.

At block 513, a heading is calculated for the one or more IMU. A corrected orientation is translated into real physical world axes to provide a heading of one or more PODs. In one embodiment, the one or more POD orientations can be averaged to provide an aggregate combined heading. In an embodiment, one or more PODs can be located on user's head, torso, feet, legs, arms, an accessory, halo, or harness. When a heading is determined at block 513, a method can move to block 514.

At block 514, the heading and velocity can be translated into 2-dimensional Cartesian coordinates (X, Y). The translated coordinates can represent gamepad and/or joystick values. For example, the velocity can be a magnitude or amplitude of the X and Y values and the heading can be translated into degree angles from relative magnetic North of the Earth. When the heading and velocity are translated into coordinates at block 514, the method can move to block 515.

At block 515, the coordinates are normalized into a minimum to maximum scale range, as defined by USB HID joystick/game pad descriptors. By virtue of control decoupled from camera view, additional movements such as walking backward, left and right strafing can be enabled. When the coordinates are normalized method 510 can end.

Method 510 can be used for a decoupled forward movement. A forward movement can be a relative movement in the Y direction relative to the center of one or more PODs, and generates a movement in the Y gamepad/joystick direction. An acceleration when a user foot is in the air can be measured in the direction of the heading of the foot. A forward velocity measurement can be then translated into "real world" coordinates relative to magnetic North of the Earth. All other motions not in the forward Y-axis of a POD, relative to the POD body, can be ignored to disallow spurious or false movements in alternate directions confining the motion identification process to forward motions.

Method 510 can be used for a decoupled backwards movement. A backwards movement can be a relative movement in the Y direction relative to the center of one or more PODs, and generates a movement in the Y gamepad/joystick direction. An acceleration when a user foot is in the air can be measured in the opposite direction of the heading of the foot. A backwards velocity measurement can be then translated into "real world" coordinates relative to magnetic North of the Earth. All other motions not in the backwards Y-axis of an POD, relative to the POD body, are ignored to disallow spurious or false movements in alternate directions confining the motion identification process to forward motions.

Method 510 can be used for a decoupled side movement or strafe movement. A side movement can be a relative movement in the X direction relative to the center of one or more POD, and generates a movement in the X gamepad/joystick direction. An acceleration when a user's foot is in the air can be measured in the perpendicular direction of the heading of the foot. A side velocity measurement can be then translated into "real world" coordinates relative to magnetic North of the Earth. All other motions not in the X-axis of a POD, relative to the POD body, are ignored to disallow spurious or false movements in alternate directions confining the motion identification process to forward motions.

Figure 34:
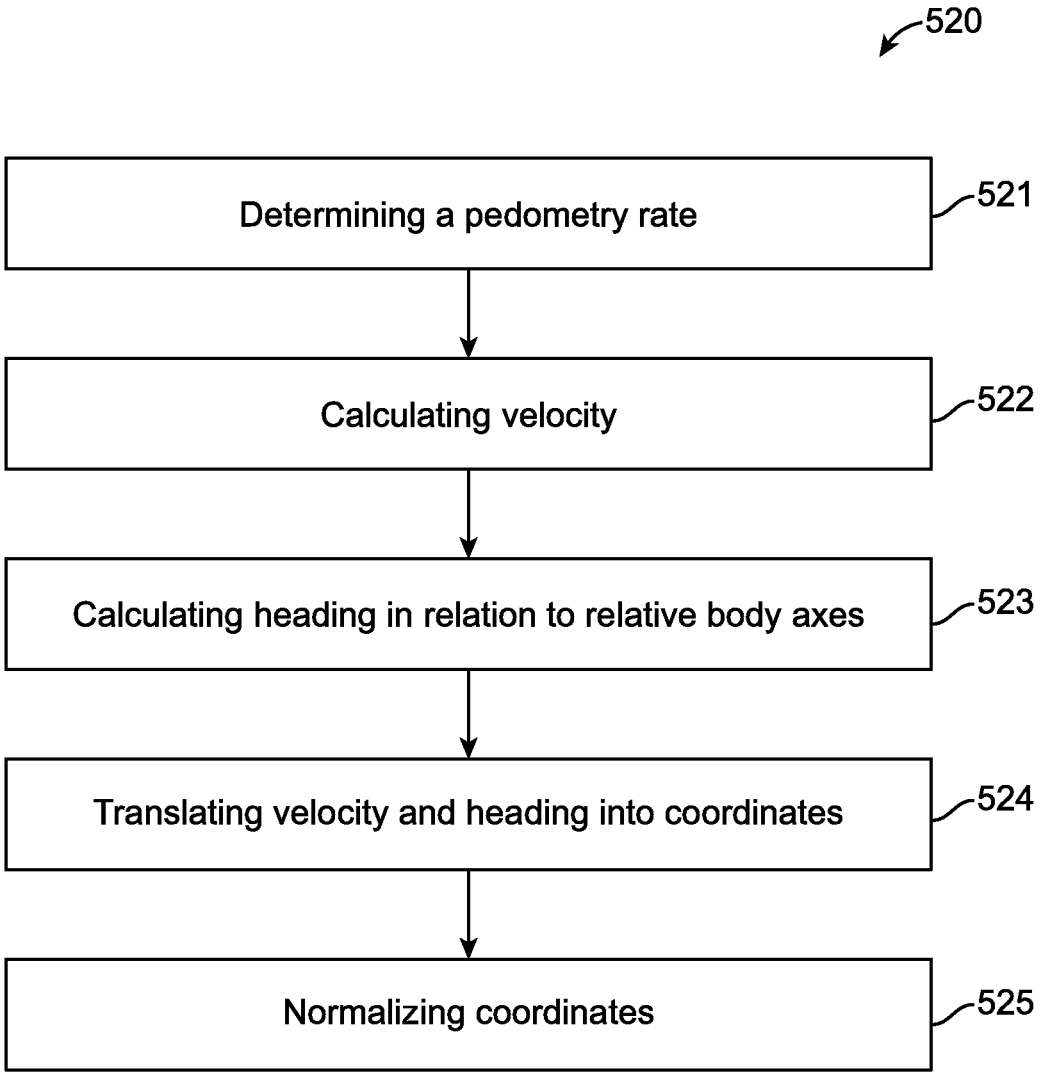
FIG. 34 is a flow diagram illustrating an example method of coupled movements in an omnidirectional locomotion system, in accordance with an example embodiment of the present disclosure.

FIG. 34 is a flow chart of an example method of a coupled forward, backward, and side-to-side movements. Method 520 illustrated in FIG. 34 is provided by way of example, as there are a variety of ways to carry out the method. Additionally, while the example method is illustrated with a particular order of steps, those of ordinary skill in the art will appreciate that FIG. 34 and the steps illustrated therein can be executed in any order that accomplishes the technical advantages of the present disclosure and can include fewer or more steps than illustrated.

Each block shown in FIG. 34 represents one or more processes, methods, or subroutines, carried out in example method. The steps illustrated in FIG. 34 can at least be implemented in a system including an omnidirectional locomotion system 130, POD system 400, and/or a POD communication system 490. Additional steps or fewer steps are possible to complete the example method. Each block shown in FIG. 34 can be carried out by at least a system including an omnidirectional locomotion system 130, POD system 400, and/or POD communication system 490. Alternatively, in another embodiment, each block shown in FIG. 34 can be carried out without the use of an omnidirectional locomotion system 130.

Method 520 can begin at block 521. At block 521, acceleration data is received at an aggregator from one or more PODs is used to determine a pedometry rate of a user. In another embodiment acceleration data is received at a PCB that is separate from an aggregator. In another embodiment, accelerated data is received at a computing device bypassing an aggregator or PCB to determine a pedometry rate. When a pedometry rate is determined at block 521, the method can move to block 522.

At block 522, the determined pedometry rate of a user is used to calculate a velocity. A velocity is calculated by looking for peaks in acceleration followed by high frequency noise to indicate foot impact. Rate and magnitude of the relative energy in each foot step, as measured by the duration and peak of the acceleration, is used to calculate the rate of steps. When a velocity is calculated at block 522, the method can move to block 523.

At block 523, a heading is calculated for the one or more PODs. An orientation of the one or more PODs is translated into relative body axes of the one or more PODs to determined an intended direction of motion. In one embodiment, the one or more PODs orientations can be averaged to provide an aggregate combined heading. In an embodiment, one or more PODs can be located on user's head, torso, feet, legs, arms, an accessory, halo, or harness. In this embodiment, real world coordinates are not calculated and are not used to provide heading. The one or more PODs relative self-orientations are then averaged to provide a heading. When a heading is calculated at block 523, a method can move to block 524.

At block 524 the aggregated combined heading and velocity can be translated into 2-dimensional Cartesian coordinates (X-axis and Y-axis). The translated coordinates can represent gamepad and joystick values. For example, the velocity can be a magnitude of the X and Y values and heading (orientation) is translated into degrees 90 degree angle increments from the forward (relative to Y-axis of the PODS). When the heading and velocity are translated into coordinates at block 524, the method can move to block 525.

At block 525 the coordinates are normalized into a minimum to maximum scale range, as defined by USB HID joystick/game pad descriptors. When the coordinates are normalized method 520 can end.

Method 520 can be used for forward and backwards coupled movements. Forward and backwards can be relative movement in the Y direction relative to the center of the PODs, and generates a movement in the Y gamepad/joystick direction. An acceleration when a user's foot is in the air can be measured in the direction of the camera position for forward movement and in the opposite direction of the camera position for backwards movement. All other axes, relative to the PODs, can be ignored to disallow spurious or false movements in alternate directions, therefore confining the motion identification process to forward and backwards motions.

Method 520 can be used for side coupled movement or strafing coupled movements. Side movements can be relative movement in the X direction relative to the center of the PODs, and generates a movement in the X gamepad/joystick direction. An acceleration when a user foot is in the air can be measured in the perpendicular direction of the camera position. All other axes, relative to the PODs, can be ignored to disallow spurious or false movements in alternate directions, therefore confining the motion identification process to side motions.

In determining movement of a user of an omnidirectional locomotion system, it is desirable to decrease the time for detecting walking has begun on the omnidirectional locomotion platform. A delay in detection can be perceived as lag between a user's movement on the platform and a user's avatar in a virtual environment. An additional layer for improved step detection performance for the initial step is specified in an embodiment where triggering off an acceleration above a minimum level (threshold) in the forward Y-direction (relative to the POD coordinates) generates a user movement in gamepad/joystick coordinates (relative to real world North of the Earth). This trigger can be armed during times when a motion library has not completed calculating acceleration and velocity intensities. Relative strength of the acceleration energy can be used to ease a transition from a "first step" trigger motion into a full motion library, for example, forwards walking, backwards walking, running, crouching, strafe, creep, jumping or any additional motion gestures detectable on the omnidirectional locomotion system. The trigger has a rate independent hysteresis to alleviate an appearance of jitteriness in user motions caused by noise in measured accelerometer data.

Decreasing a lag between the cessation of movement and its detection is specified in an embodiment which triggering off an acceleration below a maximum level in all relative directions (relative to the POD coordinates) forces user movement to stop. This trigger is armed during times when the motion library has identified intended user motions. The trigger has a rate independent hysteresis as to alleviate the appearance of jitteriness in user motions caused by noise in the measured accelerometer data.

Figure 35:
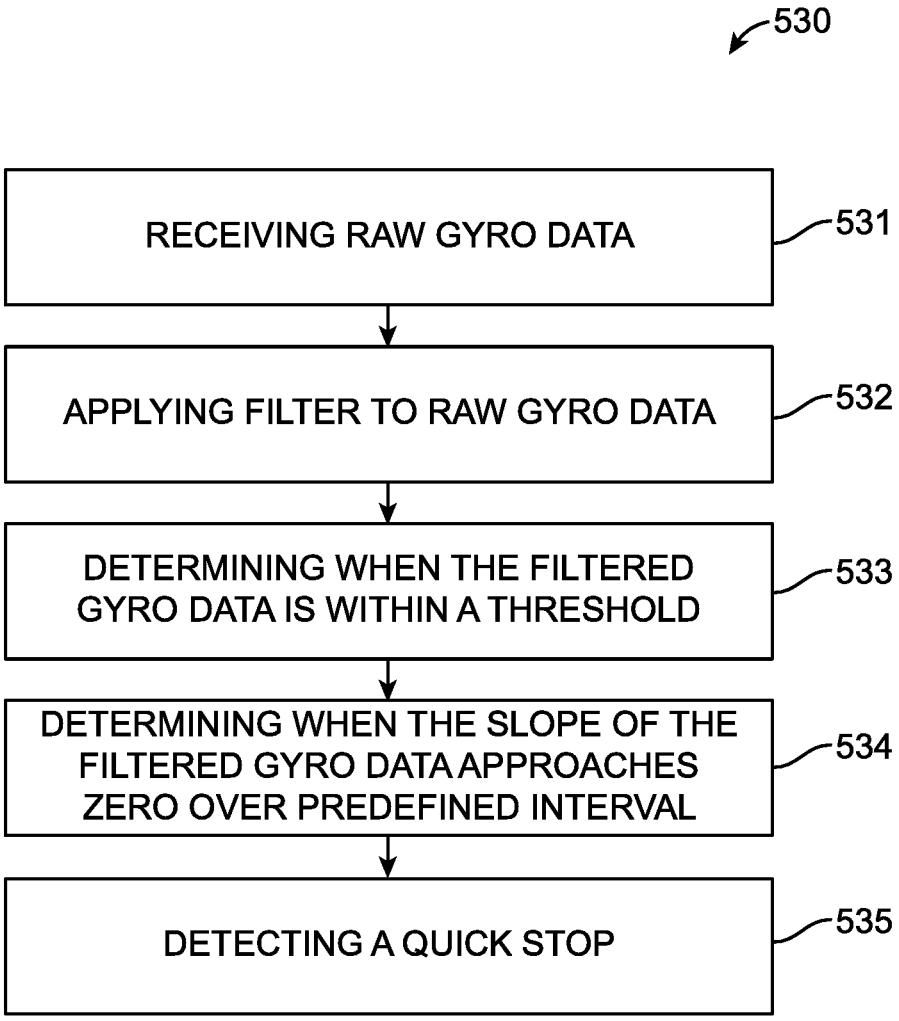
FIG. 35 is a flow diagram illustrating an example method of a quick stop, in accordance with an example embodiment of the present disclosure.

FIG. 35 is a flow chart of an example method of detecting a quick stop of a user movement. Method 530 illustrated in FIG. 35 is provided by way of example, as there are a variety of ways to carry out the method. Additionally, while the example method is illustrated with a particular order of steps, those of ordinary skill in the art will appreciate that FIG. 35 and the steps illustrated therein can be executed in any order that accomplishes the technical advantages of the present disclosure and can include fewer or more steps than illustrated.

Each block shown in FIG. 35 represents one or more processes, methods, or subroutines, carried out in example method. The steps illustrated in FIG. 35 can at least be implemented in a system including an omnidirectional locomotion system 130, a POD system 400, and a POD communication system 490. Additional steps or fewer steps are possible to complete the example method. Each block shown in FIG. 35 can be carried out by at least a system including an omnidirectional locomotion system 130, a POD system 400, and a POD communication system 490. Alternatively, in another embodiment, each block shown in FIG. 35 can be carried out without the use of an omnidirectional locomotion system 130.

Method 530 can begin at block 531. At block 531, the method can receive, from one or more PODs, raw gyro data. In an embodiment the raw gyro data can be an angular velocity. The angular velocity can be used to determine if a user is moving forward or backwards, for example walking forwards/backwards or running forwards/backward by the change in rotation of a user's feet. In an embodiment if the angular velocity is non-zero the user can be moving. In another embodiment, the angular velocity can be determined by receiving the one or more POD data over a predefined interval. In another embodiment, the received data can be acceleration data for calculating a velocity. If at block 531 it is determined that the user is moving, the method can move to block 532.

At block 532, the method can normalize or smooth the raw data by applying a filter. In an embodiment, the raw gyro data can be run through a fast stopping filter. In regard to the fast stopping filter, the received raw gyro data can be run through an exponential moving average (EMA) filter, then the smoothed (filtered) values can be compared to previous smoothed values, to determine a smooth delta resulting in a smoothed gyro data graph. In another embodiment, the raw gyro data can be run through an analog speed filter. In regard to the angle speed filter the raw gyro x-axis values for both feet PODs can be run through an EMA filter to calculate the absolute value of each gyro. The filtered values can be added together, scaled, and then an offset is added. In an embodiment the offset can be a scale offset, i.e., so the value falls within a valid joystick output value. The offset value can then run through an EMA filter. The EMA filter can be a new EMA filter or the previously mentioned EMA filter. The result is a smooth output that is approximately equivalent to a velocity, for example a walking velocity. An example smoothed gyro data graph can be seen in FIG. 36. When a filter has been applied the method can move to block 533.

Figure 36:
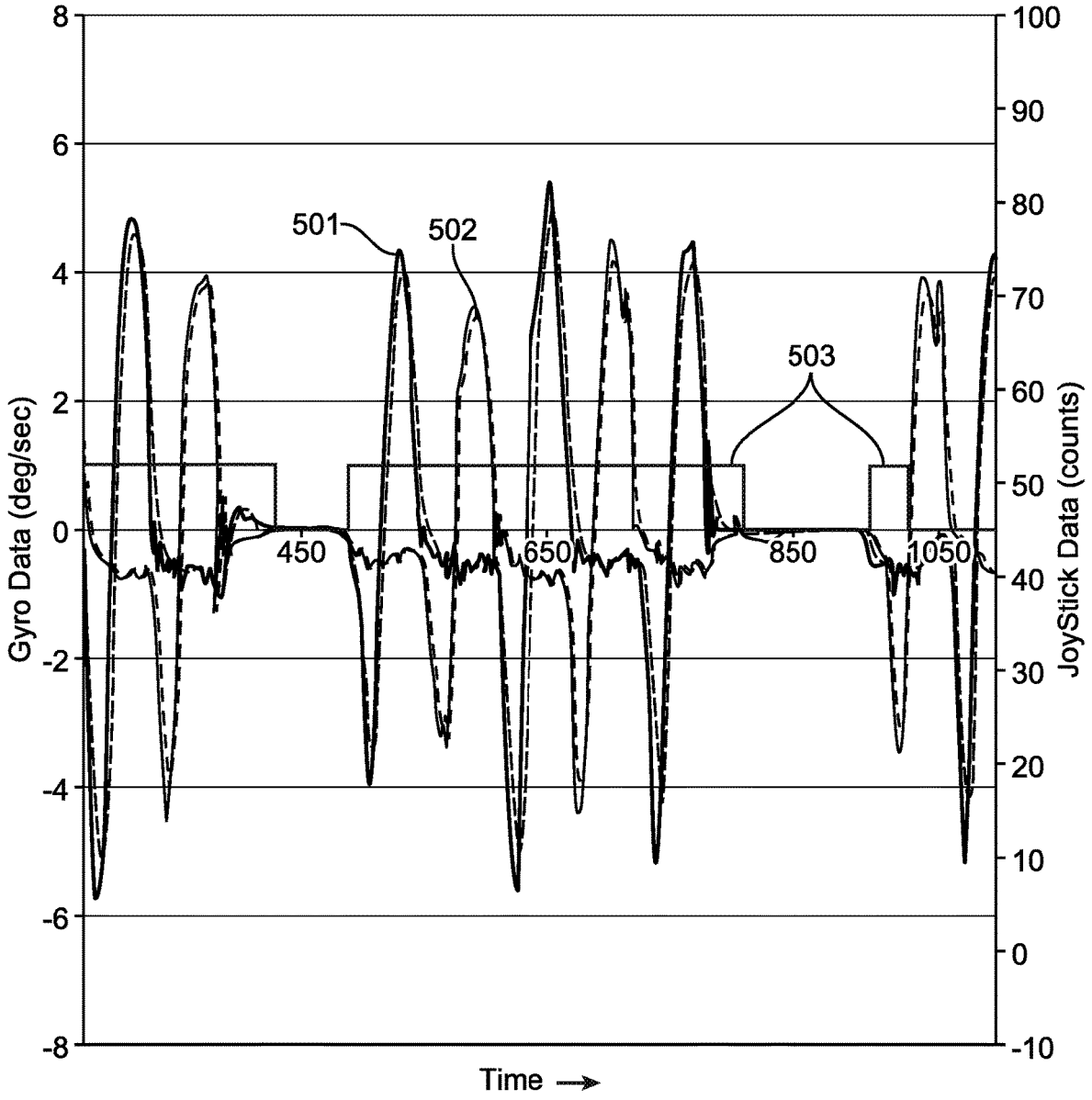
FIG. 36 is a graph illustrating an output from an example sensor system, in accordance with an example embodiment of the present disclosure.

At block 533, the method can determine if the smoothed gyro data at block 532 drops within a predefined threshold. In an embodiment the smoothed gyro data can be an angular velocity (rate of rotation per second) in the direction of motion. For example, the angular velocity can be determined from the gyro axis perpendicular to the direction of the motion. The predefined threshold can be used to determine when the user is slowing down. In an embodiment, predefined threshold can be 0.33 degrees per second. The angular velocity can be monitored at a predetermined interval, for example 1 ms, 5 ms, 10 ms, 15 ms, and 20 ms. As shown in FIG. 36, when the angular velocity of POD 501 and POD 502 drops within a predefined threshold 503 the movement of the user can be slowing down. In an embodiment, to prevent a false stop detection, the predefined threshold can be determined dynamically based on the velocity of the user movement. For example, when the velocity is calculated at a slow speed (walking or creeping) the predefined threshold can be a tighter window making the trigger points smaller. When the forward velocity is calculated at a high speed (running) the predefined threshold can be a larger window making the trigger points larger. In another embodiment to prevent a false stop a decay can be added when the angular velocity drops to the predefined threshold. The added decay can alleviate any stuttering effect. The decay is an exponential decay calculated mathematically, to have a gradual transition towards zero. When the smoothed gyro data has dropped below the predefined threshold, the method can move to block 534.

At block 534, the method can determine when the slope of the smoothed gyro data has approached zero for a predefined interval. For example, during a predefined interval of 1 ms, 5 ms, 10 ms, 15 ms, or 20 ms. When the slope of the angular velocity continues to approach zero, a stop can be detected. In an embodiment, a stop can be detected when the slope is less than 0.01 degrees per second squared. Alternatively, if during this same interval the slope does not continue to approach zero, a stop cannot be detected. In an embodiment, the slope deltas (during the predefined interval) can be analyzed to locate a peak. The velocity can be set to the maximum of each peak until the next peak is located, which then can be set to the velocity. In another embodiment, when the angular velocity slope is within a minimum predefined window, a counter is incremented. If the counter reaches seven, the velocity is set to zero. When the predefined interval has ended the method can move to block 535 if the slope approached zero for the predefined interval or can return to block 531 if the slope did not approached zero for the predefined interval.

At block 535, the method can detect a quick stop. For example, when the smooth gyro data is within the threshold and when the slope of the smooth gyro data approached zero during the predefined interval a quick stop is detected. When a quick stop is detected, method 530 can end.

Figure 37:
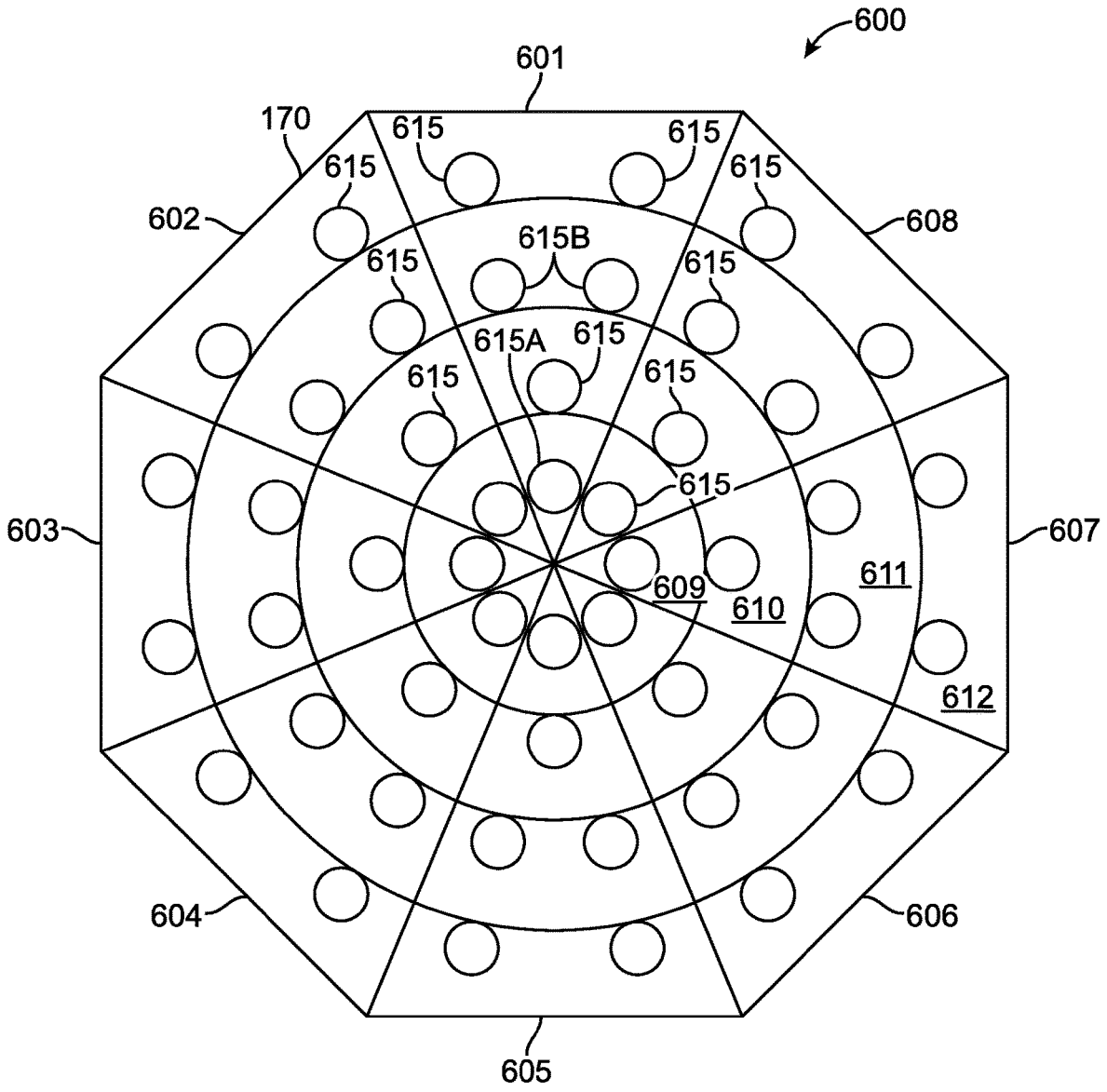
FIG. 37 is a top view illustrating an example sensor layout of an example omnidirectional locomotion system, in accordance with an example embodiment of the present disclosure.

FIG. 37 illustrates a platform sensor layout 600. Platform 170 can be equipped with one or more sensors 615 for tracking the movement of one or more feet. In an embodiment, sensors 615 can be proximity sensors, for example capacitive sensors using the body capacitance of each of the user's feet as input. The capacitive sensors can be activated when one or more feet are moved over the sensor. In another embodiment, sensors 615 can be magnetic sensors, optical sensors, spiral sensors, IMU sensors, PODs, or any sensors capable of high accuracy readings. Platform 170 can include a harness (not shown) and halo (not shown) for supporting a user as shown in FIG. 3 and FIG. 4. The harness can include one or more sensors for determining an orientation of a user, for example a user's torso orientation. The halo can include one or more sensors for determining an orientation of a user, for example a user's torso orientation. In another embodiment, a user's footwear can comprise one or more sensors, for example to differentiate between a left and right foot, the front of a foot and the back of a foot, or a toe and a heel.

Platform 170 can be divided into two or more concentric circles. For example, as shown in FIG. 37, platform 170 can be divided into four concentric circles 609, 610, 611 and 612. Sensors 615 can be distributed on platform 170 in concentric circles 609, 610, 611 and 612. In another embodiments platform 170 can be divided into two or more regular polygons. In another embodiment, platform 170 can be divided into a center area and adjoining trapezoidal areas. In still another embodiment, platform 170 can be divided into a square symmetric XY grid. Platform 170 can further be divided into two or more slices. For example, as shown in FIG. 37, platform 170 can be divided into 8 slices, 601, 602, 603, 604, 605, 606, 607, and 608. One or more sensors 615 can be located within the cross-section of each concentric circle and each slice. For example, sensor 615A can be located within the cross-section of the inner most concentric circle 609 and slice 601. Sensors 615B can be located within the cross-section of concentric circle 611 and slice 601. In another embodiment, the cross-section of the inner most concentric circle 609 and slice 601 can include two or more sensors. In another embodiment, each cross-section of a concentric circle and slice can include two or more sensors.

Sensors 615 can be of equivalent size or of differing size. For example, sensors 615 can be of a smaller size when located near the center of platform 170 and progressively larger the further from the center of platform 170 the sensors 615 are located. In another embodiment, the sensors can be of equivalent size, for example, 1.5, 2.5, 3.5, 4.5 or 5.5 inches or any other size in diameter.

Figure 38:
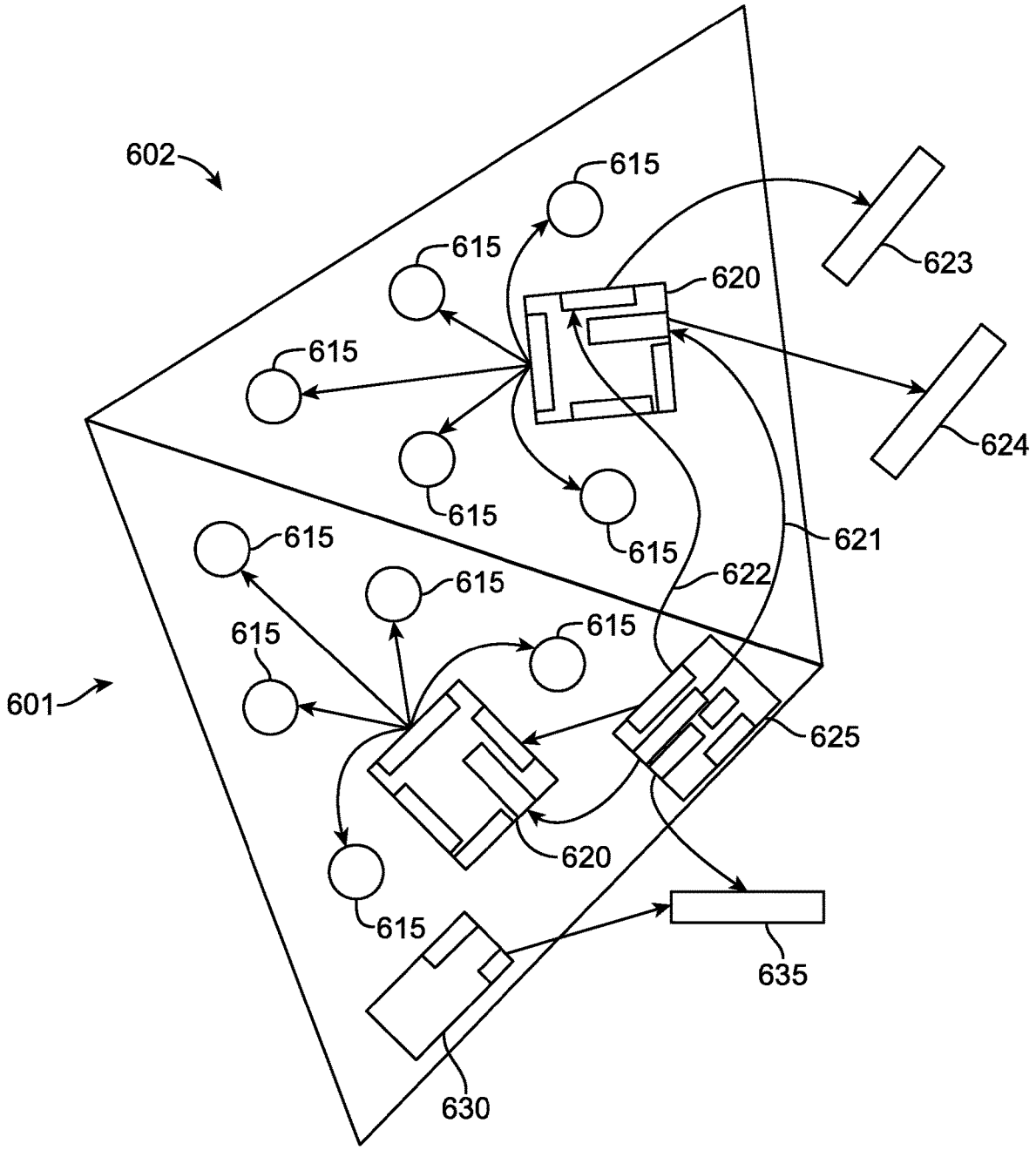
FIG. 38 is a top view illustrating an example first and second slice of an example omnidirectional locomotion 40 system, in accordance with an example embodiment of the present disclosure.

FIG. 38 illustrates an example of two slices in communication of an omnidirectional locomotion system. Sensors 615 can be connected to one or more printed circuit board (PCB) 620. For example, sensors 615 located in each platform slice can be electronically coupled to a PCB 620 located in their respective slice. In another embodiment, sensors from all slices can be connected to a centralized PCB. Sensors 615 can be electronically coupled by coaxial cable to PCB 620. In another embodiment, sensors 615 can be electronically coupled to PCB 620 by short-range wireless communication, for example Bluetooth. The PCB in each slice can be electronically coupled by a digital communication link to the PCB in adjacent slices, for example, in a daisy chain or ring configuration. PCB 620 located in slice 601 can electronically coupled to PCB 620 located in slice 602, which can be electronically coupled to PCB 620 located in slice 603. In an embodiment, slice 601, can included a micro-controller unit (MCU) with Universal Serial Bus (USB) capabilities 625. In another embodiment, slice 601, can include a central processing unit with USB capabilities. MCU 625 can supply power to PCB 620 in slice 601 and PCB 620 in slice 602 by connection 621. PCB 620 in slice 602 can supply power to PCB 620 in slice 603 by connection 624, which can supply the PCB in the adjacent slice in the daisy chain configuration until the last PCB is supplied with power. MCU 625 can also supply a serial bus to PCB 620 in slice 602 by connection 622, for example an inter-integrated circuit (I2C) bus, an universal asynchronous receiver/transmitter (UART), a serial peripheral interface bus (SPI), a local interconnect network bus (LIN), a controller area network bus (CAN), or any other type of serial bus. In another embodiment, serial bus communication can be achieved through local wireless communication devices located on each slice, either integrated or independent the MCU. PCB 620 in slice 602 can supply the serial bus to PCB 620 in slice 603 by connection 623, which can supply the PCB in the adjacent slice in the daisy chain configuration until the last PCB is supplied. In another embodiment, PCB 620 in slices 601-608 can be electronically coupled to a centralized PCB, for example in a star configuration. In another embodiment, the electronic coupling can be short-range wireless communication. MCU 625 can transfer to and receive data from a computer system 635. For example, a server, a gaming system, mobile device, or an equivalent computer system. In another embodiment, MCU 625 can monitor sensor activity by continuously polling PCB 620 in slices 601-608 by the electronically coupled or wirelessly coupled bus. In another embodiment, PCB 620 in slices 601-608 can alert MCU 625 of sensor activity by means of a hardware interrupt, for example, an electronic alerting signal to indicate an event needing immediate attention. Slice 601 can also include a Debug Kit 630 in connection with computer system 635.

Slice 602 can contain one or more sensors 615 and PCB 620. Slices 603-608 can be substantially similar to slice 602. Slice 602 can be connected in a daisy chain with slices 601 and 603. Slice 602 can receive power and serial bus from slice 601. Slice 602 can transmit power and serial bus to slice 603. This process can be repeated until slice 608 receives power and serial bus from slice 607. This process can be repeated for more or less slices depending on the number of slices in platform 170. Slices 602-608 can contain a redundant MCU 625 and Program and Debug Kit 630.

Figure 39:
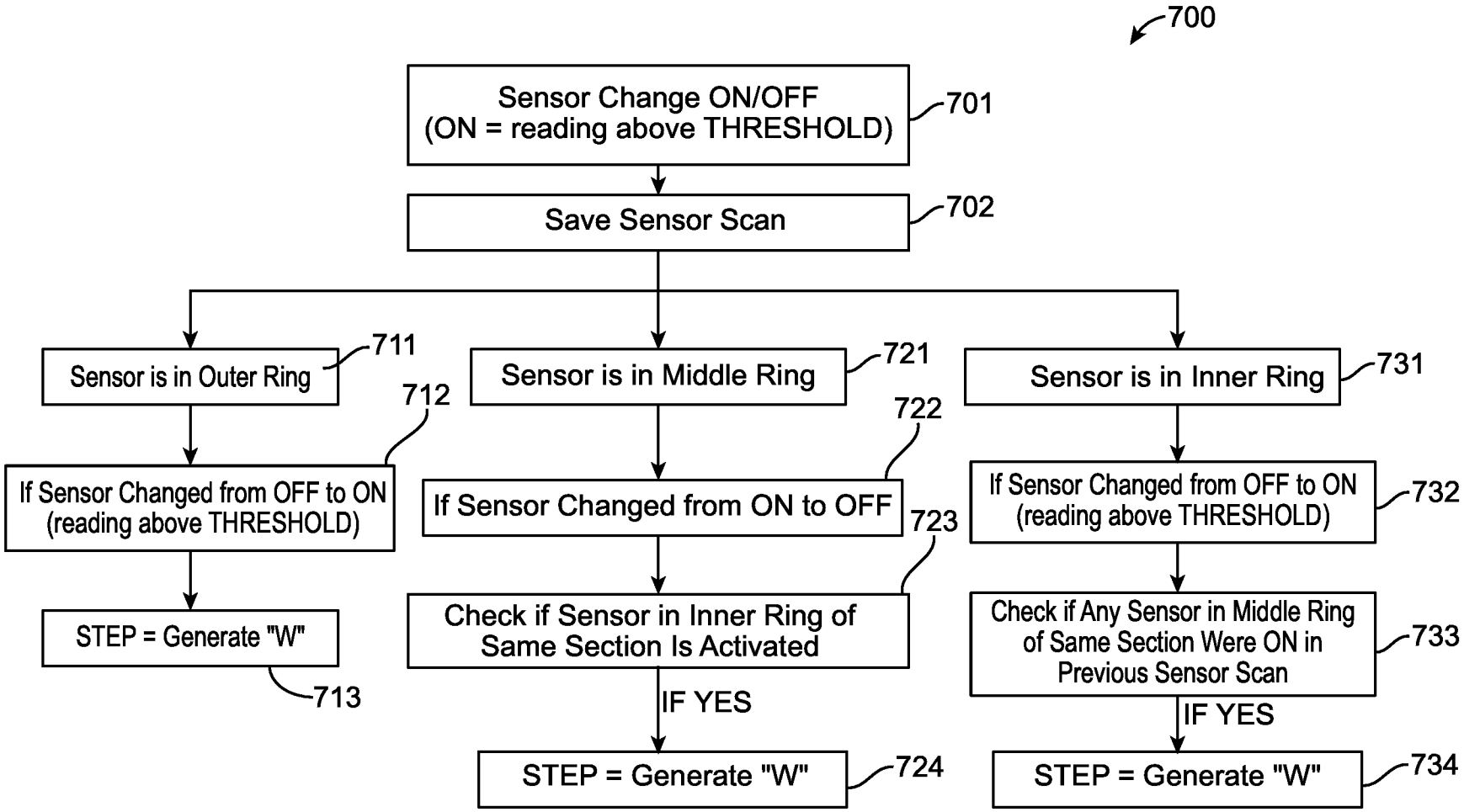
FIG. 39 and FIG. 40 are flow diagrams illustrating example methods for generating a forward movement, in accordance with an example embodiment of the present disclosure.
Figure 40:
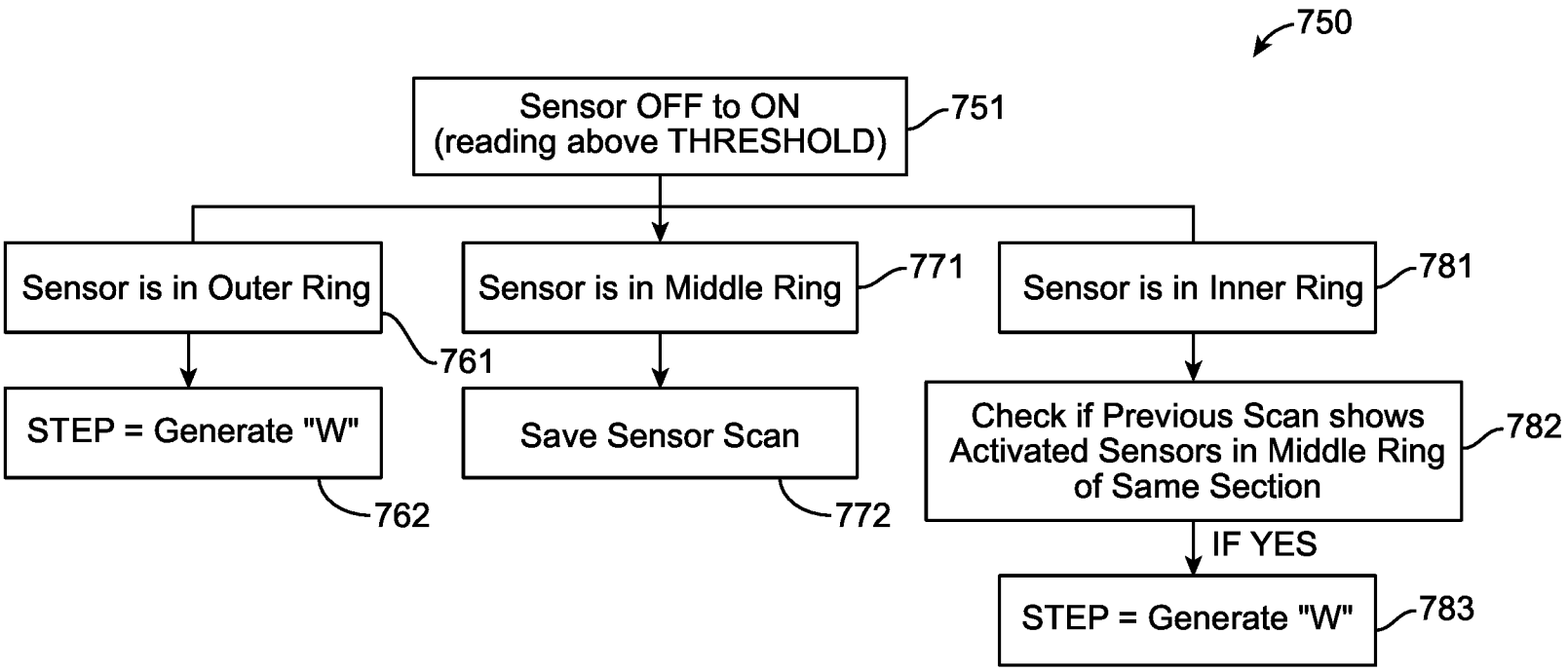

FIG. 39 and FIG. 40 are flow charts illustrating an example method 700 and method 750 for sensing a user's forward movement. A user's forward movement can be variable. Method 700 and method 750 are provided by way of example, as there are a variety of ways to carry out the method. Additionally, while the example methods is illustrated with a particular order of steps, those of ordinary skill in the art will appreciate that FIG. 39 and FIG. 40 and the steps illustrated therein can be executed in any order that accomplishes the technical advantages of the present disclosure and can include fewer or more steps than illustrated.

Each block shown in FIG. 39 and FIG. 40 represent one or more processes, methods or subroutines, carried out in example method. The steps illustrated in FIG. 39 and FIG. 40 can be implemented in at least a system including platform 170. Each block shown in FIG. 39 and FIG. 40 can be carried out at least by platform 170. The rings described in FIGS. 39 and 40 are an example representation of three concentric circles for a sensor layout in platform 170. There can be more or less rings depending on the designated sensor layout and therefore method 700 and method 750 can contain more or less branches keeping consistent with the number of rings in platform 170. In another embodiment, the sensors can be located on a user or an accessory.

Method 700 can begin at block 701. At block 701, one or more sensors can change from off to on and on to off, when the sensor has a value above a threshold. In an embodiment, the value can be a capacitance or optical value. The threshold can also function as a by-pass filter for sensor capacitances. Each sensor can have an independent threshold value. The threshold value can be adjustable. Threshold values can be adjusted based on a number of variables, for example, the position of sensors in a platform 170, the number of sensors in a platform 170, the size of the sensors in a platform 170, and the size of the activating component activating and deactivating the sensors, for example a user's feet. In an embodiment, the threshold value can determine if a sensor is on or off, providing a direction vector of approximately 22 degrees. In another embodiment, the threshold value as a by-pass filter, wherein only capacitances above the threshold are used in calculating the direction vector and speed vector of approximately 2 to 3 degrees.

At block 702, sensor values or data can be saved. The sensor values can be point-in-time scan values of all sensor data. Sensor data can include, but is not limited to capacitance value, operational state (on or off), historical time values, such as time stamp of last ON event, time stamp of last OFF event. The saved sensor values can be used by computer system 635 to calculate movements by each of the user's feet. The saved sensor values can further be used to historically calculate the user's previous movements to aid in determining the user's actions, for example running, walking, walking backwards, jumping, forward jumping, strafing, and crouching.

At blocks 711 to 712, one or more sensors located in an outer ring can be change from off to on or from on to off. A sensor in an outer ring can be activated to the "on" position by reading a sensor value greater than or equal to the threshold value, for example, one or both of a user's feet moving over a sensor located in an outer ring. A sensor in an outer ring can be deactivated to the "off" position by reading a sensor value less than the threshold value, for example, one or both of a user's feet moving away from a sensor located in an outer ring. At block 713, method 700 can generate "W" or forward in-game movement and method 700 can end.

At blocks 721 to 722, one or more sensors in a middle ring can change from on to off or from on to off. A sensor in a middle ring can be activated to the "on" position by a reading a sensor value greater than or equal to the threshold value, for example, one or more of a user's feet moving over a sensor located in a middle ring. A sensor in a middle ring can be deactivated to the "off" position by reading a sensor value less than the threshold value, for example, one or both of a user's feet moving away from a sensor located in a middle ring.

At block 723, the computer system can check the point-in-time sensor scan of all sensors located in one or more adjacent inner rings of platform 170. At block 724, if one or more sensors are activated, "on," in one or more adjacent inner rings of the same section as the sensor in the middle ring, method 700 can generate "W" or a forward in-game movement and method 700 can end.

At blocks 731 to 732, one or more sensors in an inner ring can change from off to on or from on to off. A sensor in an inner ring can be activated to the "on" position by reading a sensor value greater than or equal to the threshold value, for example, one or more of a user's feet moving over a sensor located in an inner ring. A sensor in an inner ring can be deactivated to the "off" position by reading a sensor value less than the threshold value, for example, one or both of a user's feet moving away from a sensor located in an inner ring.

At blocks 733, the computer system can check the point-in-time sensor scan of all sensors located in one or more adjacent middle rings of platform 170. At block 734, if one or more sensors is activated "on" in one or more adjacent middle rings of a same section as the sensor in the inner ring, method 700 can generate "W" or a forward in-game movement and method 700 can end and method 700 can end.

Method 750 can begin at block 751. At block 751, one or more sensors can change from off to on when the sensor has a value greater than a threshold. In an embodiment, the value can be a capacitance or optical value. Each sensor has an independent threshold value. The threshold value is adjustable. Threshold values can be adjusted based on a number of variables, for example, the position of sensors in a platform 170, the number of sensors in a platform 170, the size of the sensors in a platform 170, and the size of the activating component activating and deactivating the sensors, for example a user's feet. In an embodiment, the threshold value can determine if a sensor is on or off, providing a direction vector of approximately 22 degrees. In another embodiment, the threshold value as a by-pass filter, wherein only capacitances above the threshold are used in calculating the direction vector and speed vector of approximately 2 to 3 degrees.

At block 761, one or more sensors in an outer ring can change from off to on. A sensor in an outer ring can be activated to the "on" position by reading a sensor value greater than or equal to the threshold value, for example, one or both of a user's feet moving over a sensor located in an outer ring. At block 762, method 750 can generate "W" or forward in-game movement and method 700 can end.

At blocks 771, one or more sensors in a middle ring can change from off to on. A sensor in a middle ring can be activated to the "on" position by reading a sensor value greater than or equal to the threshold value, for example, one or more of a user's feet moving over a sensor located in a middle ring. At block 772, method 750 can save sensor data. The sensor values can be point-in-time scan values of one or more sensor data. Sensor data can include, but is not limited to capacitance value, operational state (on or off), historical time values, such as time stamp of last ON event, time stamp of last OFF event. The saved sensor values can be used by computer system 735 to calculate movements by each of the user's feet. The saved sensor values can further be used to calculate, historically, the user's previous movements to aid in determining the user's actions, for example running, walking, walking backwards, jumping, forward jumping, strafing, and crouching.

At blocks 781, one or more sensors in an inner ring can change from off to on. A sensor in an inner ring can be activated to the "on" position by reading a sensor value greater than or equal to the threshold value, for example, one or more of a user's feet moving over a sensor located in an inner ring. At blocks 782, the computer system can check the point-in-time sensor scan of all sensors located in one or more adjacent middle rings of platform 170. At block 783, if one or more sensors is activated "on" in one or more adjacent middle rings of a same section as the sensor in the inner ring, method 750 can generate "W" or forward in-game movement and method 750 can end.

Figure 41:
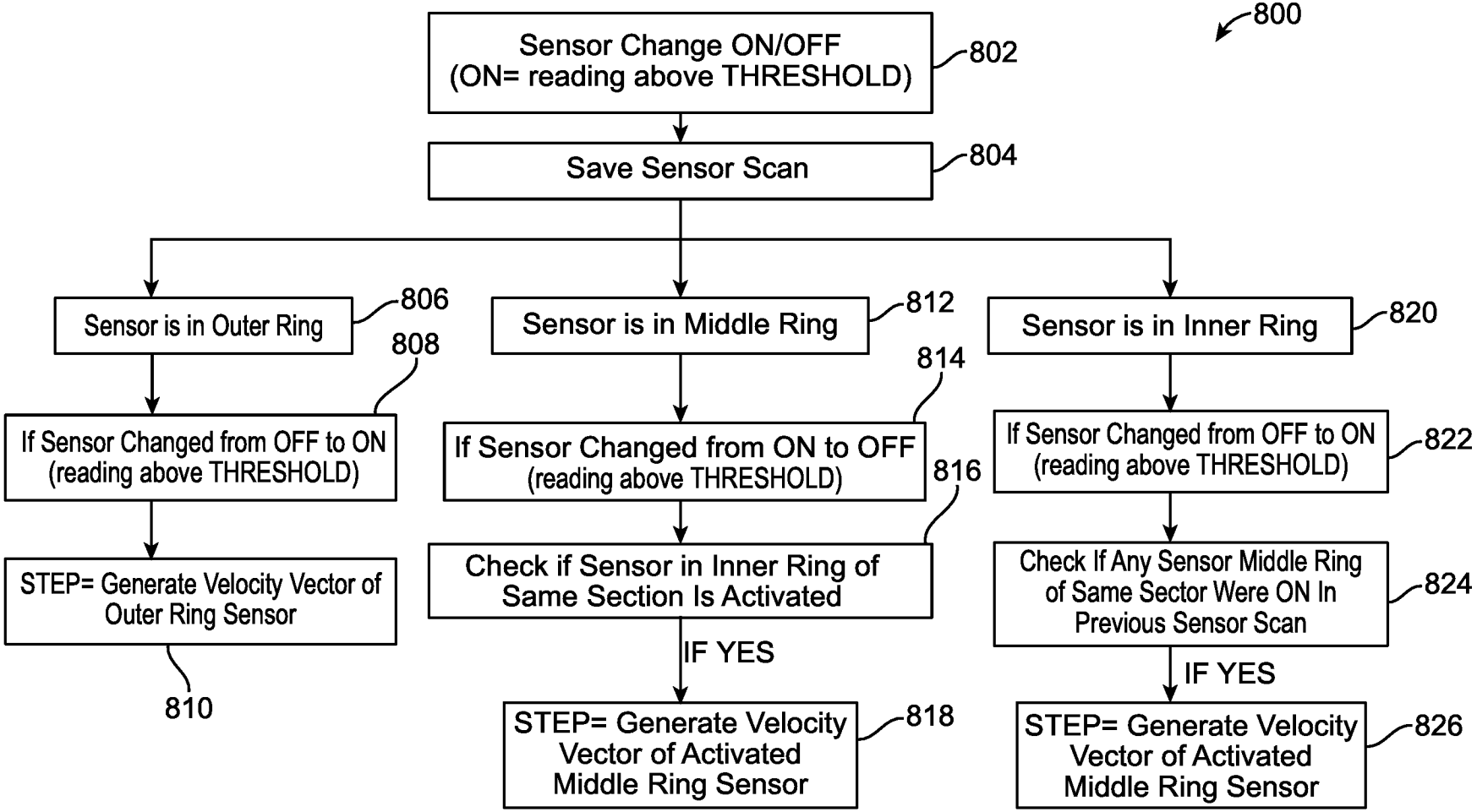
FIG. 41 and FIG. 42 are flow diagrams illustrating example methods for generating a velocity vector using a locomotion system, in accordance with an example embodiment of the present disclosure.
Figure 42:
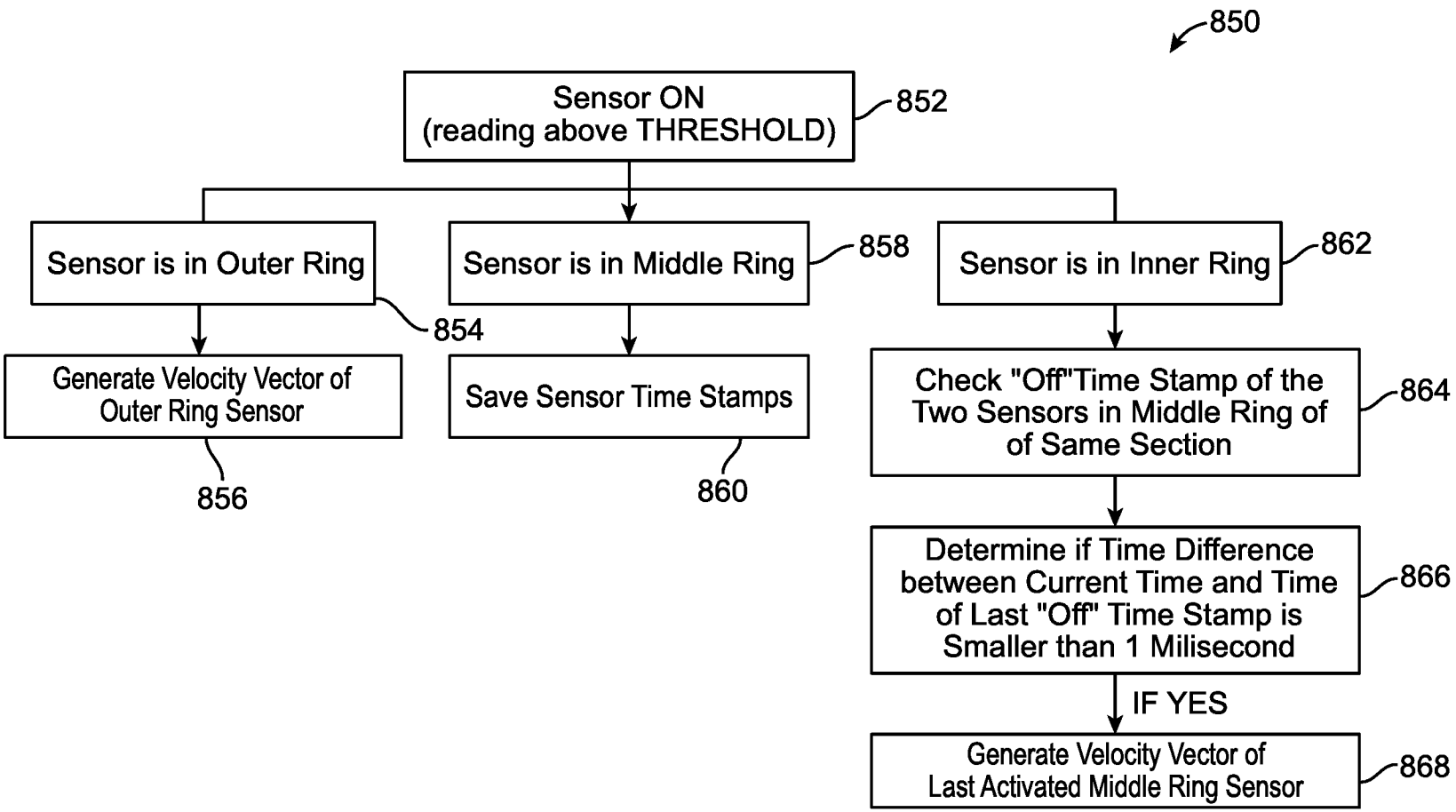

FIG. 41 and FIG. 42 are flow diagrams illustrating an example method 800 and method 850 for generating a velocity vector for representing a direction and speed of a user step. Method 800 and method 850 illustrated in FIG. 41 and FIG. 42 are provided by way of example, as there are a variety of ways to carry out the method. Additionally, while the example methods is illustrated with a particular order of steps, those of ordinary skill in the art will appreciate that FIG. 41 and FIG. 42 and the steps illustrated therein can be executed in any order that accomplishes the technical advantages of the present disclosure and can include fewer or more steps than illustrated.

Each block shown in FIG. 41 and FIG. 42 represents one or more processes, methods or subroutines, carried out in example method. The steps illustrated in FIG. 41 and FIG. 42 can be implemented in at least a system including a platform 170. Each block shown in FIG. 41 and FIG. 42 can be carried out at least by a platform 170. The rings described in FIGS. 41 and 42 are an example representation of three concentric circles for a sensor layout in platform 170. There can be more or less rings depending on the designated sensor layout and therefore method 800 and method 850 can contain more or less branches keeping consistent with the number of rings in platform 170. In another embodiment, the sensors can be located on a user or an accessory.

Method 800 can begin at block 802. At block 802, one or more sensors changes can be detected, for example, a sensor can change from off to on and on to off, when the sensor has a value above a threshold value. In an embodiment, the value can be a capacitance or optical value. The threshold value can also function as a by-pass filter for sensor capacitances. Each sensor can have an independent threshold value. The threshold value can be adjustable. Threshold values can be adjusted based on a number of variables, for example, the position of sensors in a platform 170, the number of sensors in a platform 170, the size of the sensors in a platform 170, and the size of the activating component activating and deactivating the sensors, for example a user's feet. In an embodiment, sensors 615 can include one or more capacitive sensors that register a default capacitance. In another embodiment, registered capacitive changes that occur in excess of the threshold can indicate that the respective sensor has changed state, for example from an "off" to an "on" state, indicating engagement in an associated position on the locomotion system platform 170 and providing a direction vector of approximately 22 degrees. In another embodiment, the threshold value as a by-pass filter, wherein only capacitances above the threshold are used in calculating the direction vector and speed vector of approximately 2 to 3 degrees.

In block 804, a save sensor scan operation is performed in which time data is saved for one or more or all sensor scan data. The sensor values can be point-in-time scan values of one or more sensor data. Sensor data can include, but is not limited to capacitance value, operational state (on or off), historical time values, such as time stamp of last ON event, time stamp of last OFF event. The saved sensor values can be used by computer system 635 to calculate movements by each of the user's feet. The saved sensor values can further be used to historically calculate the user's previous movements to aid in determining the user's actions, for example running, walking, walking backwards, jumping, forward jumping, strafing, and crouching. The time data associated with indications of sensor state changes can be used to calculate velocity vectors from sensor data.

At blocks 806 to 808, one or more sensors located in an outer ring can be changed from off to on or from on to off. A sensor in an outer ring can be activated to the "on" position by reading a sensor value greater than or equal to the threshold value or by a step direction vector method, for example, one or both of a user's feet moving over a sensor located in an outer ring. A sensor in an outer ring can be deactivated to the "off" position by reading a sensor value less than the threshold value or by a step direction vector method, for example, one or both of a user's feet moving away from a sensor located in an outer ring. At block 810, method 800 can generate a velocity vector of an outer ring sensor and method 800 can end.

At blocks 812 to 814, one or more sensors located in a middle ring can be changed from off to on or from off to on. A sensor in a middle ring can be activated to the "on" position by reading a sensor value greater than or equal to the threshold value or by a step direction vector method, for example, one or both of a user's feet moving over a sensor located in a middle ring. A sensor in a middle ring can be deactivated to the "off" position by reading a sensor value less than the threshold value or by a step direction vector method, for example, one or both of a user's feet moving away from a sensor located in a middle ring.

At block 816, the computer system can check the point-in-time sensor scan 804 of all sensors located in one or more adjacent inner rings of platform 170. At block 818, if one or more sensors are activated, "on," in one or more adjacent inner rings of the same section as the one or more sensors in the middle ring, method 800 can generate a velocity vector of the one or more activated middle ring sensors and method 800 can end.

At block 820 to 822, one or more sensors in an inner ring can change from off to on or from on to off. A sensor in an inner ring can be activated to the "on" position by reading a sensor value greater than or equal to the value or by a step direction vector method, for example, one or more of a user's feet moving over a sensor located in an inner ring. A sensor in an inner ring can be deactivated to the "off" position by reading a sensor value less than the threshold value or by a step direction vector method, for example, one or both of a user's feet moving away from a sensor located in an inner ring.

At block 824, the computer system can check the point-in-time sensor scan of all sensors located in one or more adjacent middle rings of platform 170. At block 826, if one or more sensors are activated "on" in one or more adjacent middle rings of a same section as the sensor in the inner ring, method 800 can generate a velocity vector of the one or more activated middle ring sensors and method 800 can end.

Method 850 can begin at block 852. At block 852, one or more sensors can change from off to on when a sensor reads a value greater than a threshold value. Each sensor can have an independent threshold value. The threshold value can be adjustable. Threshold values can be adjusted based on a number of variables, for example, the position of sensors in a platform 170, the number of sensors in a platform 170, the size of the sensors in a platform 170, and the size of the activating component activating and deactivating the sensors, for example a user's feet. In an embodiment, sensors 615 can include one or more capacitive sensors that register a default capacitance. In another embodiment, registered capacitive changes that occur in excess of the threshold can indicate that the respective sensor has changed state, for example from an "off" to an "on" state, indicating engagement in an associated position on the locomotion system platform 170 and providing a direction vector of approximately 22 degrees. In another embodiment, the threshold value as a by-pass filter, wherein only capacitances above the threshold are used in calculating the direction vector and speed vector of approximately 2 to 3 degrees.

At block 854, one or more sensors in an outer ring can change from off to on. A sensor in an outer ring can be activated to the "on" position by a reading over the threshold value or by a step direction vector, for example, one or both of a user's feet moving over a sensor located in an outer ring. In another embodiment, one or more outer ring sensors are activated only following an activation of one or more adjacent middle ring sensors in the same section. At block 856, method 850 can generate a velocity vector of one or more outer ring sensors and method 850 can end.

At block 858, one or more sensors in a middle ring can change from off to on. A sensor in a middle ring can be activated to the "on" position by reading a sensor value greater than or equal to the threshold value or by a step direction vector, for example, one or more of a user's feet moving over a sensor located in a middle ring. At block 860, method 850 can save sensor data and then method 850 can end. The sensor values can be point-in-time scan values of one or more sensor data. Sensor data can include, but is not limited to capacitance value, operational state (on or off), historical time values, such as time stamp of last ON event, time stamp of last OFF event. The saved sensor values can be used by computer system 635 to calculate movements by each of the user's feet. The saved sensor values can further be used to historically calculate the user's previous movements to aid in determining the user's actions, for example running, walking, walking backwards, jumping, forward jumping, strafing, and crouching.

At block 862, one or more sensors in an inner ring can change from off to on. A sensor in an inner ring can be activated to the "on" position by reading a sensor value greater than or equal to the threshold value or by a step direction vector, for example, one or more of a user's feet moving over a sensor located in an inner ring. At blocks 864, the computer system can check the point-in-time sensor scan of one or more of the sensors located in one or more adjacent middle rings in the same section of platform 170. At block 866, if the time difference between the current time of activation of the inner ring sensor and the time of the last "OFF" time stamp of the one or more adjacent middle ring sensors is less than a variable time stamp threshold, for example 1 millisecond, method 850 can generate a velocity vector of one or more middle ring sensors at block 868 and method 850 can end.

The velocity vector generated in FIGS. 41 and 42 can be used to calculate a variety of gaming metrics, for example, speed, direction, walking, running, jumping. The velocity vector output can be (X,Y) coordinates indicating direction and magnitude (speed) of the user's foot or feet.

Velocity vectors can be generated using (X,Y) position coordinates of one or more sensors in which a change is registered, as shown in FIGS. 41 and 42 For example, XY sensor plane of the locomotion system platform 170, can stretch from a designated −1 to 1 distance units in each quadrant of a two dimensional plane. The coordinates can be normalized to facilitate ease of future vector calculations. For example, by dividing the both the X and Y coordinates by normalization factor, in an embodiment $(X^2+Y_2)^{1/2}$. Before velocity vectors are transmitted to computer system 635, MCU 625 can translate the coordinates from a (−1, 1) range to a (0, 255) range.

A vector speed representation can be calculated by multiplying normalized coordinates by a speed value, for example, a value between 0 and 1. The resulting vector "length" can represent the speed. In another embodiment, vector speed calculations can be performed based on a frequency of user steps. In another embodiment, a time interval between activation of consecutive or adjacent sensors can be used to determine the vector speed. For example, using the saved sensor time stamp data.

In an embodiment, a velocity vector calculation can be used to calculate a user jump. For example, using the inner ring sensors and time stamp data of the center sensors to calculate activation and deactivation of the each foot. In another embodiment, the inner, middle and outer sensors can be used to calculate a forward, sideways, and backwards jump.

Figure 43:
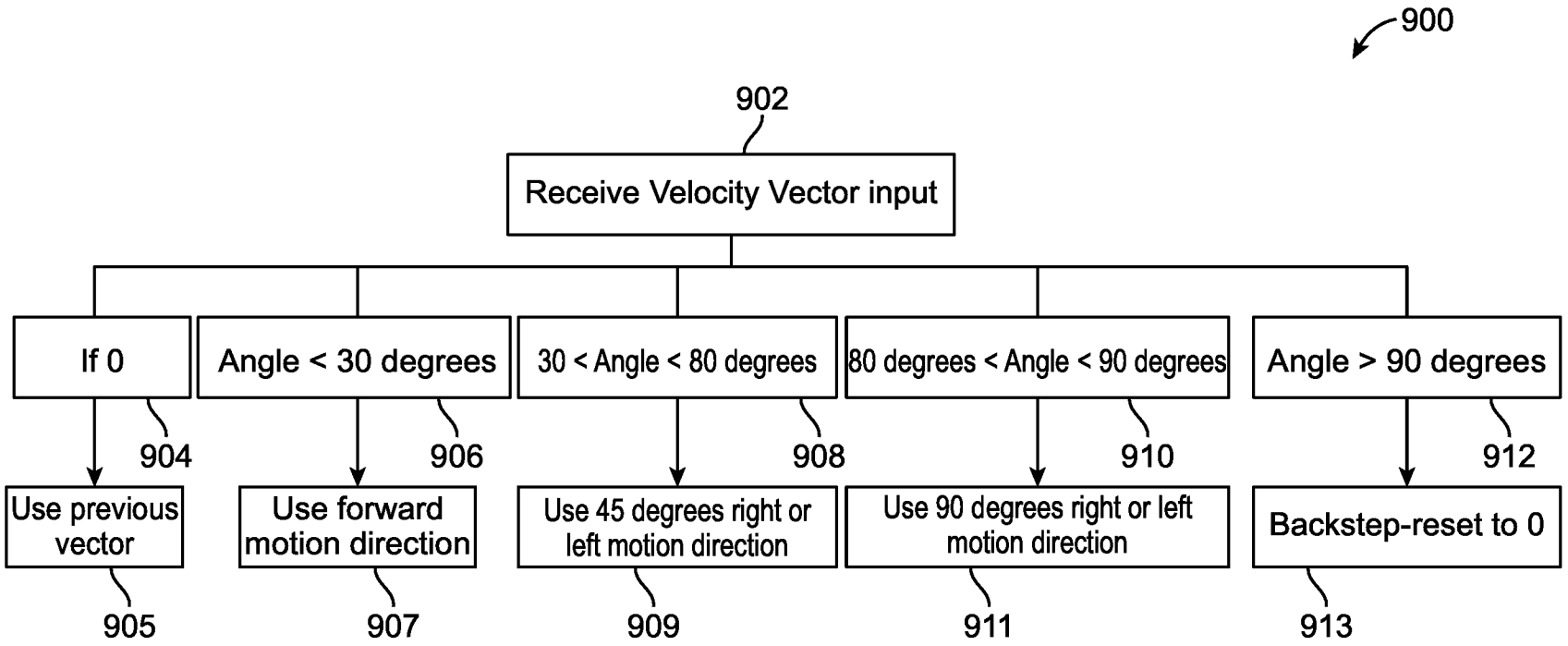
FIG. 43 is a flow diagram illustrating an example method for performing velocity vector integration with third party, in accordance with an example embodiment of the present disclosure.

FIG. 43 illustrates a flow chart of an example method 900 for performing velocity vector integration, with a third party system, for example, a third party gaming system. FIG. 43 is a flow diagram illustrating an example method 900 for velocity vector integration with a third party. Method 900 illustrated in FIG. 43 is provided by way of example, as there are a variety of ways to carry out the method. Additionally, while the example methods is illustrated with a particular order of steps, those of ordinary skill in the art will appreciate that FIG. 43 and the steps illustrated therein can be executed in any order that accomplishes the technical advantages of the present disclosure and can include fewer or more steps than illustrated.

Each block shown in FIG. 43 represents one or more processes, methods or subroutines, carried out in example method. The steps illustrated in FIG. 43 can be implemented in a system including at least platform 170. Each block shown in FIG. 43 can be carried out by at least a platform 170. In another embodiment, the sensors can be located on a user or an accessory.

Method 900 begins at block 902. At block 902 a relative velocity vector input can be received. Subsequently, an angle of the vector input is computed. The angle computed can be the angle measure between the velocity vector direction and absolute north, the front of platform 170. At block 904, if the angle of the velocity vector input is 0, then a previous vector quantity 905 is used. In an embodiment, if after receiving 0 vectors for $1/10^{th}$ second, the vector is reset to 0. At block 906, if the angle of the velocity vector input is less than 30 degrees, the forward motion direction at block 907 is used. At block 908, if the angle of the velocity vector input is between 30 and 80 degrees, a 45 degree motion selection at block 909 is made, for example, in either the left or right direction. At block 910, if the angle of velocity vector input is between 80 and 90 degrees, a 90 degree motion at block 911 selection is made, for example, in either the left or right direction. At block 912, if the angle of the velocity vector input is greater than 90 degrees, a backstep motion at block 913 is made vector is reset to 0.

Current video games use a relative orientation framework. Pushing a joystick to the right or pressing "D" on a keyboard can move a user's avatar 90 degrees to the right from a current viewpoint or camera position. In one embodiment, the current camera position can be obtained by measuring a direction of a head mounted display (e.g., a virtual reality headset). Thus in the relative orientation framework, movement can be relative to the current camera position. To further illustrate, pushing the joystick up or "W" on the keyboard can move the user's avatar in the forward in the current camera position.

In an example embodiment, a game can use an absolute orientation framework (decoupled framework). When a game is played using platform 170, the user's avatar can move independently from the current viewpoint or camera position. The user's avatar can move in an absolute manner relative to an in-game map. For example, if the user walks the direction north on platform 170, the user's avatar can move north on the in-game map, regardless of the current camera position. In a related aspect, the head mounted display can include a magnetometer. The magnetometer can use an absolute orientation framework similar to platform 170, wherein the current in-game camera position can be the direction the user is physically looking outside the game.

In an embodiment, the direction "north" can be magnetic north or polar north. In another embodiment, the direction "north" can be a designated direction set or calibrated at a start of a game. For example, a user wearing a head mounted display, such as a virtual reality headset, can look forward relative to the user's body during calibration, which can calibrate the current forward looking direction with a forward walking orientation prior to decoupling the current camera position and the user's body position. In another embodiment, the halo or harness attached to platform 170, can include sensors to calibrate the forward position of a user with the forward orientation in-game prior to decoupling the current camera position and the user's body position. In another embodiment, upon initiation of a game the current position of the user outside of the game, determined by the sensors in platform 170, the harness, or the headset can be calibrated to the starting position of the game. For example, if an avatar is initiated facing east, then the direction the user is facing when the game is initiated can be calibrated east.

In an example embodiment, decoupling can be implemented in existing games. Existing games are not set up for decoupling, however the decoupling effect can still be achieved by generating one or more keystrokes based on the user's current camera position. For example, if the user walks forward on the platform 170 while looking 90 degrees to the left, decoupling can be accomplished by generating the "D" key or left movement key. The absolute orientation framework can be converted to the relative orientation framework by taking into account the current camera direction. In another example, if the user walks forward on the platform 170 while looking 45 degrees to the right, achieving the decoupling effect can be accomplished by generating the "W" and "A" keys simultaneously or in an alternating manner. In yet another example, if the user walks forward on the platform 170 while looking 15 degrees to the right, achieving the decoupling effect can be accomplished by generating the more "W" keys than "A" keys.

Figure 44:
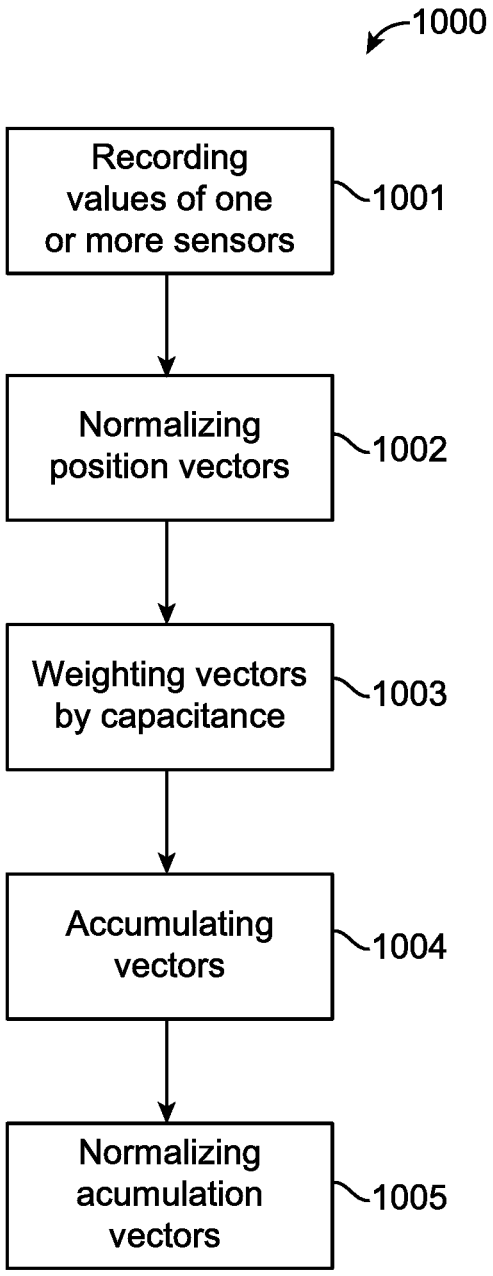
FIG. 44 is a flow diagram illustrating an example method of calculating a velocity vector, in accordance with an example embodiment of the present disclosure.

In an embodiment, the sensors can monitor directions of a user's left foot and right foot to determine the user's intended movement direction. FIG. 44 illustrates an example algorithm for determining a step direction. In an embodiment, four active sensors can be physically located on one or more slices of platform 170, for example, the sensors are located in slice 601 and rings 611 and 612. The four active sensors can represent all non-zero sensors in the outer two sensor rings. Each of the four active sensors can have a position vector value and a capacitance value. A threshold can be used to filter out sensor capacitance readings below pre-defined threshold value. This can reduce the noise in determining a single step is completed. For example, if the threshold value is specified as a capacitance value of 0.50, then only sensors having a reading of greater than 0.50 can be used is determining the step direction. In another embodiment, the active sensors can be physically located on a user's feet, hands, torso, head, or an accessory, for example a gun, sword, baton, paddle, or bat.

FIG. 44 illustrates a flow chart of an example method 1000 for determining a user's intended movement direction. FIG. 44 is a flow diagram illustrating an example method 1000 for determining a user's intended movement direction. Method 1000 illustrated in FIG. 44 is provided by way of example, as there are a variety of ways to carry out the method. Additionally, while the example methods is illustrated with a particular order of steps, those of ordinary skill in the art will appreciate that FIG. 44 and the steps illustrated therein can be executed in any order that accomplishes the technical advantages of the present disclosure and can include fewer or more steps than illustrated.

Each block shown in FIG. 44 represents one or more processes, methods or subroutines, carried out in example method. The steps illustrated in FIG. 44 can be implemented in at least a system including a platform 170. Each block shown in FIG. 44 can be carried out by at least a platform 170. In another embodiment, the sensors can be located on the user or accessory.

Method 1000 can begin at block 1001. At block 1001, one or more sensors can be activated by recording a measurement. In an embodiment, sensors on platform 170 can be activated by recording a capacitance measurement. For example, if a user steps forward to the outer two rings of slice 601, the four sensors in rings 611 and 612 can have capacitance readings. If the capacitance readings of the sensors are greater than a predefined threshold, the capacitance readings can be used to calculate the step direction. In an embodiment all sensor readings greater than zero can be used in calculating the step direction. In another embodiment, sensors can be activated by recording an inertial measurement or optical measurement. When a sensor value has been recorded at one or more sensors, the method can proceed to block 1002.

At block 1002, the active sensors with a recorded value greater than or equal to threshold can be normalized. During the normalization process, the position of one or more sensors can be converted to one or more direction vectors. For example, if the active sensors are in slice 601, the normalized direction vectors can be in the direction of slice 601. When the normalization of the sensor positions has completed, the method can proceed to block 1003.

At block 1003, weighted vectors can be calculated for the normalized position vectors. In an embodiment, the weighted vectors by capacitance can be calculated. For example, sensors with a greater capacitance reading can be assigned a higher weight. In an embodiment the weight of each active sensor is calculated by multiplying the normalized position vectors by the sensor capacitance values. When the vectors have been weighted the method can move to block 1003.

At block 1004, the weighted vectors can be accumulated to calculate an accumulated vector. For example, the directionally weighted vectors can be added together to calculate an accumulated vector. When an accumulated vector has been calculated the method can move to block 1005.

At block 1005, the accumulated vector can be normalized. For example, normalizing the accumulated vector can determine the step direction vector. When the accumulated vectors have been normalized and the step direction vector created method 1000 can end.

Figure 45:
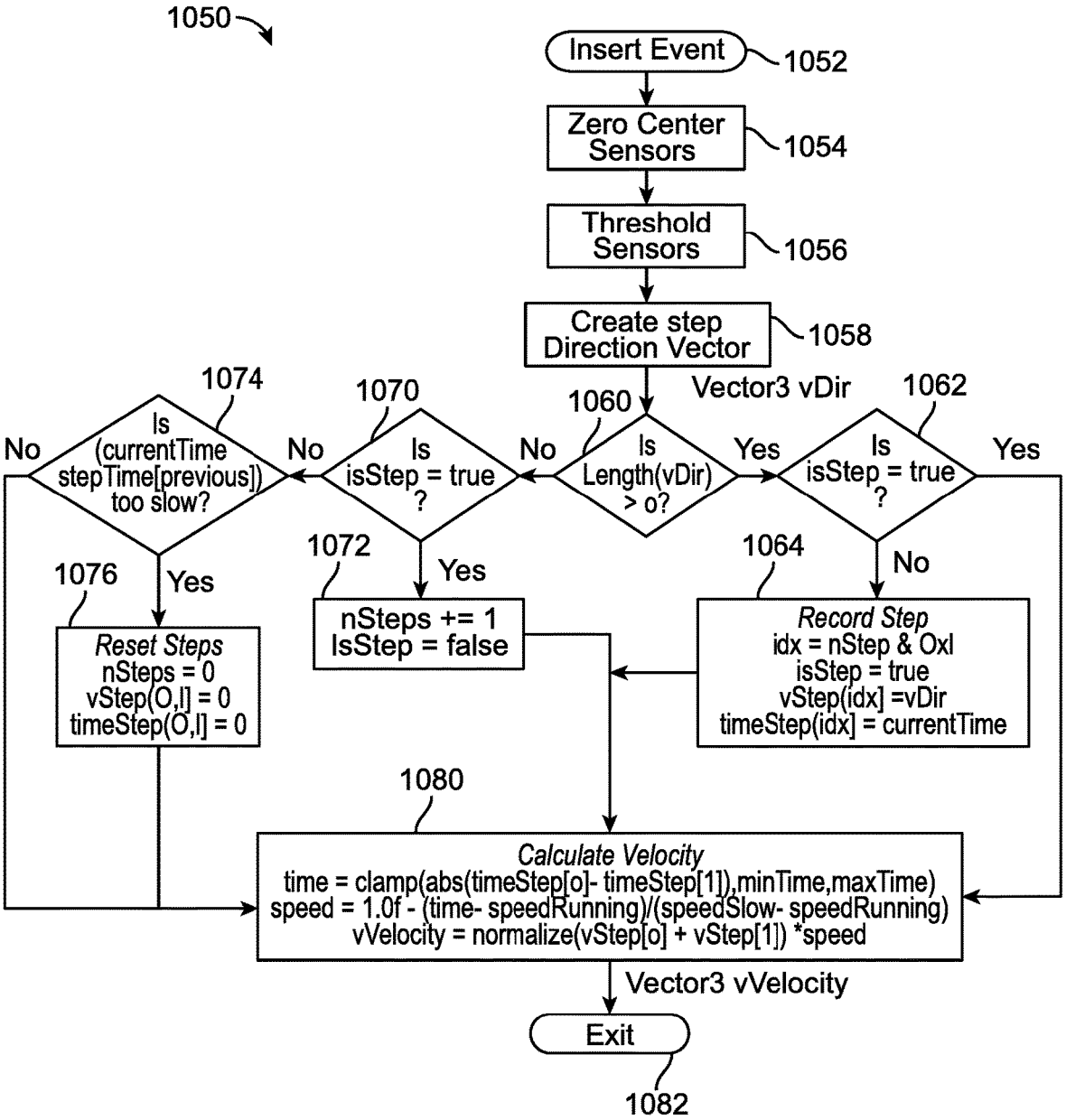
FIG. 45 is a flow diagram illustrating an example method for calculating a velocity, in accordance with an example embodiment of the present disclosure.

FIG. 45 is a flow diagram illustrating an example method 1050 for determining a user's intended movement direction. In another embodiment the method can track two-step direction vectors and calculate the velocity direction as the average of the two vectors. The method can determine a velocity for a user's character movement based on even and odd step direction vectors and step time stamps, for example, averaging direction vectors and monitoring step rate. The method can store a set of internal or global data structures, for example: Vector3, Float, Int, Bool, vStep[2], timeStep[2], nSteps, and is Step.

Method 1050 illustrated in FIG. 45 is provided by way of example, as there are a variety of ways to carry out the method. Additionally, while the example methods is illustrated with a particular order of steps, those of ordinary skill in the art will appreciate that FIG. 45 and the steps illustrated therein can be executed in any order that accomplishes the technical advantages of the present disclosure and can include fewer or more steps than illustrated.

Each block shown in FIG. 45 represents one or more processes, methods or subroutines, carried out in example method. The steps illustrated in FIG. 45 can be implemented in at least a system including a platform 170. Each block shown in FIG. 45 can be carried out by at least a platform 170. In another embodiment, the sensors can be located on the user or accessory.

Method 1050 can begin at block 1052. At block 1052 an event can occur, for example, a current time, position an inertial, optical or capacitance measurement of one or more sensors. When an event has occurred, the method can proceed to block 1054. At block 1054, the sensors can be zeroed. In an embodiment, the sensors in a center zone of platform 170 can be zeroed. In an embodiment, the center zone can be the inner two rings of platform 170. In another embodiment center zone can a geometric shape, a circle, hexagon or octagon. When the sensors have been set to zero, method 1050 can proceed to block 1056.

At block 1056, a threshold can be used to filter active sensors. In an embodiment, a threshold can be used to filter active sensors based on capacitance, optical measurements, or inertial measurements. For example, if the capacitance readings of the active sensors are greater than a predefined threshold, the active sensor can be included in the velocity calculation. In an embodiment the threshold can be set to zero. When the active sensors with a capacitance reading greater than or equal to threshold value are determine, the method can proceed to block 1058. At block 1058, a step direction vector is calculated. For example, the step direction vector can be calculated using method 1000. When the step direction vector is calculated method 1050 can proceed to block 1060.

At block 1060, the length of the direction vector is determined. If the length of the direction vector is greater than zero, method 1050 can proceed to a block 1062. At block 1062, it is determined if a user has taken a step. For example, an active sensor reading outside of the center zone can be a confirmation of a step. If it is determined a step was taken, method 1050 can proceed to a block 1080. At block 1080 the velocity can be calculated. In an embodiment, the velocity can be a vector which is the average of two-step direction vectors multiplied by the step rate or speed. In the same embodiment, the magnitude of the velocity vector is the user speed. A zero length vector can mean the user is stopped. A vector length between 0 and 1 can mean the user is walking or running. A vector length of 1 can mean the user is running. The velocity can be calculated, in an embodiment, using Equations (1)-(3).

time=clamp(abs(timeStep[0]−timeStep[1]),minTime, maxTime) Equation (1)

speed=1.0f−(time−speedRunning)/(speedSlow−speed-running) Equation (2)

vVelocity=normalize(vStep[0]+vStep[1])*speed Equation (3)

Once the velocity is calculated at block 1080, the method can proceed to block 1082 and end.

If at block 1062 a step was not taken, the method can proceed to block 1064. At block 1064, a step is recorded. For example, the direction vector has a length greater than zero (block 1060) and the sensors in center zone were zeroed out (block 1054), therefore a foot has moved to the outer sensors. When a step is recorded, method 1050 can move to block 1080 to calculate a velocity. Once the velocity is calculated at block 1080.

If at block 1060, the length of the direction vector is equal to or less than zero, method 1050 can proceed to a block 1070. At block 1070, it is determined if a user has taken a step. For example, an active sensor reading outside of the center zone, a step has been taken. If it is determined a step was taken, method 1050 can proceed to a block 1072. At block 1072, the number of steps is incremented and a step variable is set to false. For example, there was in a step (foot in outer sensors) and now there is no foot detected in the outer sensors, thus step is complete. After the step is completed, method 1050 can proceed to block 1080.

If at block 1070, a step was not taken, the method can proceed to block 1074. At block 1074, it can be determined if step was too slow. In an embodiment, if a foot stayed in an outer zone of platform 170. In an embodiment, a step being too slow can be determined by subtracting the current time from the previous step time and then determining if the calculated value is greater or less than a step threshold value. If the step is too slow then method 1050 can proceed to block 1076. At block 1076, the steps values are reset. For example, number of steps, step vector and step time can be set to zero. When the step values are set to zero method 1050 can proceed to block 1080. If at block 1074 a step was not too slow, method 1050 can proceed to block 1080.

Figure 46A:
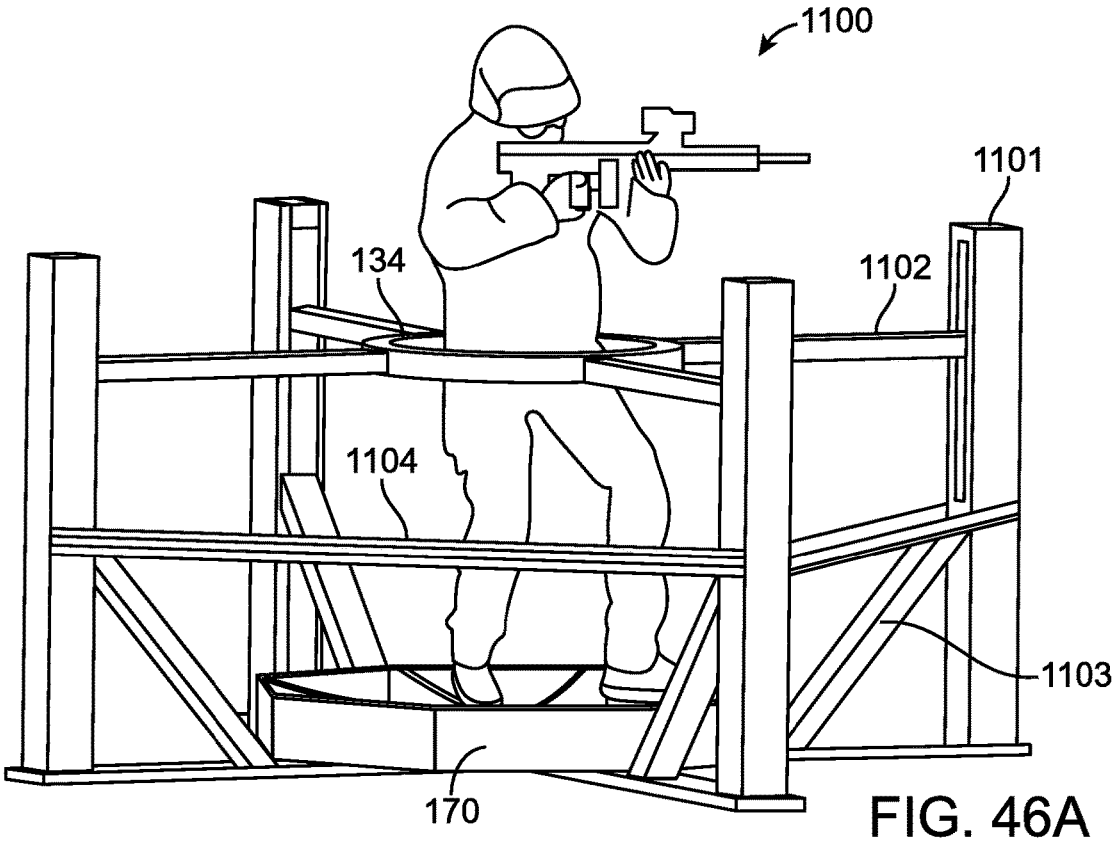
FIG. 46A, FIG. 46B and FIG. 46C illustrate an example locomotion system used for industrial applications, in accordance with an example embodiment of the present disclosure.
Figure 46B:
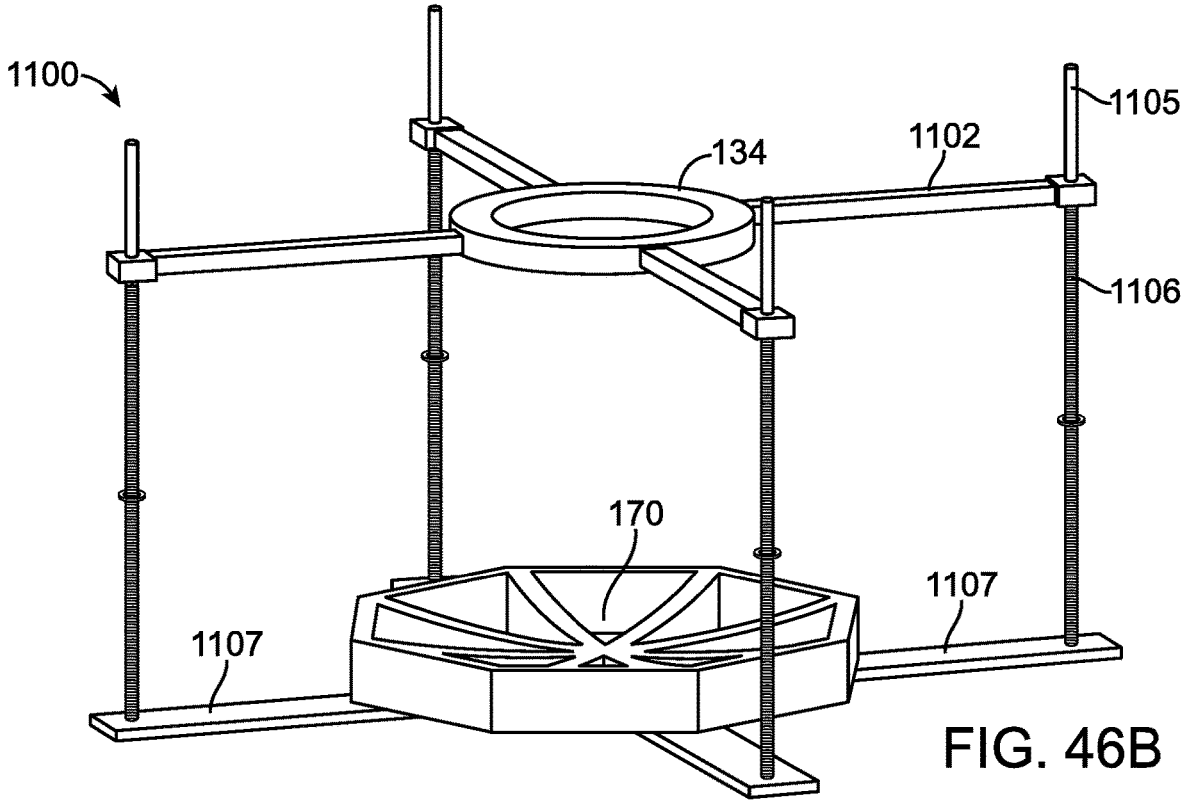
Figure 46C:
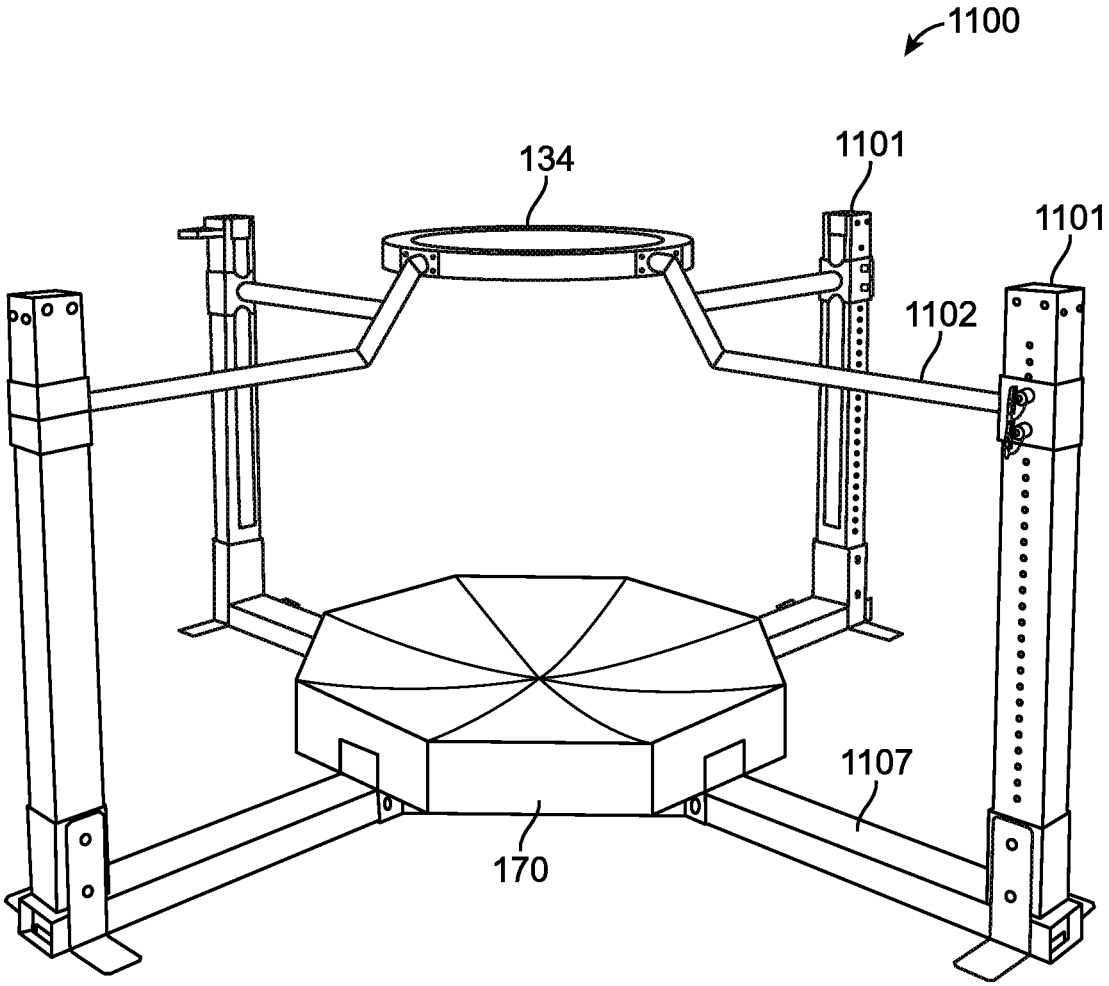

FIGS. 46A, 46B, and 46C illustrate an example industrial omnidirectional locomotion system. Industrial omnidirectional locomotion system 1100 can comprise vertical supports 1101, horizontal struts 1102, halo 134, support members 1103 and 1104, platform 170, vertical poles 1105, springs 1106, ground supports 1107 and a linear ball bearing system (not shown).

Vertical supports 1101 can enable vertical movement of halo 134. In an embodiment, vertical supports 1101 can be hollow to enable entry of horizontal struts 1102 and coupling to vertical poles 1105 by a linear ball bearing system. Vertical supports 1101 can be of variable length. Vertical supports 1101 can also include a protective covering. The protective covering can prevent foreign materials from entering the hollow portion of Vertical supports 1101 and thus prevent foreign materials from interfering with linear ball bearing system, pole 1105 and springs 1106. For example, the protective covering can be overlapping bristles. In an embodiment, the vertical supports 1101 are far enough away from the center support to prevent interference with a user and any industrial gear, for example a gun, sword, baton, paddle, racquet. Vertical supports 1101 can keep vertical poles 1105, vertical for example, 90 degree angle, to enable consistent vertical movement from the user. Horizontal struts 1102 extend from halo 134 and attached to the vertical poles 1105 by a ball bearing system. The ball bearing system can enable vertical movement of halo 134. In another embodiment, horizontal struts 1102 can also extend at an acute angle, for example, 75 degrees, 45 degrees, or any other angle less than 90 degrees, as shown in FIG. 46C. A more acute angle can enable an industrial user unobstructed use of an industrial firearm, for example pointing the barrel on the gun towards the ground. In an embodiment, the ball bearing system can have greater than 5 inches of contact with the vertical poles. The linear ball bearing system can comprise a linear ball bearing block. The liner ball bearing system can enable a smoother movement of the struts 1102 along the vertical poles. Horizontal struts 1102 can extend from halo 134 in the same plane. Support members 1103 and 1104 can add stability to vertical supports 1101. Ground support 1107 can support and stabilize industrial omnidirectional locomotion system 1100.

Springs 1106 can raise the halo 134 and struts 150 when a user is in the standing position. Springs 1106 can provide support during forward user movements. Springs 1106 can further compress enabling a user to crouch, and aid a user in standing, standing up from a crouch, or jumping by uncompressing. The spring constant can be calculated, in an embodiment, using Hooke's Law. The total force can be the weight of the halo can be added to the upward force needed to provide stability for a user. The stability can differ depending on the height of a user. The total force can be divided by the number of vertical supports. In an embodiment, the spring constant can be between 0.2 lb/in and 4.0 lb/in. In another embodiment, the spring constant can be between 0.4 lb/in and 2.0 lb/in.

In an embodiment, vertical supports can include telescoping poles. In another embodiment vertical supports are telescoping poles. For example, the height of the vertical supports/telescoping poles will be the same height as halo. The telescoping pole can enable a user to move vertically by compressing and extending in response to the user's movements.

In an embodiment, the vertical supports can be a bungee cord or suspended spring system. In this embodiment, a minimal resistance would be applied to the halo when a user is in the crouch position. Upon a user moving to the stand position from the crouch position, the resistance on the halo would subside. In another embodiment, vertical movement can be achieved by a pivot arm system. A pivot can be attached to the struts on either the vertical support or the halo. Upon a user moving to the crouch or stand position, the pivots can actuate enabling the vertical movement of the user. In another embodiment, vertical movement can be achieved by a magnetic levitation system. The struts can be attached to the vertical support by magnets. The magnetic field created by the magnetic polarization can enable vertical movement. In another embodiment, vertical movement can be achieved by hydraulic actuation. The horizontal struts can be attached to the vertical supports by hydraulics. Vertical movement of the user can be actuated by the hydraulics. In another embodiment, vertical movement can be achieved by compressed gas. Vertical movement can be achieved by actuating a regulator causing the release and restriction of the flow of compressed gas.

Figure 47:
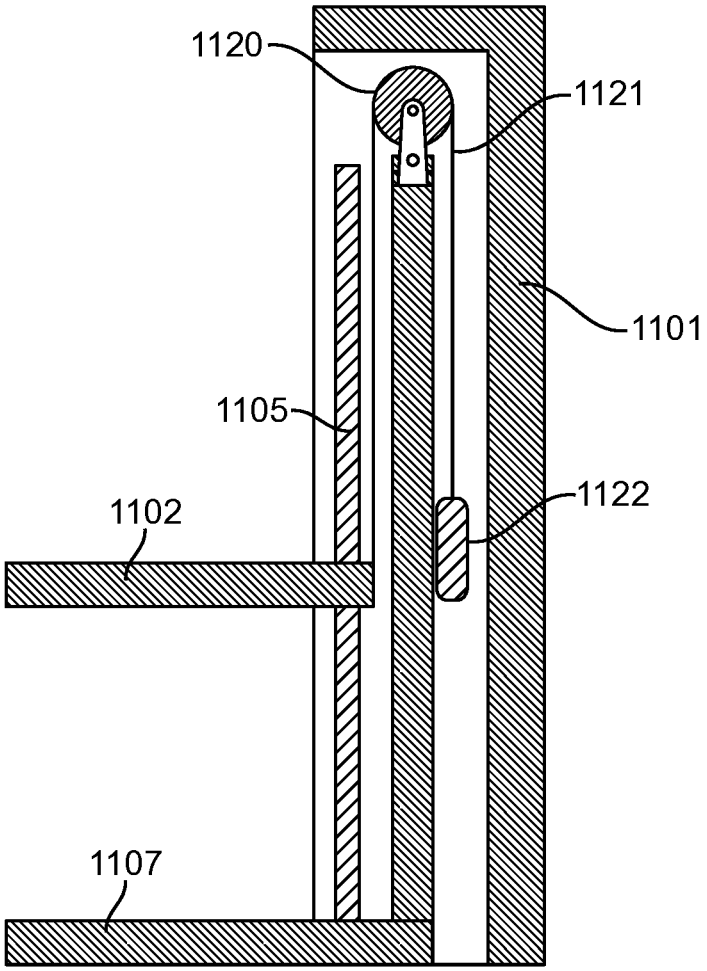
FIG. 47 is a cross-sectional view illustrating an example pulley system of the locomotion system, in accordance with an example embodiment of the present disclosure.

FIG. 47 is a cross-sectional view illustrating a pulley braking system of an industrial omnidirectional locomotion system. A pulley system 1120 can connect a mass 1122 to a linear bearing system (not shown) by a cable 1121. The mass 1122 can enable the linear bearing system to move vertically along a vertical pole 1105. The mass can provide a constant upward horizontal force to the horizontal struts 1102 and halo (not shown). The constant upward horizontal force can counteract the constant downward force produced when a user is moving forward, for example walking or running. In the previous and subsequent embodiments, the forward force can also be a backward force, for example, a user walking for running backward.

Figure 48:
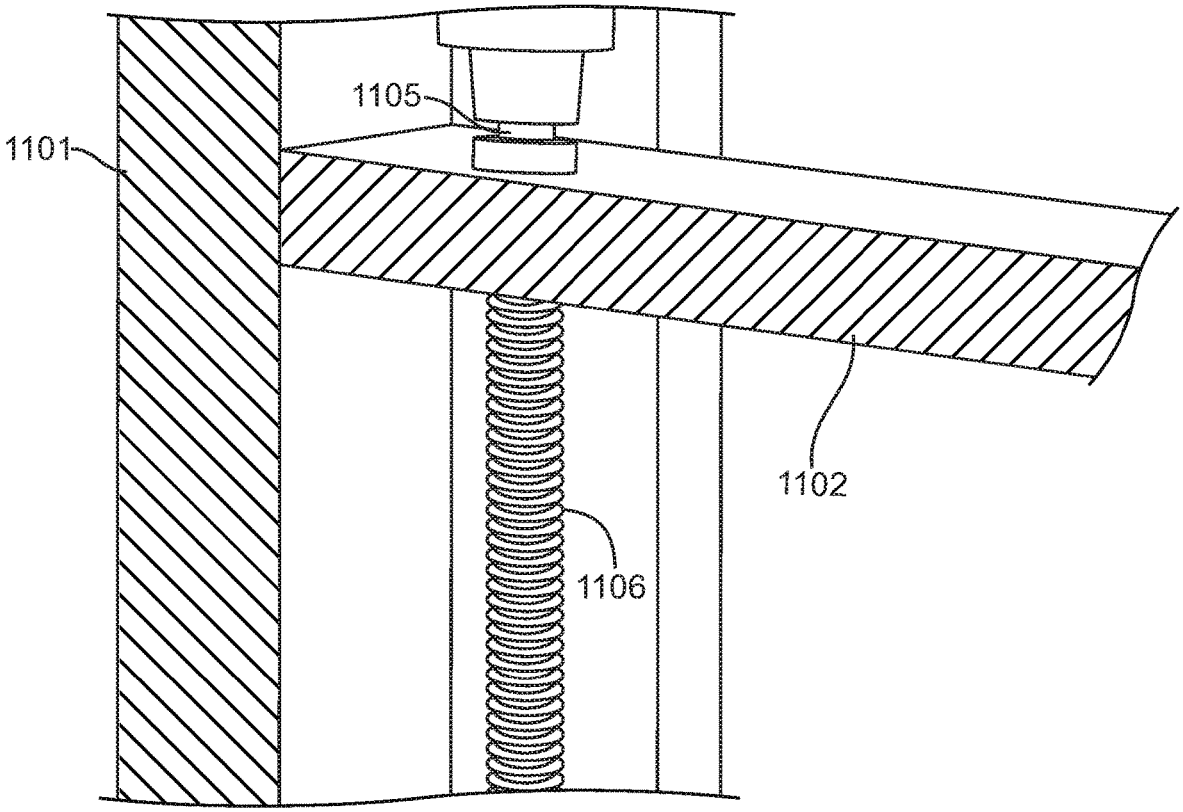
FIG. 48 is a cross-sectional view illustrating an example of a counterweight system of the locomotion system, in accordance with an example embodiment of the present disclosure.

FIG. 48 is a cross-sectional view illustrating a counter weight system braking system of an industrial omnidirectional locomotion system. A counterweight system can aid in preventing a user from falling. In an embodiment, the counterweight system can comprise vertical supports 1101, vertical poles 1105, and one or more springs 1106 used to create a restorative force to resist horizontal force provided by the user. The springs 1106 can be placed underneath a linear bearing system (not shown). The springs 1106 can compress due to downward horizontal force, produced by a user forward movement, which can also produce a balancing upward force, for example if a user is walking or running.

Figure 49:
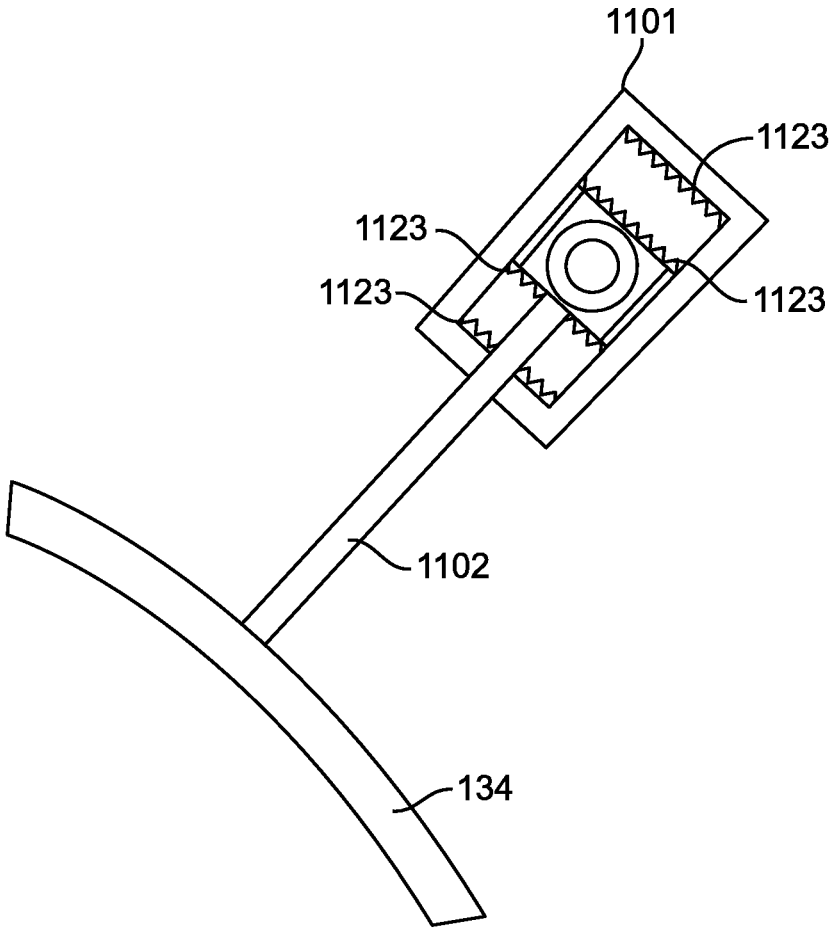
FIG. 49 is a top view illustrating an example braking system of the locomotion system, in accordance with an example embodiment of the present disclosure.

FIG. 49 is a top view illustrating a frictional force braking system of an industrial omnidirectional locomotion system. The forces produced by a forward movement of a user can be converted into a frictional force that can resist the vertical force of a falling user. The frictional force can counteract the constant downward force produced by a forward movement of a user, for example running. In an embodiment, the frictional force is created by a frictional material 1123 internal to the vertical supports 1101 and the bearing system (not shown). When a user moves forward the frictional material on the outside of the bearing system comes into contact with the frictional material internal to the hollow supports creating a frictional force.

Figure 50:
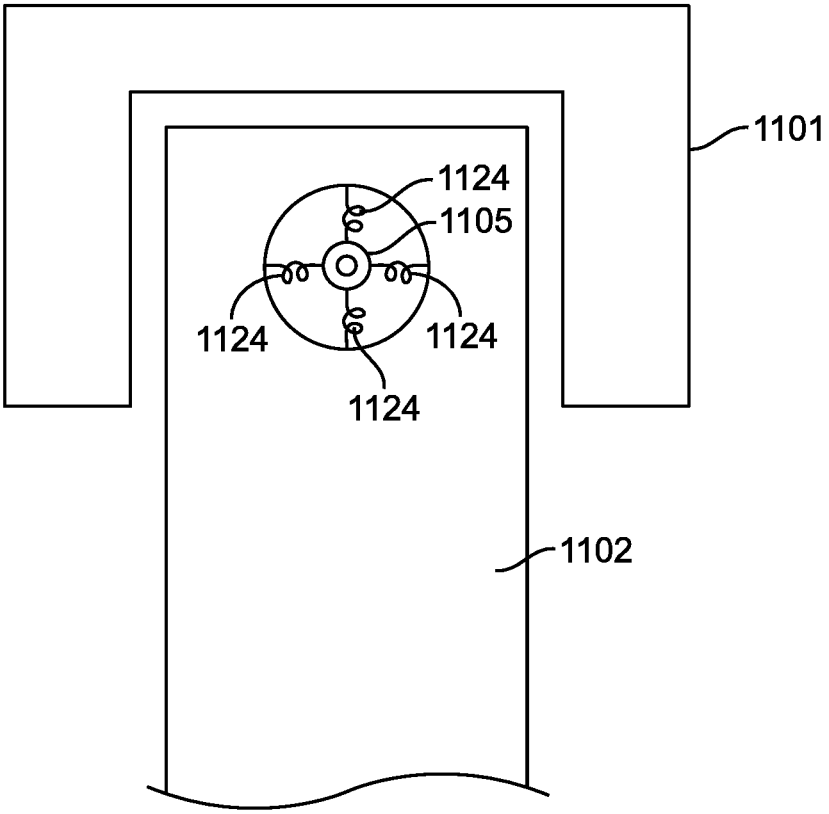
FIG. 50 is a top view illustrating an example braking system of the locomotion system, in accordance with an example embodiment of the present disclosure.

FIG. 50 is a top view illustrating a circumferential spring braking system of an industrial omnidirectional locomotion system. The linear ball bearing system can be attached to the vertical pole by one or more springs 1124. In an embodiment, four springs 1124 are set equidistant and creating a 90 degrees with the vertical pole 1105. When a forward movement is applied by the user to the horizontal strut 1102, the horizontal force is transferred from the user through the horizontal strut 1102 and to the springs 1124. When the springs compress, the frictional material on the outside of the linear ball bearing system and internal to the hollow support come into contact creating a frictional force. The frictional force can resist the downward force produced by the forward movement of the user, preventing a fall. In another embodiment, the frictional force can come from the contact of the strut and the linear bearing system.

Figure 51:
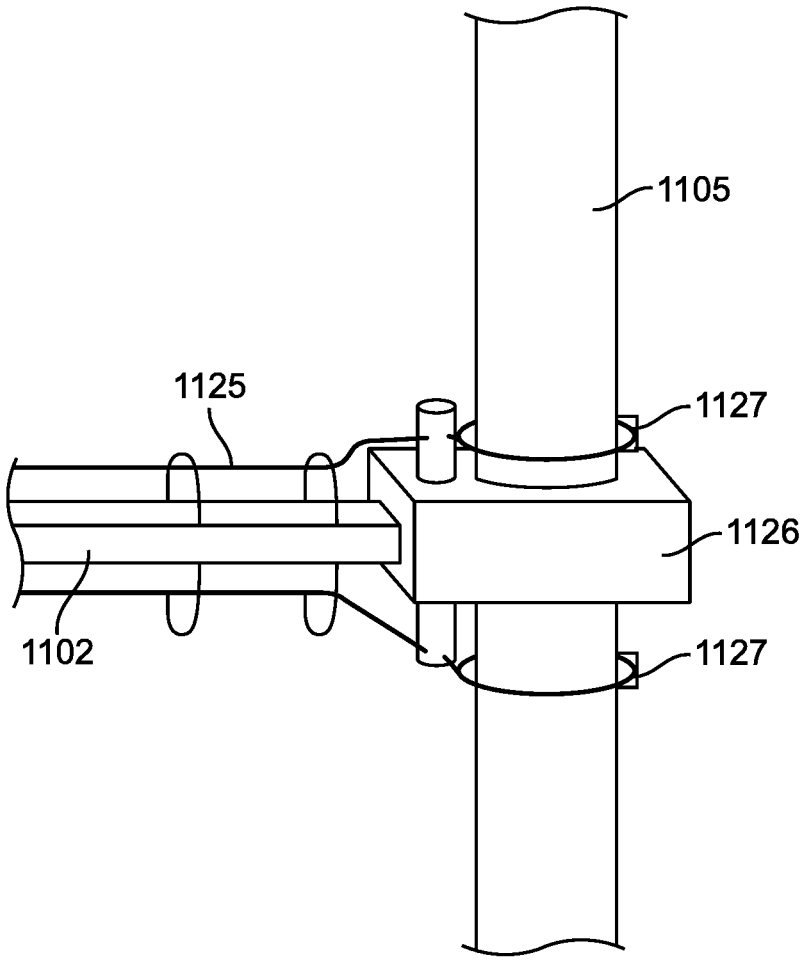
FIG. 51 is a side view illustrating an example braking system of the locomotion system, in accordance with an example embodiment of the present disclosure.

FIG. 51 illustrates a cable braking system of an industrial omnidirectional locomotion system. A cable braking system can be used to prevent a user from falling. The cable braking system can include brakes 1127, brake cables 1125 that run along the horizontal struts 1102, and a ball bearing sleeve 1126 which houses the bearing system. The forward movement of a user can create a horizontal force. The horizontal force can actuate and increase the tension on brake cables 1125 actuating the brakes 1127. For example, the increased tension on the cable brake system can provide a frictional force along the vertical pole, resisting the downward force produced by a user's forward movement, for example walking or running.

Figure 52:
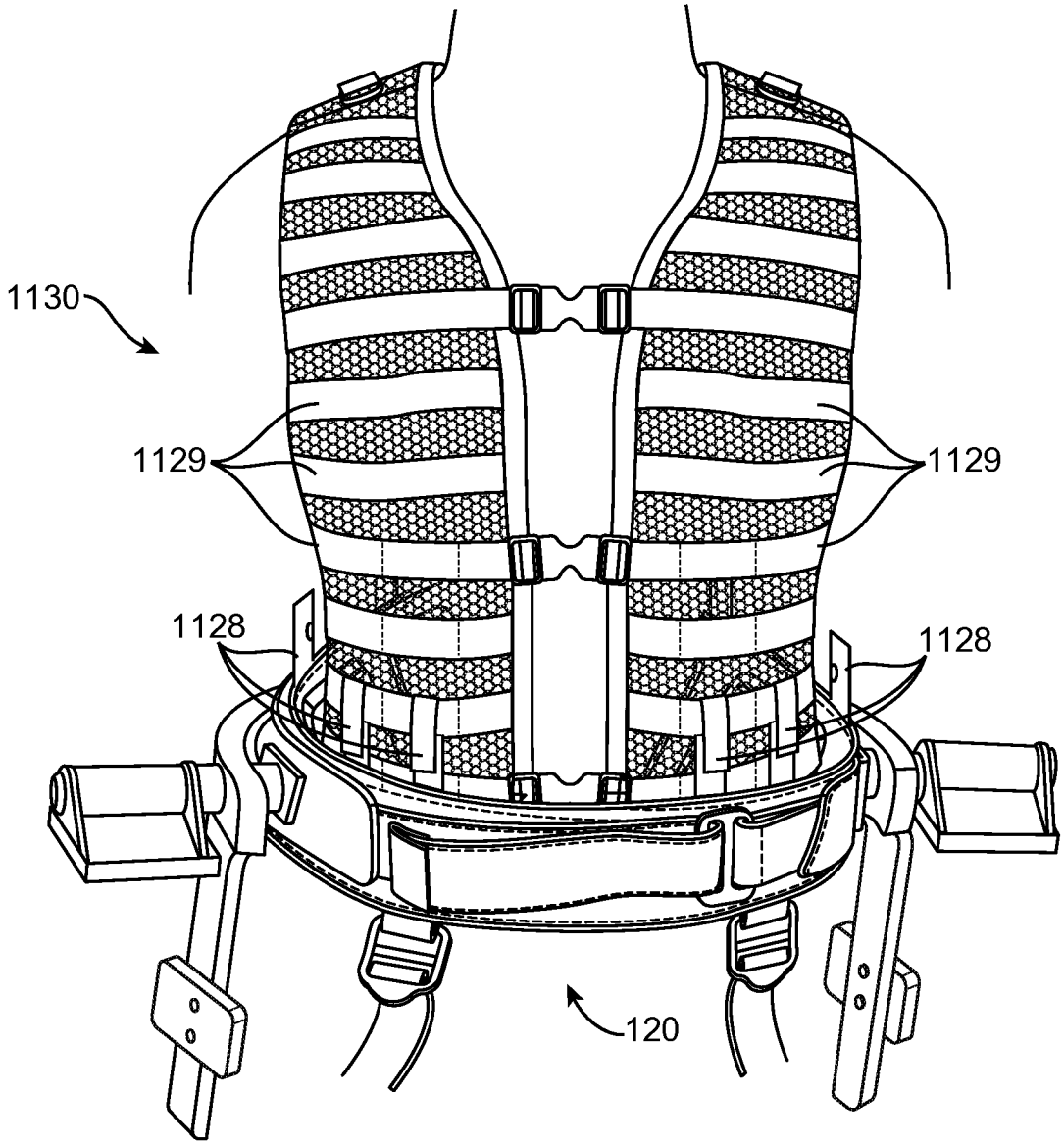
FIG. 52 illustrates an example MOLLE and PALS harness connection, in accordance with an example embodiment of the present disclosure.

FIG. 52 illustrates a Pouch Attachment Ladder System (PALS) and a modular lightweight load-carrying equipment (MOLLE) harness connection. Standard industrial load bearing equipment can be integrated to the harness 120. In an embodiment, MOLLE personal protective equipment with PALS 1130 can be integrated, as shown in FIG. 52. In another example, a MOLLE patrol pack with PALS can be integrated. The PALS system consists of a webbing grid 1129 for connecting PALS compatible equipment. Any other industrial gear or attire, for example, improved load bearing equipment (ILBE), can also be integrated into the locomotion system harness. Harness 120 can have one or more PALS compatible straps 1128 for integration with industrial equipment, for example MOLLE or ILBE. Compatible straps 1128 can be attached to the MOLLE person protective equipment 1130, the MOLLE patrol pack, the ILBE equipment by the PALS system.

Embodiments described herein comprise a combination of features and advantages intended to address various shortcomings associated with certain prior devices, systems, and methods. The foregoing has outlined rather broadly the features and technical advantages of the invention in order that the detailed description of the invention that follows may be better understood. The various characteristics described above, as well as other features, will be readily apparent to those skilled in the art upon reading the detailed description, and by referring to the accompanying drawings. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

Examples within the scope of the present disclosure can also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be utilized to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in standalone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other examples of the disclosure can be practiced in network computing environments with many types of computer system configurations, including personal computers, handheld devices, multi-processor systems, microprocessor-based or programmable consumer electronics, network PCs, minicomputers, mainframe computers, and the like. Examples can also be practiced in distributed computing environments where tasks are performed by local and remote processing devices that are linked (either by hardwired links, wireless links, or by a combination thereof) through a communications network. In a distributed computing environment, program modules can be located in both local and remote memory storage devices.

The various examples described above are provided by way of illustration only and should not be construed to limit the scope of the disclosure. For example, the principles herein apply not only to a smartphone device but to other devices capable of detecting communications such as a laptop computer. Those skilled in the art will readily recognize various modifications and changes that can be made to the principles described herein without following the example embodiments and applications illustrated and described herein, and without departing from the scope of the disclosure.

We claim:

1. A method of generating an input for controlling an application from movement within a *concave* platform of an omnidirectional locomotion system configured to support a user on the *concave* platform, the method comprising:

receiving, from at least two or more sensors, movement data from movement within the *concave* platform configured to support the user on the *concave* platform;

calculating, at a processor, a velocity from the movement data;

calculating, at the processor, a heading from the movement data;

translating, at the processor, the velocity and the heading into [2-dimensional Cartesian coordinates] *at least one of a forward, backwards, or sideways movement input values*;

normalizing, at the processor, the [2-dimensional Cartesian coordinates] *at least one of a forward, backwards, or sideways movement input values* into a minimum to maximum scale range; and transmitting, the normalized [coordinates] *movement input values* as the input for controlling the application.

2. The method of claim 1, wherein the velocity is calculated by a distance a foot of [a] *the* user travels divided by the time it took to travel the distance.

3. The method of claim 1, wherein the velocity is calculated by a pedometry rate.

4. The method of claim 3, wherein the pedometry rate is determined by monitoring a frequency of steps over a predefined interval.

5. The method of claim 1, wherein the velocity is calculated by monitoring an acceleration of a foot of [a] *the* user.

6. The method of claim 1, wherein the velocity is calculated by normalizing an angular velocity.

7. The method of claim 6, wherein the angular velocity is a change in rotation of a foot of [a] *the* user.

8. The method of claim 1, further comprising:

translating, at the processor, the heading relative to a real world axis.

9. The method of claim 8, wherein the real world axis is magnetic North.

10. The method of claim 9, further comprising:

calibrating, at the processor, the magnetic North to an initial orientation of [a] *the* user by an offset.

11. The method of claim 1, further comprising:

translating, at the processor, the heading relative to an orientation of a torso of [a] *the* user.

12. The method of claim 1, further comprising:

translating, at the processor, the heading relative to an orientation of a head of [a] *the* user.

13. The method of claim 1, wherein the minimum to maximum scale range is defined by gaming input descriptors.

[14. The method of claim 1, wherein a Y 2-dimensional Cartesian coordinate is for forward or backwards movement.]

[15. The method of claim 1, wherein an X 2-dimensional Cartesian coordinate is for sideways movement.]

16. The method of claim 1, where the two or more sensors are located within the *concave* platform.

17. The method of claim 1, where the two or more sensors are located outside the *concave* platform.

18. The method of claim 1, where the two or more sensors are located under the *concave* platform.

19. A system for generating an input for controlling an application from movement within a *concave* platform of an omnidirectional locomotion system configured to support a user on the *concave* platform, the system comprising:

at least one processor; and at least one memory storing instructions, which when executed by the at least one processor causes the at least one processor to:

receive, from at least two or more sensors, movement data from movement within the *concave* platform configured to support the user;

calculate a velocity from the movement data;

calculate a heading from the movement data;

translate the velocity and the heading into [2-dimensional Cartesian coordinates] *at least one of a forward, backwards, or sideways movement input values*;

normalize the [2-dimensional Cartesian coordinates] *at least one of a forward, backwards, or sideways movement input values* into a minimum to maximum scale range; and transmit the normalized [coordinates] *movement input values* as the input.

20. The system of claim 19, wherein the velocity is calculated by a distance a foot of [a] *the* user travels divided by the time it took to travel the distance.

21. The system of claim 19, wherein the velocity is calculated by a pedometry rate.

22. The system of claim 21, wherein the pedometry rate is determined by monitoring a frequency of steps over a predefined interval.

23. The system of claim 19, wherein the velocity is calculated by monitoring an acceleration of a foot of [a] *the* user.

24. The system of claim 19, wherein the velocity is calculated by normalizing an angular velocity.

25. The system of claim 24, wherein the angular velocity is a change in rotation of a foot of [a] *the* user.

26. The system of claim 19, further comprising instructions, which when executed by the at least one processor causes the at least one processor to translate the heading relative to a real world axis.

27. The system of claim 26, wherein the real world axis is magnetic North.

28. The system of claim 27, further comprising instructions, which when executed by the at least one processor causes the at least one processor to calibrate the magnetic North to an initial orientation of [a] *the* user by an offset.

29. The system of claim 19, further comprising instructions, which when executed by the at least one processor causes the at least one processor to translate the heading relative to an orientation of a torso of [a] *the* user.

30. The system of claim 19, further comprising instructions, which when executed by the at least one processor causes the at least one processor to translate the heading relative to an orientation of a head of [a] *the* user.

31. The system of claim 19, wherein the minimum to maximum scale range is defined by gaming input descriptors.

[32. The system of claim 19, wherein a Y 2-dimensional Cartesian coordinate is for forward or backwards movement.]

[33. The system of claim 19, wherein an X 2-dimensional Cartesian coordinate is for sideways movement.]

34. The system of claim 19, where the two or more sensors are located within the *concave* platform.

35. The system of claim 19, where the two or more sensors are located outside the *concave* platform.

36. The system of claim 19, where the two or more sensors are located under the *concave* platform.

37. A non-transitory computer readable medium storing instructions, which when executed by at least one processor causes the at least one processor to:

receive, from at least two or more sensors, movement data from movement within a *concave* platform of an omni-directional locomotion system configured to support a user on the *concave* platform;

calculate a velocity from the movement data;

calculate a heading from the movement data;

translate the velocity and the heading into [2-dimensional Cartesian coordinates] *at least one of a forward, backwards, or sideways movement input values*;

normalize the [2-dimensional Cartesian coordinates] *at least one of a forward, backwards, or sideways movement input values* into a minimum to maximum scale range; and transmit the normalized [coordinates] *movement input values* as an input for controlling an application.

38. The non-transitory computer readable medium of claim 37, wherein the velocity is calculated by a distance a foot of [a] *the* user travels divided by the time it took to travel the distance.

39. The non-transitory computer readable medium of claim 37, wherein the velocity is calculated by a pedometry rate.

40. The non-transitory computer readable medium of claim 39, wherein the pedometry rate is determined by monitoring a frequency of steps over a predefined interval.

41. The non-transitory computer readable medium of claim 37, wherein the velocity is calculated by monitoring an acceleration of a foot of [a] *the* user.

42. The non-transitory computer readable medium of claim 37, wherein the velocity is calculated by normalizing an angular velocity.

43. The non-transitory computer readable medium of claim 42, wherein the angular velocity is a change in rotation of a foot of [a] *the* user.

44. The non-transitory computer readable medium of claim 37, further comprising instructions, which when executed by the at least one processor causes the at least one processor to translate the heading relative to a real world axis.

45. The non-transitory computer readable medium of claim 44, wherein the real world axis is magnetic North.

46. The non-transitory computer readable medium of claim 45, further comprising instructions, which when executed by the at least one processor causes the at least one processor to calibrate the magnetic North to an initial orientation of [a] *the* user by an offset.

47. The non-transitory computer readable medium of claim 37, further comprising instructions, which when executed by the at least one processor causes the at least one processor to translate the heading relative to an orientation of a torso of [a] *the* user.

48. The non-transitory computer readable medium of claim 37, further comprising instructions, which when executed by the at least one processor causes the at least one processor to translate the heading relative to an orientation of a head of [a] *the* user.

49. The non-transitory computer readable medium of claim 37, wherein the minimum to maximum scale range is defined by gaming input descriptors.

[50. The non-transitory computer readable medium of claim 37, wherein a Y 2-dimensional Cartesian coordinate is for forward or backwards movement.]

[51. The non-transitory computer readable medium of claim 37, wherein an X 2-dimensional Cartesian coordinate is for sideways movement.]

52. The non-transitory computer readable medium of claim 37, where the two or more sensors are located within the *concave* platform.

53. The non-transitory computer readable medium of claim 37, where the two or more sensors are located outside the *concave* platform.

54. The non-transitory computer readable medium of claim 37, where the two or more sensors are located under the *concave* platform.

* * * * *